US012721900B2

(12) United States Patent
Whitehead et al.

(10) Patent No.: US 12,721,900 B2
(45) Date of Patent: Sep. 1, 2026

(54) NON-VIRAL IMMUNO-TARGETING

(71) Applicant: UNIVERSITY OF WASHINGTON, Seattle, WA (US)

(72) Inventors: Nicholas P. Whitehead, Seattle, WA (US); Stanley C. Froehner, Seattle, WA (US)

(73) Assignee: University of Washington, Seattle, WA (US)

( * ) Notice: Subject to any disclaimer, the term of this patent is extended or adjusted under 35 U.S.C. 154(b) by 1272 days.

(21) Appl. No.: 17/625,722

(22) PCT Filed: Jul. 9, 2020

(86) PCT No.: PCT/US2020/041441
§ 371 (c)(1),
(2) Date: Jan. 7, 2022

(87) PCT Pub. No.: WO2021/007453
PCT Pub. Date: Jan. 14, 2021

(65) Prior Publication Data

US 2022/0280652 A1 Sep. 8, 2022

Related U.S. Application Data

(60) Provisional application No. 62/872,425, filed on Jul. 10, 2019.

(51) Int. Cl.

| | |
|---|---|
| ***A61K 47/68*** | (2017.01) |
| ***A61K 38/17*** | (2006.01) |
| ***A61K 47/69*** | (2017.01) |
| ***A61K 48/00*** | (2006.01) |
| ***C07K 16/28*** | (2006.01) |

(52) U.S. Cl.
CPC ...... *A61K 47/6849* (2017.08); *A61K 38/1719* (2013.01); *A61K 47/6807* (2017.08); *A61K 47/6913* (2017.08); *A61K 48/0025* (2013.01); *C07K 16/28* (2013.01); *C07K 2317/34* (2013.01)

(58) Field of Classification Search
CPC ............ A61K 47/6849; A61K 38/1719; A61K 47/6807; A61K 47/6913; A61K 48/0025; A61K 9/0019; A61K 9/127; C07K 16/28; C07K 2317/34; C07K 2317/76; C07K 14/78; A61P 21/00; A61P 21/04; C12N 15/87
See application file for complete search history.

(56) References Cited

U.S. PATENT DOCUMENTS

| | | | | |
|---|---|---|---|---|
| 9,926,557 | B2 | 3/2018 | De Kimpe et al. | |
| 2003/0216332 | A1 | 11/2003 | Chamberlain et al. | |
| 2005/0170509 | A1 | 8/2005 | Papahadjopoulos et al. | |
| 2008/0249052 | A1 | 10/2008 | Puan et al. | |
| 2010/0173302 | A1 | 7/2010 | Stuart | |
| 2017/0166903 | A1 | 6/2017 | Zhang et al. | |
| 2017/0196833 | A1 | 7/2017 | Markovic et al. | |
| 2017/0368198 | A1 * | 12/2017 | Xiao | A61K 48/0058 |
| 2018/0015172 | A1 | 1/2018 | Muzyczka et al. | |

FOREIGN PATENT DOCUMENTS

| | | | | |
|---|---|---|---|---|
| CN | 1339491 | A | 3/2002 | |
| JP | 2002-520038 | A | 7/2002 | |
| RU | 2674600 | C2 | 12/2018 | |
| WO | 2000/03683 | A2 | 1/2000 | |
| WO | 2010/132982 | A1 | 11/2010 | |
| WO | 2014/007620 | A2 | 1/2014 | |
| WO | 2018/035388 | A1 | 2/2018 | |
| WO | 2019/113393 | A1 | 6/2019 | |
| WO | WO-2019213024 | A1 * | 11/2019 | C07K 16/28 |

OTHER PUBLICATIONS

Sela-Culang, et al., Front. In Immunol. 2013; vol. 4 Article 302 (Year: 2013).*
UniProt.org; P14672-GLUT4_Human; Release version: 249; Release Date: Jun. 18, 2025; URL = https://www.uniprot.org/uniprotkb/P14672/entry ; Accessed: Oct. 22, 2025 (Year: 2025).*
Lebedeva, et al., European J Pharmaceutics and Biopharmaceutics 2000 50:101 (Year: 2000).*
International Search Report and Written Opinion mailed Feb. 17, 2021, issued in International Application No. PCT/US2020/041441, filed Jul. 9, 2020, 16 pages.
International Preliminary Report on Patentability mailed Jan. 11, 2022, issued in International Application No. PCT/US2020/041441, filed Jul. 9, 2020, 12 pages.
Caldas, C., et al., "Humanization of the Anti-CD18 Antibody 6.7: An Unexpected Effect of a Framework Residue in Binding to Antigen," Molecular Immunology 39(15):941-952, May 2003.
Du, J., "Molecular Basis of Recognition of Human Osteopontin by 2303, a Potential Therapeutic Antibody for Treatment of Rheumatoid Arthritis," Journal of Molecular Biology 382(4):835-842, Oct. 2008.
Friedman, J., "Immunolocalization of Glucose Transporter GLUT4 Within Human Skeletal Muscle," Diabetes 40(1):150-154, Jan. 1991.
James, D., et al., "Insulin-Regulatable Tissues Express a Unique Insulin-Sensitive Glucose Transport Protein," Nature 333(6169):183-185, May 1988.

(Continued)

*Primary Examiner* — Julie Wu
*Assistant Examiner* — Sydney Van Druff
(74) *Attorney, Agent, or Firm* — Christensen O'Connor Johnson Kindness PLLC

(57) ABSTRACT

The disclosure provides compositions and methods for delivering a payload to cells or tissues that express GLUT4. In some embodiments, the compositions comprise an antibody, or fragment or derivative thereof, that specifically binds to glucose transporter 4 ("GLUT4") protein, and a therapeutic payload conjugated thereto. In some exemplary embodiments, the compositions are useful for methods of treating a disease or condition in a subject with a genetic mutation in a gene encoding dystrophin protein, wherein the payload comprises a nucleic acid encoding a functional dystrophin protein or functional fragment thereof to ameliorate aspects of the disease.

17 Claims, 19 Drawing Sheets

Specification includes a Sequence Listing.

(56) References Cited

OTHER PUBLICATIONS

Xiang, J., et al., "Modification in Framework Region I Results in a Decreased Affinity of Chimeric Anti-Tag72 Antibody," Molecular Immunology 28(1-2):141-148, Jan. 1991.
Kunik, V., "Structural Consensus Among Antibodies Defines the Antigen Binding Site,"PLOS Computational Biology 8(2):e1002388, Feb. 2012, 12 pages.
Panka, D.J., "Variable Region Framework Differences Result in Decreased or Increased Affinity of Variant Anti-Digoxin Antibodies," Proceedings of the National Academy of Sciences (PNAS) 85(9):3080-3084, May 1988.
Extended European Search Report mailed Aug. 1, 2025, issued in related EP Application No. 25163101.6, filed Jul. 9, 2020, 5 pages.
Decision to Grant mailed Dec. 2, 2024, issued in related RU Application No. 2022102989, filed Jul. 9, 2020, 17 pages.
Office Action mailed Aug. 29, 2024, issued in related CA Application No. 3,145,992, filed Jul. 9, 2020, 4 pages.
Office Action and Search Report mailed Aug. 8, 2024, issued in related CL Application No. 202103444, filed Jul. 9, 2020, 36 pages.
Abouzeid, A.H., et al., "Anti-Cancer Activity of Anti-GLUT1 Antibody-Targeted Polymeric Micelles Co-Loaded With Curcumin and Doxorubicin" Journal of Drug Targeting 21(10):994-1000 , Dec. 2013.
Supplementary European Search Report mailed Sep. 25, 2023, issued in corresponding European Application No. 20836718.5, filed Jul. 9, 2020, 12 pages.
Notice of First Chinese Office Action mailed Oct. 30, 2023, issued in corresponding Chinese Application No. 202080054861.1, filed Jul. 9, 2020, 9 pages.
Chinese Search Report mailed Oct. 28, 2023, issued in corresponding Chinese Application No. 202080054861.1, filed Jul. 9, 2020, 2 pages.
Crispi, V., et al., "Duchenne Muscular Dystrophy: Genome Editing Gives New Hope for Treatment," Postgraduate Medical Journal 94(1111):296-304, May 2018.
Duchenne Muscular Dystrophy (DMD), cited Apr. 15, 2018 [online]. [Retrieved Mar. 1, 2022]. Retrieved from internet: <URL: https://www.mda.org/disease/duchenne-muscular-dystrophy> Muscular Dystrophy Association, pp. 1-5.
Hoffman, E.P., et al., "Improved Diagnosis of Becker Muscular Dystrophy by Dystrophin Testing," Neurology 39(8):1011-1017, Aug. 1989.
Lostal, W., et al., "Full-Length Dystrophin Reconstitution with Adeno-Associated Viral Vectors," Human Genome Therapy 25(6):552-562, Jun. 2014.
Tucker, D.F., et al., "Isolation of State-Dependent Monoclonal Antibodies Against the 12-Transmembrane Domain Glucose Transporter 4 Using Virus-Like Particles," PNAS 115(22):E4990-E4999, May 2018.
UniProt P14672. GLUT4_Human, May 8, 2019 [online]. [Retrieved May 17, 2022]. Retrieved from internet: <URL: https://www.uniprot.org/uniprot/P14672.txt?version=226>, pp. 1-8.
Xu, L., et al., "CRISPR-Mediated Genome Editing Restores Dystrophin Expression and Function in mdx Mice," The American Society of Gene & Cell Therapy 24(3):564-569, Mar. 2016.
Déas, Olivier, et al. "In vivo-targeted gene delivery using antibody-based nonviral vector." Human gene therapy 13.9 (2002): 1101-1114.
Mann, Anita, et al. "Differences in DNA condensation and release by lysine and arginine homopeptides govern their DNA delivery efficiencies." Molecular pharmaceutics 8.5 (2011): 1729-1741.
Partial European Search Report mailed Jun. 14, 2023, issued in EP Application No. 20836718.5, filed Jul. 9, 2020, 15 pages.
Notice of Reasons for Refusal mailed Jul. 23, 2024, issued in related JP Application No. 2022-500793, filed Jul. 9, 2020, 14 pages.
Lauritzen, H.P.M.M. and J.D. Schertzer, "Measuring GLUT4 Translocation in Mature Muscle Fibers," American Journal of Physiology, Endocrinology, and Metabolism 299(2):E169-E179, Aug. 2010.
Search Report mailed Feb. 9, 2024, issued in related RU Application No. 2022102989, filed Jul. 9, 2020, 4 pages.
Russian Office Action as mailed on Nov. 10, 2023, issued in corresponding Russian Application No. 2022102989, filed Jul. 9, 2020, 9 pages.

* cited by examiner

SEQUENCE LISTING

<160> NUMBER OF SEQ ID NOS: 101

<210> SEQ ID NO 1
<211> LENGTH: 36
<212> TYPE: PRT
<213> ORGANISM: Homo sapiens

<400> SEQUENCE: 1

Ile Asn Ala Pro Gln Lys Val Ile Glu Gln Ser Tyr Asn Glu Thr Trp
1 5 10 15

Leu Gly Arg Gln Gly Pro Glu Gly Pro Ser Ser Ile Pro Pro Gly Thr
20 25 30

Leu Thr Thr Leu
35

<210> SEQ ID NO 2
<211> LENGTH: 11
<212> TYPE: PRT
<213> ORGANISM: Homo sapiens

<400> SEQUENCE: 2

```
Gly Arg Gln Gly Pro Glu Gly Pro Ser Ser Ile
1               5                   10
```

<210> SEQ ID NO 3
<211> LENGTH: 36
<212> TYPE: PRT
<213> ORGANISM: Mus musculus

<400> SEQUENCE: 3

```
Ile Asn Ala Pro Gln Lys Val Ile Glu Gln Ser Tyr Asn Ala Thr Trp
1               5                   10                  15

Leu Gly Arg Gln Gly Pro Gly Gly Pro Asp Ser Ile Pro Gln Gly Thr
            20                  25                  30

Leu Thr Thr Leu
        35
```

<210> SEQ ID NO 4
<211> LENGTH: 11
<212> TYPE: PRT
<213> ORGANISM: Mus musculus

<400> SEQUENCE: 4

```
Gly Arg Gln Gly Pro Gly Gly Pro Asp Ser Ile
1               5                   10
```

<210> SEQ ID NO 5
<211> LENGTH: 3685
<212> TYPE: PRT
<213> ORGANISM: Homo sapiens

<400> SEQUENCE: 5

```
Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
```

-continued

```
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Arg Val
        435                 440                 445

Leu Met Asp Leu Gln Asn Gln Lys Leu Lys Glu Leu Asn Asp Trp Leu
    450                 455                 460

Thr Lys Thr Glu Glu Arg Thr Arg Lys Met Glu Glu Glu Pro Leu Gly
465                 470                 475                 480

Pro Asp Leu Glu Asp Leu Lys Arg Gln Val Gln Gln His Lys Val Leu
                485                 490                 495

Gln Glu Asp Leu Glu Gln Glu Gln Val Arg Val Asn Ser Leu Thr His
            500                 505                 510

Met Val Val Val Val Asp Glu Ser Ser Gly Asp His Ala Thr Ala Ala
        515                 520                 525

Leu Glu Glu Gln Leu Lys Val Leu Gly Asp Arg Trp Ala Asn Ile Cys
    530                 535                 540

Arg Trp Thr Glu Asp Arg Trp Val Leu Leu Gln Asp Ile Leu Leu Lys
545                 550                 555                 560

Trp Gln Arg Leu Thr Glu Glu Gln Cys Leu Phe Ser Ala Trp Leu Ser
                565                 570                 575

Glu Lys Glu Asp Ala Val Asn Lys Ile His Thr Thr Gly Phe Lys Asp
            580                 585                 590
```

-continued

Gln Asn Glu Met Leu Ser Ser Leu Gln Lys Leu Ala Val Leu Lys Ala
595 600 605

Asp Leu Glu Lys Lys Lys Gln Ser Met Gly Lys Leu Tyr Ser Leu Lys
610 615 620

Gln Asp Leu Leu Ser Thr Leu Lys Asn Lys Ser Val Thr Gln Lys Thr
625 630 635 640

Glu Ala Trp Leu Asp Asn Phe Ala Arg Cys Trp Asp Asn Leu Val Gln
645 650 655

Lys Leu Glu Lys Ser Thr Ala Gln Ile Ser Gln Ala Val Thr Thr Thr
660 665 670

Gln Pro Ser Leu Thr Gln Thr Thr Val Met Glu Thr Val Thr Thr Val
675 680 685

Thr Thr Arg Glu Gln Ile Leu Val Lys His Ala Gln Glu Glu Leu Pro
690 695 700

Pro Pro Pro Pro Gln Lys Lys Arg Gln Ile Thr Val Asp Ser Glu Ile
705 710 715 720

Arg Lys Arg Leu Asp Val Asp Ile Thr Glu Leu His Ser Trp Ile Thr
725 730 735

Arg Ser Glu Ala Val Leu Gln Ser Pro Glu Phe Ala Ile Phe Arg Lys
740 745 750

Glu Gly Asn Phe Ser Asp Leu Lys Glu Lys Val Asn Ala Ile Glu Arg
755 760 765

Glu Lys Ala Glu Lys Phe Arg Lys Leu Gln Asp Ala Ser Arg Ser Ala
770 775 780

Gln Ala Leu Val Glu Gln Met Val Asn Glu Gly Val Asn Ala Asp Ser
785 790 795 800

Ile Lys Gln Ala Ser Glu Gln Leu Asn Ser Arg Trp Ile Glu Phe Cys
805 810 815

Gln Leu Leu Ser Glu Arg Leu Asn Trp Leu Glu Tyr Gln Asn Asn Ile
820 825 830

Ile Ala Phe Tyr Asn Gln Leu Gln Gln Leu Glu Gln Met Thr Thr Thr
835 840 845

Ala Glu Asn Trp Leu Lys Ile Gln Pro Thr Thr Pro Ser Glu Pro Thr
850 855 860

Ala Ile Lys Ser Gln Leu Lys Ile Cys Lys Asp Glu Val Asn Arg Leu
865 870 875 880

Ser Gly Leu Gln Pro Gln Ile Glu Arg Leu Lys Ile Gln Ser Ile Ala
885 890 895

Leu Lys Glu Lys Gly Gln Gly Pro Met Phe Leu Asp Ala Asp Phe Val
900 905 910

Ala Phe Thr Asn His Phe Lys Gln Val Phe Ser Asp Val Gln Ala Arg
915 920 925

Glu Lys Glu Leu Gln Thr Ile Phe Asp Thr Leu Pro Pro Met Arg Tyr
930 935 940

Gln Glu Thr Met Ser Ala Ile Arg Thr Trp Val Gln Gln Ser Glu Thr
945 950 955 960

Lys Leu Ser Ile Pro Gln Leu Ser Val Thr Asp Tyr Glu Ile Met Glu
965 970 975

Gln Arg Leu Gly Glu Leu Gln Ala Leu Gln Ser Ser Leu Gln Glu Gln
980 985 990

Gln Ser Gly Leu Tyr Tyr Leu Ser Thr Thr Val Lys Glu Met Ser Lys
995 1000 1005

-continued

```
Lys Ala  Pro Ser Glu Ile Ser  Arg Lys Tyr Gln Ser  Glu Phe Glu
    1010                 1015                 1020

Glu Ile  Glu Gly Arg Trp Lys  Lys Leu Ser Ser Gln  Leu Val Glu
    1025                 1030                 1035

His Cys  Gln Lys Leu Glu Glu  Gln Met Asn Lys Leu  Arg Lys Ile
    1040                 1045                 1050

Gln Asn  His Ile Gln Thr Leu  Lys Lys Trp Met Ala  Glu Val Asp
    1055                 1060                 1065

Val Phe  Leu Lys Glu Glu Trp  Pro Ala Leu Gly Asp  Ser Glu Ile
    1070                 1075                 1080

Leu Lys  Lys Gln Leu Lys Gln  Cys Arg Leu Leu Val  Ser Asp Ile
    1085                 1090                 1095

Gln Thr  Ile Gln Pro Ser Leu  Asn Ser Val Asn Glu  Gly Gly Gln
    1100                 1105                 1110

Lys Ile  Lys Asn Glu Ala Glu  Pro Glu Phe Ala Ser  Arg Leu Glu
    1115                 1120                 1125

Thr Glu  Leu Lys Glu Leu Asn  Thr Gln Trp Asp His  Met Cys Gln
    1130                 1135                 1140

Gln Val  Tyr Ala Arg Lys Glu  Ala Leu Lys Gly Gly  Leu Glu Lys
    1145                 1150                 1155

Thr Val  Ser Leu Gln Lys Asp  Leu Ser Glu Met His  Glu Trp Met
    1160                 1165                 1170

Thr Gln  Ala Glu Glu Glu Tyr  Leu Glu Arg Asp Phe  Glu Tyr Lys
    1175                 1180                 1185

Thr Pro  Asp Glu Leu Gln Lys  Ala Val Glu Glu Met  Lys Arg Ala
    1190                 1195                 1200

Lys Glu  Glu Ala Gln Gln Lys  Glu Ala Lys Val Lys  Leu Leu Thr
    1205                 1210                 1215

Glu Ser  Val Asn Ser Val Ile  Ala Gln Ala Pro Pro  Val Ala Gln
    1220                 1225                 1230

Glu Ala  Leu Lys Lys Glu Leu  Glu Thr Leu Thr Thr  Asn Tyr Gln
    1235                 1240                 1245

Trp Leu  Cys Thr Arg Leu Asn  Gly Lys Cys Lys Thr  Leu Glu Glu
    1250                 1255                 1260

Val Trp  Ala Cys Trp His Glu  Leu Leu Ser Tyr Leu  Glu Lys Ala
    1265                 1270                 1275

Asn Lys  Trp Leu Asn Glu Val  Glu Phe Lys Leu Lys  Thr Thr Glu
    1280                 1285                 1290

Asn Ile  Pro Gly Gly Ala Glu  Glu Ile Ser Glu Val  Leu Asp Ser
    1295                 1300                 1305

Leu Glu  Asn Leu Met Arg His  Ser Glu Asp Asn Pro  Asn Gln Ile
    1310                 1315                 1320

Arg Ile  Leu Ala Gln Thr Leu  Thr Asp Gly Gly Val  Met Asp Glu
    1325                 1330                 1335

Leu Ile  Asn Glu Glu Leu Glu  Thr Phe Asn Ser Arg  Trp Arg Glu
    1340                 1345                 1350

Leu His  Glu Glu Ala Val Arg  Arg Gln Lys Leu Leu  Glu Gln Ser
    1355                 1360                 1365

Ile Gln  Ser Ala Gln Glu Thr  Glu Lys Ser Leu His  Leu Ile Gln
    1370                 1375                 1380

Glu Ser  Leu Thr Phe Ile Asp  Lys Gln Leu Ala Ala  Tyr Ile Ala
    1385                 1390                 1395

Asp Lys  Val Asp Ala Ala Gln  Met Pro Gln Glu Ala  Gln Lys Ile
```

-continued

```
    1400                1405                1410

Gln Ser  Asp Leu Thr Ser His  Glu Ile Ser Leu Glu  Glu Met Lys
    1415                1420                1425

Lys His  Asn Gln Gly Lys Glu  Ala Ala Gln Arg Val  Leu Ser Gln
    1430                1435                1440

Ile Asp  Val Ala Gln Lys Lys  Leu Gln Asp Val Ser  Met Lys Phe
    1445                1450                1455

Arg Leu  Phe Gln Lys Pro Ala  Asn Phe Glu Leu Arg  Leu Gln Glu
    1460                1465                1470

Ser Lys  Met Ile Leu Asp Glu  Val Lys Met His Leu  Pro Ala Leu
    1475                1480                1485

Glu Thr  Lys Ser Val Glu Gln  Glu Val Val Gln Ser  Gln Leu Asn
    1490                1495                1500

His Cys  Val Asn Leu Tyr Lys  Ser Leu Ser Glu Val  Lys Ser Glu
    1505                1510                1515

Val Glu  Met Val Ile Lys Thr  Gly Arg Gln Ile Val  Gln Lys Lys
    1520                1525                1530

Gln Thr  Glu Asn Pro Lys Glu  Leu Asp Glu Arg Val  Thr Ala Leu
    1535                1540                1545

Lys Leu  His Tyr Asn Glu Leu  Gly Ala Lys Val Thr  Glu Arg Lys
    1550                1555                1560

Gln Gln  Leu Glu Lys Cys Leu  Lys Leu Ser Arg Lys  Met Arg Lys
    1565                1570                1575

Glu Met  Asn Val Leu Thr Glu  Trp Leu Ala Ala Thr  Asp Met Glu
    1580                1585                1590

Leu Thr  Lys Arg Ser Ala Val  Glu Gly Met Pro Ser  Asn Leu Asp
    1595                1600                1605

Ser Glu  Val Ala Trp Gly Lys  Ala Thr Gln Lys Glu  Ile Glu Lys
    1610                1615                1620

Gln Lys  Val His Leu Lys Ser  Ile Thr Glu Val Gly  Glu Ala Leu
    1625                1630                1635

Lys Thr  Val Leu Gly Lys Lys  Glu Thr Leu Val Glu  Asp Lys Leu
    1640                1645                1650

Ser Leu  Leu Asn Ser Asn Trp  Ile Ala Val Thr Ser  Arg Ala Glu
    1655                1660                1665

Glu Trp  Leu Asn Leu Leu Leu  Glu Tyr Gln Lys His  Met Glu Thr
    1670                1675                1680

Phe Asp  Gln Asn Val Asp His  Ile Thr Lys Trp Ile  Ile Gln Ala
    1685                1690                1695

Asp Thr  Leu Leu Asp Glu Ser  Glu Lys Lys Lys Pro  Gln Gln Lys
    1700                1705                1710

Glu Asp  Val Leu Lys Arg Leu  Lys Ala Glu Leu Asn  Asp Ile Arg
    1715                1720                1725

Pro Lys  Val Asp Ser Thr Arg  Asp Gln Ala Ala Asn  Leu Met Ala
    1730                1735                1740

Asn Arg  Gly Asp His Cys Arg  Lys Leu Val Glu Pro  Gln Ile Ser
    1745                1750                1755

Glu Leu  Asn His Arg Phe Ala  Ala Ile Ser His Arg  Ile Lys Thr
    1760                1765                1770

Gly Lys  Ala Ser Ile Pro Leu  Lys Glu Leu Glu Gln  Phe Asn Ser
    1775                1780                1785

Asp Ile  Gln Lys Leu Leu Glu  Pro Leu Glu Ala Glu  Ile Gln Gln
    1790                1795                1800
```

-continued

```
Gly Val  Asn Leu Lys Glu Glu  Asp Phe Asn Lys Asp  Met Asn Glu
    1805                 1810                 1815

Asp Asn  Glu Gly Thr Val Lys  Glu Leu Leu Gln Arg  Gly Asp Asn
    1820                 1825                 1830

Leu Gln  Gln Arg Ile Thr Asp  Glu Arg Lys Arg Glu  Glu Ile Lys
    1835                 1840                 1845

Ile Lys  Gln Gln Leu Leu Gln  Thr Lys His Asn Ala  Leu Lys Asp
    1850                 1855                 1860

Leu Arg  Ser Gln Arg Arg Lys  Lys Ala Leu Glu Ile  Ser His Gln
    1865                 1870                 1875

Trp Tyr  Gln Tyr Lys Arg Gln  Ala Asp Asp Leu Leu  Lys Cys Leu
    1880                 1885                 1890

Asp Asp  Ile Glu Lys Lys Leu  Ala Ser Leu Pro Glu  Pro Arg Asp
    1895                 1900                 1905

Glu Arg  Lys Ile Lys Glu Ile  Asp Arg Glu Leu Gln  Lys Lys Lys
    1910                 1915                 1920

Glu Glu  Leu Asn Ala Val Arg  Arg Gln Ala Glu Gly  Leu Ser Glu
    1925                 1930                 1935

Asp Gly  Ala Ala Met Ala Val  Glu Pro Thr Gln Ile  Gln Leu Ser
    1940                 1945                 1950

Lys Arg  Trp Arg Glu Ile Glu  Ser Lys Phe Ala Gln  Phe Arg Arg
    1955                 1960                 1965

Leu Asn  Phe Ala Gln Ile His  Thr Val Arg Glu Glu  Thr Met Met
    1970                 1975                 1980

Val Met  Thr Glu Asp Met Pro  Leu Glu Ile Ser Tyr  Val Pro Ser
    1985                 1990                 1995

Thr Tyr  Leu Thr Glu Ile Thr  His Val Ser Gln Ala  Leu Leu Glu
    2000                 2005                 2010

Val Glu  Gln Leu Leu Asn Ala  Pro Asp Leu Cys Ala  Lys Asp Phe
    2015                 2020                 2025

Glu Asp  Leu Phe Lys Gln Glu  Glu Ser Leu Lys Asn  Ile Lys Asp
    2030                 2035                 2040

Ser Leu  Gln Gln Ser Ser Gly  Arg Ile Asp Ile Ile  His Ser Lys
    2045                 2050                 2055

Lys Thr  Ala Ala Leu Gln Ser  Ala Thr Pro Val Glu  Arg Val Lys
    2060                 2065                 2070

Leu Gln  Glu Ala Leu Ser Gln  Leu Asp Phe Gln Trp  Glu Lys Val
    2075                 2080                 2085

Asn Lys  Met Tyr Lys Asp Arg  Gln Gly Arg Phe Asp  Arg Ser Val
    2090                 2095                 2100

Glu Lys  Trp Arg Arg Phe His  Tyr Asp Ile Lys Ile  Phe Asn Gln
    2105                 2110                 2115

Trp Leu  Thr Glu Ala Glu Gln  Phe Leu Arg Lys Thr  Gln Ile Pro
    2120                 2125                 2130

Glu Asn  Trp Glu His Ala Lys  Tyr Lys Trp Tyr Leu  Lys Glu Leu
    2135                 2140                 2145

Gln Asp  Gly Ile Gly Gln Arg  Gln Thr Val Val Arg  Thr Leu Asn
    2150                 2155                 2160

Ala Thr  Gly Glu Glu Ile Ile  Gln Gln Ser Ser Lys  Thr Asp Ala
    2165                 2170                 2175

Ser Ile  Leu Gln Glu Lys Leu  Gly Ser Leu Asn Leu  Arg Trp Gln
    2180                 2185                 2190
```

Glu Val Cys Lys Gln Leu Ser Asp Arg Lys Lys Arg Leu Glu Glu
2195 2200 2205

Gln Lys Asn Ile Leu Ser Glu Phe Gln Arg Asp Leu Asn Glu Phe
2210 2215 2220

Val Leu Trp Leu Glu Glu Ala Asp Asn Ile Ala Ser Ile Pro Leu
2225 2230 2235

Glu Pro Gly Lys Glu Gln Gln Leu Lys Glu Lys Leu Glu Gln Val
2240 2245 2250

Lys Leu Leu Val Glu Glu Leu Pro Leu Arg Gln Gly Ile Leu Lys
2255 2260 2265

Gln Leu Asn Glu Thr Gly Gly Pro Val Leu Val Ser Ala Pro Ile
2270 2275 2280

Ser Pro Glu Glu Gln Asp Lys Leu Glu Asn Lys Leu Lys Gln Thr
2285 2290 2295

Asn Leu Gln Trp Ile Lys Val Ser Arg Ala Leu Pro Glu Lys Gln
2300 2305 2310

Gly Glu Ile Glu Ala Gln Ile Lys Asp Leu Gly Gln Leu Glu Lys
2315 2320 2325

Lys Leu Glu Asp Leu Glu Glu Gln Leu Asn His Leu Leu Leu Trp
2330 2335 2340

Leu Ser Pro Ile Arg Asn Gln Leu Glu Ile Tyr Asn Gln Pro Asn
2345 2350 2355

Gln Glu Gly Pro Phe Asp Val Gln Glu Thr Glu Ile Ala Val Gln
2360 2365 2370

Ala Lys Gln Pro Asp Val Glu Glu Ile Leu Ser Lys Gly Gln His
2375 2380 2385

Leu Tyr Lys Glu Lys Pro Ala Thr Gln Pro Val Lys Arg Lys Leu
2390 2395 2400

Glu Asp Leu Ser Ser Glu Trp Lys Ala Val Asn Arg Leu Leu Gln
2405 2410 2415

Glu Leu Arg Ala Lys Gln Pro Asp Leu Ala Pro Gly Leu Thr Thr
2420 2425 2430

Ile Gly Ala Ser Pro Thr Gln Thr Val Thr Leu Val Thr Gln Pro
2435 2440 2445

Val Val Thr Lys Glu Thr Ala Ile Ser Lys Leu Glu Met Pro Ser
2450 2455 2460

Ser Leu Met Leu Glu Val Pro Ala Leu Ala Asp Phe Asn Arg Ala
2465 2470 2475

Trp Thr Glu Leu Thr Asp Trp Leu Ser Leu Leu Asp Gln Val Ile
2480 2485 2490

Lys Ser Gln Arg Val Met Val Gly Asp Leu Glu Asp Ile Asn Glu
2495 2500 2505

Met Ile Ile Lys Gln Lys Ala Thr Met Gln Asp Leu Glu Gln Arg
2510 2515 2520

Arg Pro Gln Leu Glu Glu Leu Ile Thr Ala Ala Gln Asn Leu Lys
2525 2530 2535

Asn Lys Thr Ser Asn Gln Glu Ala Arg Thr Ile Ile Thr Asp Arg
2540 2545 2550

Ile Glu Arg Ile Gln Asn Gln Trp Asp Glu Val Gln Glu His Leu
2555 2560 2565

Gln Asn Arg Arg Gln Gln Leu Asn Glu Met Leu Lys Asp Ser Thr
2570 2575 2580

Gln Trp Leu Glu Ala Lys Glu Glu Ala Glu Gln Val Leu Gly Gln

```
    2585                2590                2595

Ala Arg  Ala Lys Leu Glu Ser  Trp Lys Glu Gly Pro  Tyr Thr Val
    2600                2605                2610

Asp Ala  Ile Gln Lys Lys Ile  Thr Glu Thr Lys Gln  Leu Ala Lys
    2615                2620                2625

Asp Leu  Arg Gln Trp Gln Thr  Asn Val Asp Val Ala  Asn Asp Leu
    2630                2635                2640

Ala Leu  Lys Leu Leu Arg Asp  Tyr Ser Ala Asp Asp  Thr Arg Lys
    2645                2650                2655

Val His  Met Ile Thr Glu Asn  Ile Asn Ala Ser Trp  Arg Ser Ile
    2660                2665                2670

His Lys  Arg Val Ser Glu Arg  Glu Ala Ala Leu Glu  Glu Thr His
    2675                2680                2685

Arg Leu  Leu Gln Gln Phe Pro  Leu Asp Leu Glu Lys  Phe Leu Ala
    2690                2695                2700

Trp Leu  Thr Glu Ala Glu Thr  Thr Ala Asn Val Leu  Gln Asp Ala
    2705                2710                2715

Thr Arg  Lys Glu Arg Leu Leu  Glu Asp Ser Lys Gly  Val Lys Glu
    2720                2725                2730

Leu Met  Lys Gln Trp Gln Asp  Leu Gln Gly Glu Ile  Glu Ala His
    2735                2740                2745

Thr Asp  Val Tyr His Asn Leu  Asp Glu Asn Ser Gln  Lys Ile Leu
    2750                2755                2760

Arg Ser  Leu Glu Gly Ser Asp  Asp Ala Val Leu Leu  Gln Arg Arg
    2765                2770                2775

Leu Asp  Asn Met Asn Phe Lys  Trp Ser Glu Leu Arg  Lys Lys Ser
    2780                2785                2790

Leu Asn  Ile Arg Ser His Leu  Glu Ala Ser Ser Asp  Gln Trp Lys
    2795                2800                2805

Arg Leu  His Leu Ser Leu Gln  Glu Leu Leu Val Trp  Leu Gln Leu
    2810                2815                2820

Lys Asp  Asp Glu Leu Ser Arg  Gln Ala Pro Ile Gly  Gly Asp Phe
    2825                2830                2835

Pro Ala  Val Gln Lys Gln Asn  Asp Val His Arg Ala  Phe Lys Arg
    2840                2845                2850

Glu Leu  Lys Thr Lys Glu Pro  Val Ile Met Ser Thr  Leu Glu Thr
    2855                2860                2865

Val Arg  Ile Phe Leu Thr Glu  Gln Pro Leu Glu Gly  Leu Glu Lys
    2870                2875                2880

Leu Tyr  Gln Glu Pro Arg Glu  Leu Pro Pro Glu Glu  Arg Ala Gln
    2885                2890                2895

Asn Val  Thr Arg Leu Leu Arg  Lys Gln Ala Glu Glu  Val Asn Thr
    2900                2905                2910

Glu Trp  Glu Lys Leu Asn Leu  His Ser Ala Asp Trp  Gln Arg Lys
    2915                2920                2925

Ile Asp  Glu Thr Leu Glu Arg  Leu Gln Glu Leu Gln  Glu Ala Thr
    2930                2935                2940

Asp Glu  Leu Asp Leu Lys Leu  Arg Gln Ala Glu Val  Ile Lys Gly
    2945                2950                2955

Ser Trp  Gln Pro Val Gly Asp  Leu Leu Ile Asp Ser  Leu Gln Asp
    2960                2965                2970

His Leu  Glu Lys Val Lys Ala  Leu Arg Gly Glu Ile  Ala Pro Leu
    2975                2980                2985
```

-continued

```
Lys Glu Asn Val Ser His Val Asn Asp Leu Ala Arg Gln Leu Thr
    2990                2995                3000

Thr Leu Gly Ile Gln Leu Ser Pro Tyr Asn Leu Ser Thr Leu Glu
    3005                3010                3015

Asp Leu Asn Thr Arg Trp Lys Leu Leu Gln Val Ala Val Glu Asp
    3020                3025                3030

Arg Val Arg Gln Leu His Glu Ala His Arg Asp Phe Gly Pro Ala
    3035                3040                3045

Ser Gln His Phe Leu Ser Thr Ser Val Gln Gly Pro Trp Glu Arg
    3050                3055                3060

Ala Ile Ser Pro Asn Lys Val Pro Tyr Tyr Ile Asn His Glu Thr
    3065                3070                3075

Gln Thr Thr Cys Trp Asp His Pro Lys Met Thr Glu Leu Tyr Gln
    3080                3085                3090

Ser Leu Ala Asp Leu Asn Asn Val Arg Phe Ser Ala Tyr Arg Thr
    3095                3100                3105

Ala Met Lys Leu Arg Arg Leu Gln Lys Ala Leu Cys Leu Asp Leu
    3110                3115                3120

Leu Ser Leu Ser Ala Ala Cys Asp Ala Leu Asp Gln His Asn Leu
    3125                3130                3135

Lys Gln Asn Asp Gln Pro Met Asp Ile Leu Gln Ile Ile Asn Cys
    3140                3145                3150

Leu Thr Thr Ile Tyr Asp Arg Leu Glu Gln Glu His Asn Asn Leu
    3155                3160                3165

Val Asn Val Pro Leu Cys Val Asp Met Cys Leu Asn Trp Leu Leu
    3170                3175                3180

Asn Val Tyr Asp Thr Gly Arg Thr Gly Arg Ile Arg Val Leu Ser
    3185                3190                3195

Phe Lys Thr Gly Ile Ile Ser Leu Cys Lys Ala His Leu Glu Asp
    3200                3205                3210

Lys Tyr Arg Tyr Leu Phe Lys Gln Val Ala Ser Ser Thr Gly Phe
    3215                3220                3225

Cys Asp Gln Arg Arg Leu Gly Leu Leu Leu His Asp Ser Ile Gln
    3230                3235                3240

Ile Pro Arg Gln Leu Gly Glu Val Ala Ser Phe Gly Gly Ser Asn
    3245                3250                3255

Ile Glu Pro Ser Val Arg Ser Cys Phe Gln Phe Ala Asn Asn Lys
    3260                3265                3270

Pro Glu Ile Glu Ala Ala Leu Phe Leu Asp Trp Met Arg Leu Glu
    3275                3280                3285

Pro Gln Ser Met Val Trp Leu Pro Val Leu His Arg Val Ala Ala
    3290                3295                3300

Ala Glu Thr Ala Lys His Gln Ala Lys Cys Asn Ile Cys Lys Glu
    3305                3310                3315

Cys Pro Ile Ile Gly Phe Arg Tyr Arg Ser Leu Lys His Phe Asn
    3320                3325                3330

Tyr Asp Ile Cys Gln Ser Cys Phe Phe Ser Gly Arg Val Ala Lys
    3335                3340                3345

Gly His Lys Met His Tyr Pro Met Val Glu Tyr Cys Thr Pro Thr
    3350                3355                3360

Thr Ser Gly Glu Asp Val Arg Asp Phe Ala Lys Val Leu Lys Asn
    3365                3370                3375
```

-continued

Lys Phe Arg Thr Lys Arg Tyr Phe Ala Lys His Pro Arg Met Gly
3380 3385 3390

Tyr Leu Pro Val Gln Thr Val Leu Glu Gly Asp Asn Met Glu Thr
3395 3400 3405

Pro Val Thr Leu Ile Asn Phe Trp Pro Val Asp Ser Ala Pro Ala
3410 3415 3420

Ser Ser Pro Gln Leu Ser His Asp Asp Thr His Ser Arg Ile Glu
3425 3430 3435

His Tyr Ala Ser Arg Leu Ala Glu Met Glu Asn Ser Asn Gly Ser
3440 3445 3450

Tyr Leu Asn Asp Ser Ile Ser Pro Asn Glu Ser Ile Asp Asp Glu
3455 3460 3465

His Leu Leu Ile Gln His Tyr Cys Gln Ser Leu Asn Gln Asp Ser
3470 3475 3480

Pro Leu Ser Gln Pro Arg Ser Pro Ala Gln Ile Leu Ile Ser Leu
3485 3490 3495

Glu Ser Glu Glu Arg Gly Glu Leu Glu Arg Ile Leu Ala Asp Leu
3500 3505 3510

Glu Glu Glu Asn Arg Asn Leu Gln Ala Glu Tyr Asp Arg Leu Lys
3515 3520 3525

Gln Gln His Glu His Lys Gly Leu Ser Pro Leu Pro Ser Pro Pro
3530 3535 3540

Glu Met Met Pro Thr Ser Pro Gln Ser Pro Arg Asp Ala Glu Leu
3545 3550 3555

Ile Ala Glu Ala Lys Leu Leu Arg Gln His Lys Gly Arg Leu Glu
3560 3565 3570

Ala Arg Met Gln Ile Leu Glu Asp His Asn Lys Gln Leu Glu Ser
3575 3580 3585

Gln Leu His Arg Leu Arg Gln Leu Leu Glu Gln Pro Gln Ala Glu
3590 3595 3600

Ala Lys Val Asn Gly Thr Thr Val Ser Ser Pro Ser Thr Ser Leu
3605 3610 3615

Gln Arg Ser Asp Ser Ser Gln Pro Met Leu Leu Arg Val Val Gly
3620 3625 3630

Ser Gln Thr Ser Asp Ser Met Gly Glu Glu Asp Leu Leu Ser Pro
3635 3640 3645

Pro Gln Asp Thr Ser Thr Gly Leu Glu Glu Val Met Glu Gln Leu
3650 3655 3660

Asn Asn Ser Phe Pro Ser Ser Arg Gly Arg Asn Thr Pro Gly Lys
3665 3670 3675

Pro Met Arg Glu Asp Thr Met
3680 3685

<210> SEQ ID NO 6
<211> LENGTH: 3678
<212> TYPE: PRT
<213> ORGANISM: Mus musculus

<400> SEQUENCE: 6

Met Leu Trp Trp Glu Glu Val Glu Asp Cys Tyr Glu Arg Glu Asp Val
1 5 10 15

Gln Lys Lys Thr Phe Thr Lys Trp Ile Asn Ala Gln Phe Ser Lys Phe
20 25 30

Gly Lys Gln His Ile Asp Asn Leu Phe Ser Asp Leu Gln Asp Gly Lys
35 40 45

-continued

```
Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Lys Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Thr Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Ser Ser Trp Ser Asp Gly Leu Ala Leu Asn Ala Leu Ile His Ser His
                165                 170                 175

Arg Pro Asp Leu Phe Asp Trp Asn Ser Val Val Ser Gln His Ser Ala
            180                 185                 190

Thr Gln Arg Leu Glu His Ala Phe Asn Ile Ala Lys Cys Gln Leu Gly
        195                 200                 205

Ile Glu Lys Leu Leu Asp Pro Glu Asp Val Ala Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Thr Ser Ser Lys Val Thr Arg Glu Glu His Phe Gln Leu His His Gln
            260                 265                 270

Met His Tyr Ser Gln Gln Ile Thr Val Ser Leu Ala Gln Gly Tyr Glu
        275                 280                 285

Gln Thr Ser Ser Ser Pro Lys Pro Arg Phe Lys Ser Tyr Ala Phe Thr
    290                 295                 300

Gln Ala Ala Tyr Val Ala Thr Ser Asp Ser Thr Gln Ser Pro Tyr Pro
305                 310                 315                 320

Ser Gln His Leu Glu Ala Pro Arg Asp Lys Ser Leu Asp Ser Ser Leu
                325                 330                 335

Met Glu Thr Glu Val Asn Leu Asp Ser Tyr Gln Thr Ala Leu Glu Glu
            340                 345                 350

Val Leu Ser Trp Leu Leu Ser Ala Glu Asp Thr Leu Arg Ala Gln Gly
        355                 360                 365

Glu Ile Ser Asn Asp Val Glu Glu Val Lys Glu Gln Phe His Ala His
    370                 375                 380

Glu Gly Phe Met Met Asp Leu Thr Ser His Gln Gly Leu Val Gly Asn
385                 390                 395                 400

Val Leu Gln Leu Gly Ser Gln Leu Val Gly Lys Gly Lys Leu Ser Glu
                405                 410                 415

Asp Glu Glu Ala Glu Val Gln Glu Gln Met Asn Leu Leu Asn Ser Arg
            420                 425                 430

Trp Glu Cys Leu Arg Val Ala Ser Met Glu Lys Gln Ser Lys Leu His
        435                 440                 445

Lys Val Leu Met Asp Leu Gln Asn Gln Lys Leu Lys Glu Leu Asp Asp
    450                 455                 460
```

-continued

```
Trp Leu Thr Lys Thr Glu Glu Arg Thr Lys Lys Met Glu Glu Glu Pro
465                 470                 475                 480

Phe Gly Pro Asp Leu Glu Asp Leu Lys Cys Gln Val Gln Gln His Lys
                485                 490                 495

Val Leu Gln Glu Asp Leu Glu Gln Glu Gln Val Arg Val Asn Ser Leu
            500                 505                 510

Thr His Met Val Val Val Val Asp Glu Ser Ser Gly Asp His Ala Thr
        515                 520                 525

Ala Ala Leu Glu Glu Gln Leu Lys Val Leu Gly Asp Arg Trp Ala Asn
    530                 535                 540

Ile Cys Arg Trp Thr Glu Asp Arg Trp Ile Val Leu Gln Asp Ile Leu
545                 550                 555                 560

Leu Lys Trp Gln His Phe Thr Glu Glu Gln Cys Leu Phe Ser Thr Trp
                565                 570                 575

Leu Ser Glu Lys Glu Asp Ala Met Lys Asn Ile Gln Thr Ser Gly Phe
            580                 585                 590

Lys Asp Gln Asn Glu Met Met Ser Ser Leu His Lys Ile Ser Thr Leu
        595                 600                 605

Lys Ile Asp Leu Glu Lys Lys Lys Pro Thr Met Glu Lys Leu Ser Ser
    610                 615                 620

Leu Asn Gln Asp Leu Leu Ser Ala Leu Lys Asn Lys Ser Val Thr Gln
625                 630                 635                 640

Lys Met Glu Ile Trp Met Glu Asn Phe Ala Gln Arg Trp Asp Asn Leu
                645                 650                 655

Thr Gln Lys Leu Glu Lys Ser Ser Ala Gln Ile Ser Gln Ala Val Thr
            660                 665                 670

Thr Thr Gln Pro Ser Leu Thr Gln Thr Thr Val Met Glu Thr Val Thr
        675                 680                 685

Met Val Thr Thr Arg Glu Gln Ile Met Val Lys His Ala Gln Glu Glu
    690                 695                 700

Leu Pro Pro Pro Pro Pro Gln Lys Lys Arg Gln Ile Thr Val Asp Ser
705                 710                 715                 720

Glu Leu Arg Lys Arg Leu Asp Val Asp Ile Thr Glu Leu His Ser Trp
                725                 730                 735

Ile Thr Arg Ser Glu Ala Val Leu Gln Ser Ser Glu Phe Ala Val Tyr
            740                 745                 750

Arg Lys Glu Gly Asn Ile Ser Asp Leu Gln Glu Lys Val Asn Ala Ile
        755                 760                 765

Ala Arg Glu Lys Ala Glu Lys Phe Arg Lys Leu Gln Asp Ala Ser Arg
    770                 775                 780

Ser Ala Gln Ala Leu Val Glu Gln Met Ala Asn Glu Gly Val Asn Ala
785                 790                 795                 800

Glu Ser Ile Arg Gln Ala Ser Glu Gln Leu Asn Ser Arg Trp Thr Glu
                805                 810                 815

Phe Cys Gln Leu Leu Ser Glu Arg Val Asn Trp Leu Glu Tyr Gln Thr
            820                 825                 830

Asn Ile Ile Thr Phe Tyr Asn Gln Leu Gln Gln Leu Glu Gln Met Thr
        835                 840                 845

Thr Thr Ala Glu Asn Leu Leu Lys Thr Gln Ser Thr Thr Leu Ser Glu
    850                 855                 860

Pro Thr Ala Ile Lys Ser Gln Leu Lys Ile Cys Lys Asp Glu Val Asn
865                 870                 875                 880

Arg Leu Ser Ala Leu Gln Pro Gln Ile Glu Gln Leu Lys Ile Gln Ser
```

-continued

```
                885                 890                 895

Leu Gln Leu Lys Glu Lys Gly Gln Gly Pro Met Phe Leu Asp Ala Asp
            900                 905                 910

Phe Val Ala Phe Thr Asn His Phe Asn His Ile Phe Asp Gly Val Arg
        915                 920                 925

Ala Lys Glu Lys Glu Leu Gln Thr Ile Phe Asp Thr Leu Pro Pro Met
    930                 935                 940

Arg Tyr Gln Glu Thr Met Ser Ser Ile Arg Thr Trp Ile Gln Gln Ser
945                 950                 955                 960

Glu Ser Lys Leu Ser Val Pro Tyr Leu Ser Val Thr Glu Tyr Glu Ile
                965                 970                 975

Met Glu Glu Arg Leu Gly Lys Leu Gln Ala Leu Gln Ser Ser Leu Lys
            980                 985                 990

Glu Gln Gln Asn Gly Phe Asn Tyr  Leu Ser Asp Thr Val  Lys Glu Met
        995                 1000                1005

Ala Lys  Lys Ala Pro Ser Glu  Ile Cys Gln Lys Tyr  Leu Ser Glu
    1010                 1015                 1020

Phe Glu  Glu Ile Glu Gly His  Trp Lys Lys Leu Ser  Ser Gln Leu
    1025                 1030                 1035

Val Glu  Ser Cys Gln Lys Leu  Glu Glu His Met Asn  Lys Leu Arg
    1040                 1045                 1050

Lys Phe  Gln Asn His Ile Lys  Thr Leu Gln Lys Trp  Met Ala Glu
    1055                 1060                 1065

Val Asp  Val Phe Leu Lys Glu  Glu Trp Pro Ala Leu  Gly Asp Ala
    1070                 1075                 1080

Glu Ile  Leu Lys Lys Gln Leu  Lys Gln Cys Arg Leu  Leu Val Gly
    1085                 1090                 1095

Asp Ile  Gln Thr Ile Gln Pro  Ser Leu Asn Ser Val  Asn Glu Gly
    1100                 1105                 1110

Gly Gln  Lys Ile Lys Ser Glu  Ala Glu Leu Glu Phe  Ala Ser Arg
    1115                 1120                 1125

Leu Glu  Thr Glu Leu Arg Glu  Leu Asn Thr Gln Trp  Asp His Ile
    1130                 1135                 1140

Cys Arg  Gln Val Tyr Thr Arg  Lys Glu Ala Leu Lys  Ala Gly Leu
    1145                 1150                 1155

Asp Lys  Thr Val Ser Leu Gln  Lys Asp Leu Ser Glu  Met His Glu
    1160                 1165                 1170

Trp Met  Thr Gln Ala Glu Glu  Glu Tyr Leu Glu Arg  Asp Phe Glu
    1175                 1180                 1185

Tyr Lys  Thr Pro Asp Glu Leu  Gln Thr Ala Val Glu  Glu Met Lys
    1190                 1195                 1200

Arg Ala  Lys Glu Glu Ala Leu  Gln Lys Glu Thr Lys  Val Lys Leu
    1205                 1210                 1215

Leu Thr  Glu Thr Val Asn Ser  Val Ile Ala His Ala  Pro Pro Ser
    1220                 1225                 1230

Ala Gln  Glu Ala Leu Lys Lys  Glu Leu Glu Thr Leu  Thr Thr Asn
    1235                 1240                 1245

Tyr Gln  Trp Leu Cys Thr Arg  Leu Asn Gly Lys Cys  Lys Thr Leu
    1250                 1255                 1260

Glu Glu  Val Trp Ala Cys Trp  His Glu Leu Leu Ser  Tyr Leu Glu
    1265                 1270                 1275

Lys Ala  Asn Lys Trp Leu Asn  Glu Val Glu Leu Lys  Leu Lys Thr
    1280                 1285                 1290
```

-continued

```
Met Glu  Asn Val Pro Ala Gly  Pro Glu Glu Ile Thr  Glu Val Leu
    1295                 1300                 1305

Glu Ser  Leu Glu Asn Leu Met  His His Ser Glu Glu  Asn Pro Asn
    1310                 1315                 1320

Gln Ile  Arg Leu Leu Ala Gln  Thr Leu Thr Asp Gly  Gly Val Met
    1325                 1330                 1335

Asp Glu  Leu Ile Asn Glu Glu  Leu Glu Thr Phe Asn  Ser Arg Trp
    1340                 1345                 1350

Arg Glu  Leu His Glu Glu Ala  Val Arg Lys Gln Lys  Leu Leu Glu
    1355                 1360                 1365

Gln Ser  Ile Gln Ser Ala Gln  Glu Ile Glu Lys Ser  Leu His Leu
    1370                 1375                 1380

Ile Gln  Glu Ser Leu Glu Phe  Ile Asp Lys Gln Leu  Ala Ala Tyr
    1385                 1390                 1395

Ile Thr  Asp Lys Val Asp Ala  Ala Gln Met Pro Gln  Glu Ala Gln
    1400                 1405                 1410

Lys Ile  Gln Ser Asp Leu Thr  Ser His Glu Ile Ser  Leu Glu Glu
    1415                 1420                 1425

Met Lys  Lys His Asn Gln Gly  Lys Asp Ala Asn Gln  Arg Val Leu
    1430                 1435                 1440

Ser Gln  Ile Asp Val Ala Gln  Lys Lys Leu Gln Asp  Val Ser Met
    1445                 1450                 1455

Lys Phe  Arg Leu Phe Gln Lys  Pro Ala Asn Phe Glu  Gln Arg Leu
    1460                 1465                 1470

Glu Glu  Ser Lys Met Ile Leu  Asp Glu Val Lys Met  His Leu Pro
    1475                 1480                 1485

Ala Leu  Glu Thr Lys Ser Val  Glu Gln Glu Val Ile  Gln Ser Gln
    1490                 1495                 1500

Leu Ser  His Cys Val Asn Leu  Tyr Lys Ser Leu Ser  Glu Val Lys
    1505                 1510                 1515

Ser Glu  Val Glu Met Val Ile  Lys Thr Gly Arg Gln  Ile Val Gln
    1520                 1525                 1530

Lys Lys  Gln Thr Glu Asn Pro  Lys Glu Leu Asp Glu  Arg Val Thr
    1535                 1540                 1545

Ala Leu  Lys Leu His Tyr Asn  Glu Leu Gly Ala Lys  Val Thr Glu
    1550                 1555                 1560

Arg Lys  Gln Gln Leu Glu Lys  Cys Leu Lys Leu Ser  Arg Lys Met
    1565                 1570                 1575

Arg Lys  Glu Met Asn Val Leu  Thr Glu Trp Leu Ala  Ala Thr Asp
    1580                 1585                 1590

Thr Glu  Leu Thr Lys Arg Ser  Ala Val Glu Gly Met  Pro Ser Asn
    1595                 1600                 1605

Leu Asp  Ser Glu Val Ala Trp  Gly Lys Ala Thr Gln  Lys Glu Ile
    1610                 1615                 1620

Glu Lys  Gln Lys Ala His Leu  Lys Ser Val Thr Glu  Leu Gly Glu
    1625                 1630                 1635

Ser Leu  Lys Met Val Leu Gly  Lys Lys Glu Thr Leu  Val Glu Asp
    1640                 1645                 1650

Lys Leu  Ser Leu Leu Asn Ser  Asn Trp Ile Ala Val  Thr Ser Arg
    1655                 1660                 1665

Val Glu  Glu Trp Leu Asn Leu  Leu Leu Glu Tyr Gln  Lys His Met
    1670                 1675                 1680
```

-continued

```
Glu Thr  Phe Asp Gln Asn Ile  Glu Gln Ile Thr Lys  Trp Ile Ile
    1685                 1690                 1695

His Ala  Asp Glu Leu Leu Asp  Glu Ser Glu Lys Lys  Lys Pro Gln
    1700                 1705                 1710

Gln Lys  Glu Asp Ile Leu Lys  Arg Leu Lys Ala Glu  Met Asn Asp
    1715                 1720                 1725

Met Arg  Pro Lys Val Asp Ser  Thr Arg Asp Gln Ala  Ala Lys Leu
    1730                 1735                 1740

Met Ala  Asn Arg Gly Asp His  Cys Arg Lys Val Val  Glu Pro Gln
    1745                 1750                 1755

Ile Ser  Glu Leu Asn Arg Arg  Phe Ala Ala Ile Ser  His Arg Ile
    1760                 1765                 1770

Lys Thr  Gly Lys Ala Ser Ile  Pro Leu Lys Glu Leu  Glu Gln Phe
    1775                 1780                 1785

Asn Ser  Asp Ile Gln Lys Leu  Leu Glu Pro Leu Glu  Ala Glu Ile
    1790                 1795                 1800

Gln Gln  Gly Val Asn Leu Lys  Glu Glu Asp Phe Asn  Lys Asp Met
    1805                 1810                 1815

Ser Glu  Asp Asn Glu Gly Thr  Val Asn Glu Leu Leu  Gln Arg Gly
    1820                 1825                 1830

Asp Asn  Leu Gln Gln Arg Ile  Thr Asp Glu Arg Lys  Arg Glu Glu
    1835                 1840                 1845

Ile Lys  Ile Lys Gln Gln Leu  Leu Gln Thr Lys His  Asn Ala Leu
    1850                 1855                 1860

Lys Asp  Leu Arg Ser Gln Arg  Arg Lys Lys Ala Leu  Glu Ile Ser
    1865                 1870                 1875

His Gln  Trp Tyr Gln Tyr Lys  Arg Gln Ala Asp Asp  Leu Leu Lys
    1880                 1885                 1890

Cys Leu  Asp Glu Ile Glu Lys  Lys Leu Ala Ser Leu  Pro Glu Pro
    1895                 1900                 1905

Arg Asp  Glu Arg Lys Leu Lys  Glu Ile Asp Arg Glu  Leu Gln Lys
    1910                 1915                 1920

Lys Lys  Glu Glu Leu Asn Ala  Val Arg Arg Gln Ala  Glu Gly Leu
    1925                 1930                 1935

Ser Glu  Asn Gly Ala Ala Met  Ala Val Glu Pro Thr  Gln Ile Gln
    1940                 1945                 1950

Leu Ser  Lys Arg Trp Arg Gln  Ile Glu Ser Asn Phe  Ala Gln Phe
    1955                 1960                 1965

Arg Arg  Leu Asn Phe Ala Gln  Ile His Thr Leu His  Glu Glu Thr
    1970                 1975                 1980

Met Val  Val Thr Thr Glu Asp  Met Pro Leu Asp Val  Ser Tyr Val
    1985                 1990                 1995

Pro Ser  Thr Tyr Leu Thr Glu  Ile Ser His Ile Leu  Gln Ala Leu
    2000                 2005                 2010

Ser Glu  Val Asp His Leu Leu  Asn Thr Pro Glu Leu  Cys Ala Lys
    2015                 2020                 2025

Asp Phe  Glu Asp Leu Phe Lys  Gln Glu Glu Ser Leu  Lys Asn Ile
    2030                 2035                 2040

Lys Asp  Asn Leu Gln Gln Ile  Ser Gly Arg Ile Asp  Ile Ile His
    2045                 2050                 2055

Lys Lys  Lys Thr Ala Ala Leu  Gln Ser Ala Thr Ser  Met Glu Lys
    2060                 2065                 2070

Val Lys  Val Gln Glu Ala Val  Ala Gln Met Asp Phe  Gln Gly Glu
```

-continued

```
    2075                2080                2085

Lys Leu  His Arg Met Tyr Lys  Glu Arg Gln Gly Arg  Phe Asp Arg
    2090                2095                2100

Ser Val  Glu Lys Trp Arg His  Phe His Tyr Asp Met  Lys Val Phe
    2105                2110                2115

Asn Gln  Trp Leu Asn Glu Val  Glu Gln Phe Phe Lys  Lys Thr Gln
    2120                2125                2130

Asn Pro  Glu Asn Trp Glu His  Ala Lys Tyr Lys Trp  Tyr Leu Lys
    2135                2140                2145

Glu Leu  Gln Asp Gly Ile Gly  Gln Arg Gln Ala Val  Val Arg Thr
    2150                2155                2160

Leu Asn  Ala Thr Gly Glu Glu  Ile Ile Gln Gln Ser  Ser Lys Thr
    2165                2170                2175

Asp Val  Asn Ile Leu Gln Glu  Lys Leu Gly Ser Leu  Ser Leu Arg
    2180                2185                2190

Trp His  Asp Ile Cys Lys Glu  Leu Ala Glu Arg Arg  Lys Arg Ile
    2195                2200                2205

Glu Glu  Gln Lys Asn Val Leu  Ser Glu Phe Gln Arg  Asp Leu Asn
    2210                2215                2220

Glu Phe  Val Leu Trp Leu Glu  Glu Ala Asp Asn Ile  Ala Ile Thr
    2225                2230                2235

Pro Leu  Gly Asp Glu Gln Gln  Leu Lys Glu Gln Leu  Glu Gln Val
    2240                2245                2250

Lys Leu  Leu Ala Glu Glu Leu  Pro Leu Arg Gln Gly  Ile Leu Lys
    2255                2260                2265

Gln Leu  Asn Glu Thr Gly Gly  Ala Val Leu Val Ser  Ala Pro Ile
    2270                2275                2280

Arg Pro  Glu Glu Gln Asp Lys  Leu Glu Lys Lys Leu  Lys Gln Thr
    2285                2290                2295

Asn Leu  Gln Trp Ile Lys Val  Ser Arg Ala Leu Pro  Glu Lys Gln
    2300                2305                2310

Gly Glu  Leu Glu Val His Leu  Lys Asp Phe Arg Gln  Leu Glu Glu
    2315                2320                2325

Gln Leu  Asp His Leu Leu Leu  Trp Leu Ser Pro Ile  Arg Asn Gln
    2330                2335                2340

Leu Glu  Ile Tyr Asn Gln Pro  Ser Gln Ala Gly Pro  Phe Asp Ile
    2345                2350                2355

Lys Glu  Ile Glu Val Thr Val  His Gly Lys Gln Ala  Asp Val Glu
    2360                2365                2370

Arg Leu  Leu Ser Lys Gly Gln  His Leu Tyr Lys Glu  Lys Pro Ser
    2375                2380                2385

Thr Gln  Pro Val Lys Arg Lys  Leu Glu Asp Leu Arg  Ser Glu Trp
    2390                2395                2400

Glu Ala  Val Asn His Leu Leu  Arg Glu Leu Arg Thr  Lys Gln Pro
    2405                2410                2415

Asp Arg  Ala Pro Gly Leu Ser  Thr Thr Gly Ala Ser  Ala Ser Gln
    2420                2425                2430

Thr Val  Thr Leu Val Thr Gln  Ser Val Val Thr Lys  Glu Thr Val
    2435                2440                2445

Ile Ser  Lys Leu Glu Met Pro  Ser Ser Leu Leu Leu  Glu Val Pro
    2450                2455                2460

Ala Leu  Ala Asp Phe Asn Arg  Ala Trp Thr Glu Leu  Thr Asp Trp
    2465                2470                2475
```

```
Leu Ser  Leu Leu Asp Arg Val  Ile Lys Ser Gln Arg  Val Met Val
    2480                 2485                 2490

Gly Asp  Leu Glu Asp Ile Asn  Glu Met Ile Ile Lys  Gln Lys Ala
    2495                 2500                 2505

Thr Leu  Gln Asp Leu Glu Gln  Arg Arg Pro Gln Leu  Glu Glu Leu
    2510                 2515                 2520

Ile Thr  Ala Ala Gln Asn Leu  Lys Asn Lys Thr Ser  Asn Gln Glu
    2525                 2530                 2535

Ala Arg  Thr Ile Ile Thr Asp  Arg Ile Glu Arg Ile  Gln Ile Gln
    2540                 2545                 2550

Trp Asp  Glu Val Gln Glu Gln  Leu Gln Asn Arg Arg  Gln Gln Leu
    2555                 2560                 2565

Asn Glu  Met Leu Lys Asp Ser  Thr Gln Trp Leu Glu  Ala Lys Glu
    2570                 2575                 2580

Glu Ala  Glu Gln Val Ile Gly  Gln Val Arg Gly Lys  Leu Asp Ser
    2585                 2590                 2595

Trp Lys  Glu Gly Pro His Thr  Val Asp Ala Ile Gln  Lys Lys Ile
    2600                 2605                 2610

Thr Glu  Thr Lys Gln Leu Ala  Lys Asp Leu Arg Gln  Arg Gln Ile
    2615                 2620                 2625

Ser Val  Asp Val Ala Asn Asp  Leu Ala Leu Lys Leu  Leu Arg Asp
    2630                 2635                 2640

Tyr Ser  Ala Asp Asp Thr Arg  Lys Val His Met Ile  Thr Glu Asn
    2645                 2650                 2655

Ile Asn  Thr Ser Trp Gly Asn  Ile His Lys Arg Val  Ser Glu Gln
    2660                 2665                 2670

Glu Ala  Ala Leu Glu Glu Thr  His Arg Leu Leu Gln  Gln Phe Pro
    2675                 2680                 2685

Leu Asp  Leu Glu Lys Phe Leu  Ser Trp Ile Thr Glu  Ala Glu Thr
    2690                 2695                 2700

Thr Ala  Asn Val Leu Gln Asp  Ala Ser Arg Lys Glu  Lys Leu Leu
    2705                 2710                 2715

Glu Asp  Ser Arg Gly Val Arg  Glu Leu Met Lys Pro  Trp Gln Asp
    2720                 2725                 2730

Leu Gln  Gly Glu Ile Glu Thr  His Thr Asp Ile Tyr  His Asn Leu
    2735                 2740                 2745

Asp Glu  Asn Gly Gln Lys Ile  Leu Arg Ser Leu Glu  Gly Ser Asp
    2750                 2755                 2760

Glu Ala  Pro Leu Leu Gln Arg  Arg Leu Asp Asn Met  Asn Phe Lys
    2765                 2770                 2775

Trp Ser  Glu Leu Gln Lys Lys  Ser Leu Asn Ile Arg  Ser His Leu
    2780                 2785                 2790

Glu Ala  Ser Ser Asp Gln Trp  Lys Arg Leu His Leu  Ser Leu Gln
    2795                 2800                 2805

Glu Leu  Leu Val Trp Leu Gln  Leu Lys Asp Asp Glu  Leu Ser Arg
    2810                 2815                 2820

Gln Ala  Pro Ile Gly Gly Asp  Phe Pro Ala Val Gln  Lys Gln Asn
    2825                 2830                 2835

Asp Ile  His Arg Ala Phe Lys  Arg Glu Leu Lys Thr  Lys Glu Pro
    2840                 2845                 2850

Val Ile  Met Ser Thr Leu Glu  Thr Val Arg Ile Phe  Leu Thr Glu
    2855                 2860                 2865
```

-continued

```
Gln Pro  Leu Glu Gly Leu Glu  Lys Leu Tyr Gln Glu  Pro Arg Glu
    2870                 2875                 2880

Leu Pro  Pro Glu Glu Arg Ala  Gln Asn Val Thr Arg  Leu Leu Arg
    2885                 2890                 2895

Lys Gln  Ala Glu Glu Val Asn  Ala Glu Trp Asp Lys  Leu Asn Leu
    2900                 2905                 2910

Arg Ser  Ala Asp Trp Gln Arg  Lys Ile Asp Glu Ala  Leu Glu Arg
    2915                 2920                 2925

Leu Gln  Glu Leu Gln Glu Ala  Ala Asp Glu Leu Asp  Leu Lys Leu
    2930                 2935                 2940

Arg Gln  Ala Glu Val Ile Lys  Gly Ser Trp Gln Pro  Val Gly Asp
    2945                 2950                 2955

Leu Leu  Ile Asp Ser Leu Gln  Asp His Leu Glu Lys  Val Lys Ala
    2960                 2965                 2970

Leu Arg  Gly Glu Ile Ala Pro  Leu Lys Glu Asn Val  Asn Arg Val
    2975                 2980                 2985

Asn Asp  Leu Ala His Gln Leu  Thr Thr Leu Gly Ile  Gln Leu Ser
    2990                 2995                 3000

Pro Tyr  Asn Leu Ser Thr Leu  Glu Asp Leu Asn Thr  Arg Trp Arg
    3005                 3010                 3015

Leu Leu  Gln Val Ala Val Glu  Asp Arg Val Arg Gln  Leu His Glu
    3020                 3025                 3030

Ala His  Arg Asp Phe Gly Pro  Ala Ser Gln His Phe  Leu Ser Thr
    3035                 3040                 3045

Ser Val  Gln Gly Pro Trp Glu  Arg Ala Ile Ser Pro  Asn Lys Val
    3050                 3055                 3060

Pro Tyr  Tyr Ile Asn His Glu  Thr Gln Thr Thr Cys  Trp Asp His
    3065                 3070                 3075

Pro Lys  Met Thr Glu Leu Tyr  Gln Ser Leu Ala Asp  Leu Asn Asn
    3080                 3085                 3090

Val Arg  Phe Ser Ala Tyr Arg  Thr Ala Met Lys Leu  Arg Arg Leu
    3095                 3100                 3105

Gln Lys  Ala Leu Cys Leu Asp  Leu Leu Ser Leu Ser  Ala Ala Cys
    3110                 3115                 3120

Asp Ala  Leu Asp Gln His Asn  Leu Lys Gln Asn Asp  Gln Pro Met
    3125                 3130                 3135

Asp Ile  Leu Gln Ile Ile Asn  Cys Leu Thr Thr Ile  Tyr Asp Arg
    3140                 3145                 3150

Leu Glu  Gln Glu His Asn Asn  Leu Val Asn Val Pro  Leu Cys Val
    3155                 3160                 3165

Asp Met  Cys Leu Asn Trp Leu  Leu Asn Val Tyr Asp  Thr Gly Arg
    3170                 3175                 3180

Thr Gly  Arg Ile Arg Val Leu  Ser Phe Lys Thr Gly  Ile Ile Ser
    3185                 3190                 3195

Leu Cys  Lys Ala His Leu Glu  Asp Lys Tyr Arg Tyr  Leu Phe Lys
    3200                 3205                 3210

Gln Val  Ala Ser Ser Thr Gly  Phe Cys Asp Gln Arg  Arg Leu Gly
    3215                 3220                 3225

Leu Leu  Leu His Asp Ser Ile  Gln Ile Pro Arg Gln  Leu Gly Glu
    3230                 3235                 3240

Val Ala  Ser Phe Gly Gly Ser  Asn Ile Glu Pro Ser  Val Arg Ser
    3245                 3250                 3255

Cys Phe  Gln Phe Ala Asn Asn  Lys Pro Glu Ile Glu  Ala Ala Leu
```

-continued

```
    3260                3265                3270

Phe Leu  Asp Trp Met Arg Leu  Glu Pro Gln Ser Met  Val Trp Leu
    3275                3280                3285

Pro Val  Leu His Arg Val Ala  Ala Ala Glu Thr Ala  Lys His Gln
    3290                3295                3300

Ala Lys  Cys Asn Ile Cys Lys  Glu Cys Pro Ile Ile  Gly Phe Arg
    3305                3310                3315

Tyr Arg  Ser Leu Lys His Phe  Asn Tyr Asp Ile Cys  Gln Ser Cys
    3320                3325                3330

Phe Phe  Ser Gly Arg Val Ala  Lys Gly His Lys Met  His Tyr Pro
    3335                3340                3345

Met Val  Glu Tyr Cys Thr Pro  Thr Thr Ser Gly Glu  Asp Val Arg
    3350                3355                3360

Asp Phe  Ala Lys Val Leu Lys  Asn Lys Phe Arg Thr  Lys Arg Tyr
    3365                3370                3375

Phe Ala  Lys His Pro Arg Met  Gly Tyr Leu Pro Val  Gln Thr Val
    3380                3385                3390

Leu Glu  Gly Asp Asn Met Glu  Thr Pro Val Thr Leu  Ile Asn Phe
    3395                3400                3405

Trp Pro  Val Asp Ser Ala Pro  Ala Ser Ser Pro Gln  Leu Ser His
    3410                3415                3420

Asp Asp  Thr His Ser Arg Ile  Glu His Tyr Ala Ser  Arg Leu Ala
    3425                3430                3435

Glu Met  Glu Asn Ser Asn Gly  Ser Tyr Leu Asn Asp  Ser Ile Ser
    3440                3445                3450

Pro Asn  Glu Ser Ile Asp Asp  Glu His Leu Leu Ile  Gln His Tyr
    3455                3460                3465

Cys Gln  Ser Leu Asn Gln Asp  Ser Pro Leu Ser Gln  Pro Arg Ser
    3470                3475                3480

Pro Ala  Gln Ile Leu Ile Ser  Leu Glu Ser Glu Glu  Arg Gly Glu
    3485                3490                3495

Leu Glu  Arg Ile Leu Ala Asp  Leu Glu Glu Glu Asn  Arg Asn Leu
    3500                3505                3510

Gln Ala  Glu Tyr Asp Arg Leu  Lys Gln Gln His Glu  His Lys Gly
    3515                3520                3525

Leu Ser  Pro Leu Pro Ser Pro  Pro Glu Met Met Pro  Thr Ser Pro
    3530                3535                3540

Gln Ser  Pro Arg Asp Ala Glu  Leu Ile Ala Glu Ala  Lys Leu Leu
    3545                3550                3555

Arg Gln  His Lys Gly Arg Leu  Glu Ala Arg Met Gln  Ile Leu Glu
    3560                3565                3570

Asp His  Asn Lys Gln Leu Glu  Ser Gln Leu His Arg  Leu Arg Gln
    3575                3580                3585

Leu Leu  Glu Gln Pro Gln Ala  Glu Ala Lys Val Asn  Gly Thr Thr
    3590                3595                3600

Val Ser  Ser Pro Ser Thr Ser  Leu Gln Arg Ser Asp  Ser Ser Gln
    3605                3610                3615

Pro Met  Leu Leu Arg Val Val  Gly Ser Gln Thr Ser  Glu Ser Met
    3620                3625                3630

Gly Glu  Glu Asp Leu Leu Ser  Pro Pro Gln Asp Thr  Ser Thr Gly
    3635                3640                3645

Leu Glu  Glu Val Met Glu Gln  Leu Asn Asn Ser Phe  Pro Ser Ser
    3650                3655                3660
```

-continued

```
Arg Gly Arg Asn Ala Pro Gly Lys Pro Met Arg Glu Asp Thr Met
    3665                3670                3675


<210> SEQ ID NO 7
<211> LENGTH: 3699
<212> TYPE: PRT
<213> ORGANISM: Rattus norvegicus

<400> SEQUENCE: 7

Met Glu Asp Glu Arg Glu Asp Val Gln Lys Lys Thr Phe Thr Lys Trp
1               5                   10                  15

Ile Asn Ala Gln Phe Ser Lys Phe Gly Lys Gln His Ile Asp Asn Leu
            20                  25                  30

Phe Ser Asp Leu Gln Asp Gly Lys Arg Leu Leu Asp Leu Leu Glu Gly
        35                  40                  45

Leu Thr Gly Gln Lys Leu Pro Lys Glu Lys Gly Ser Thr Arg Val His
    50                  55                  60

Ala Leu Asn Asn Val Asn Lys Ala Leu Gln Val Leu Gln Lys Asn Asn
65                  70                  75                  80

Val Asp Leu Val Asn Ile Gly Ser Thr Asp Ile Val Asp Gly Asn His
                85                  90                  95

Lys Leu Thr Leu Gly Leu Ile Trp Asn Ile Ile Leu His Trp Gln Val
            100                 105                 110

Lys Asn Val Met Lys Thr Ile Met Ala Gly Leu Gln Gln Thr Asn Ser
        115                 120                 125

Glu Lys Ile Leu Leu Ser Trp Val Arg Glu Ser Thr Arg Asn Tyr Pro
    130                 135                 140

Gln Val Asn Val Leu Asn Phe Thr Ser Ser Trp Ser Asp Gly Leu Ala
145                 150                 155                 160

Leu Asn Ala Leu Ile His Ser His Arg Pro Asp Leu Phe Asp Trp Asn
                165                 170                 175

Ser Val Val Ser Gln Gln Ser Ala Thr Gln Arg Leu Glu His Ala Phe
            180                 185                 190

Asn Ile Ala Lys Cys Gln Leu Gly Ile Glu Lys Leu Leu Asp Pro Glu
        195                 200                 205

Asp Val Ala Thr Thr Tyr Pro Asp Lys Lys Ser Ile Leu Met Tyr Ile
    210                 215                 220

Thr Ser Leu Phe Gln Val Leu Pro Gln Gln Val Ser Ile Glu Ala Ile
225                 230                 235                 240

Arg Glu Val Glu Met Leu Pro Arg Pro Ser Lys Val Thr Arg Glu Glu
                245                 250                 255

His Phe Gln Leu His His Gln Met His Tyr Ser Gln Gln Ile Thr Val
            260                 265                 270

Ser Leu Ala Gln Gly Tyr Glu Gln Thr Ser Ser Ser Pro Lys Pro Arg
        275                 280                 285

Phe Lys Ser Tyr Ala Phe Thr Gln Ala Ala Tyr Val Ala Thr Ser Asp
    290                 295                 300

Ser Ser Gln Ser Pro Tyr Pro Ser Gln His Leu Glu Ala Pro Gly Ser
305                 310                 315                 320

Lys Ser Phe Gly Ser Ser Leu Ile Glu Thr Glu Val Asn Leu Asp Ser
                325                 330                 335

Tyr Gln Thr Ala Leu Glu Glu Val Leu Ser Trp Leu Leu Ser Ala Glu
            340                 345                 350

Asp Thr Leu Arg Ala Gln Gly Glu Ile Ser Lys Asp Val Glu Glu Val
```

-continued

```
        355                 360                 365

Lys Glu Gln Phe His Ala His Glu Gly Phe Met Met Asp Leu Thr Ser
    370                 375                 380

His Gln Gly Leu Val Gly Asn Val Leu Gln Leu Gly Ser Arg Leu Val
385                 390                 395                 400

Gly Lys Gly Lys Leu Thr Glu Asp Glu Glu Thr Glu Val Gln Glu Gln
                405                 410                 415

Met Asn Leu Leu Asn Ser Arg Trp Glu Cys Leu Arg Val Ala Ser Met
            420                 425                 430

Glu Lys Gln Ser Asn Leu His Lys Val Leu Met Asp Leu Gln Asn Gln
        435                 440                 445

Lys Leu Lys Glu Leu Asp Asp Trp Leu Thr Lys Thr Glu Glu Arg Thr
    450                 455                 460

Lys Lys Met Glu Glu Glu Pro Leu Gly Pro Asp Leu Glu Asp Leu Lys
465                 470                 475                 480

Cys Gln Val Gln Gln His Lys Val Leu Gln Glu Asp Leu Glu Gln Glu
                485                 490                 495

Gln Val Arg Val Asn Ser Leu Thr His Met Val Val Val Val Asp Glu
            500                 505                 510

Ser Ser Gly Asp His Ala Thr Ala Ala Leu Glu Glu Gln Leu Lys Val
        515                 520                 525

Leu Gly Asp Arg Trp Ala Asn Ile Cys Lys Trp Thr Glu Asp Arg Trp
    530                 535                 540

Ile Leu Leu Gln Asp Ile Leu Leu Lys Trp Gln Arg Phe Thr Glu Glu
545                 550                 555                 560

Gln Cys Leu Phe Ser Lys Trp Leu Ser Glu Lys Glu Asp Ala Met Lys
                565                 570                 575

Asn Ile Gln Thr Ser Gly Phe Glu Asp Gln Asn Glu Met Val Ser Ser
            580                 585                 590

Leu Gln Asn Ile Ser Ala Leu Lys Ile Asp Leu Glu Lys Lys Lys Gln
        595                 600                 605

Ser Met Glu Lys Leu Ser Ser Leu Asn Gln Asp Leu Leu Ser Ala Leu
    610                 615                 620

Lys Asn Lys Ser Val Thr Gln Lys Met Glu Met Trp Met Glu Asn Phe
625                 630                 635                 640

Ala Gln Arg Trp Asp Asn Leu Thr Gln Lys Leu Glu Lys Ser Ser Ala
                645                 650                 655

Gln Ile Ser Gln Ala Val Thr Thr Thr Gln Pro Ser Leu Thr Gln Thr
            660                 665                 670

Thr Val Met Glu Thr Val Thr Met Val Thr Thr Arg Glu Gln Ile Met
        675                 680                 685

Val Lys His Ala Gln Glu Glu Leu Pro Pro Pro Pro Pro Gln Lys Lys
    690                 695                 700

Arg Gln Ile Thr Val Asp Ser Glu Ile Arg Lys Arg Leu Asp Val Asp
705                 710                 715                 720

Ile Thr Glu Leu His Ser Trp Ile Thr Arg Ser Glu Ala Val Leu Gln
                725                 730                 735

Ser Ser Glu Phe Ala Val Tyr Arg Lys Glu Gly Asn Ile Ser Asp Leu
            740                 745                 750

Lys Glu Lys Val Asn Ala Ile Ala Arg Glu Lys Ala Glu Lys Phe Arg
        755                 760                 765

Lys Leu Gln Asp Ala Ser Arg Ser Ala Gln Ala Leu Val Glu Gln Met
    770                 775                 780
```

-continued

```
Val Asn Glu Gly Val Asn Ala Glu Ser Ile Arg Gln Ala Ser Glu Gln
785                 790                 795                 800

Leu Asn Ser Arg Trp Thr Glu Phe Cys Gln Leu Leu Ser Glu Arg Val
                805                 810                 815

Asn Trp Leu Glu Tyr Gln Asn Asn Ile Ile Thr Phe Tyr Asn Gln Leu
            820                 825                 830

Gln Gln Leu Glu Gln Met Thr Thr Thr Ala Glu Asn Leu Leu Lys Thr
        835                 840                 845

Gln Pro Thr Thr Leu Ser Glu Pro Thr Ala Ile Lys Ser Gln Leu Lys
    850                 855                 860

Ile Cys Lys Asp Glu Val Asn Arg Leu Ser Ala Leu Gln Pro Gln Ile
865                 870                 875                 880

Glu Arg Leu Lys Ile Gln Ser Leu Thr Leu Lys Glu Lys Gly Gln Gly
                885                 890                 895

Pro Met Phe Leu Asp Ala Asp Phe Val Ala Phe Thr Asn His Phe Asn
            900                 905                 910

Tyr Val Phe Asp Gly Val Arg Ala Arg Glu Lys Glu Leu Gln Thr Ile
        915                 920                 925

Phe Asp Thr Leu Pro Pro Met Arg Tyr Gln Glu Thr Met Ser Ser Ile
    930                 935                 940

Arg Thr Trp Ile Gln Gln Ser Glu Asn Lys Leu Ser Ile Pro His Leu
945                 950                 955                 960

Ser Val Thr Glu Tyr Glu Ile Met Glu Glu Arg Leu Gly Lys Leu Gln
                965                 970                 975

Ala Leu Gln Ser Ser Leu Lys Glu Gln Gln Asn Gly Phe Asn Tyr Leu
            980                 985                 990

Asn Ala Thr Val Lys Glu Ile Ala  Lys Lys Ala Pro Ser  Glu Ile Ser
        995                 1000                1005

Gln Lys  Tyr Gln Ser Glu Phe  Glu Glu Val Glu Gly  Arg Trp Lys
    1010                1015                1020

Lys Leu  Ser Thr Gln Leu Val  Glu His Cys Gln Lys  Leu Glu Glu
    1025                1030                1035

His Met  Asn Lys Leu Arg Lys  Phe Gln Asn His Lys  Lys Thr Leu
    1040                1045                1050

Gln Lys  Trp Met Ala Glu Val  Asp Val Phe Leu Lys  Glu Glu Trp
    1055                1060                1065

Pro Ala  Leu Gly Asp Ala Glu  Ile Leu Lys Lys Gln  Leu Lys Gln
    1070                1075                1080

Cys Arg  Leu Leu Val Gly Asp  Ile Gln Thr Ile Gln  Pro Ser Leu
    1085                1090                1095

Asn Ser  Val Asn Glu Gly Gly  Gln Lys Ile Lys Ser  Glu Ala Glu
    1100                1105                1110

Phe Glu  Phe Ala Ser Arg Leu  Glu Lys Glu Leu Lys  Glu Leu Asn
    1115                1120                1125

Thr Gln  Trp Asp His Ile Cys  Arg Gln Val Tyr Thr  Arg Lys Glu
    1130                1135                1140

Ala Leu  Lys Ala Gly Leu Asp  Lys Thr Val Ser Leu  Gln Lys Asp
    1145                1150                1155

Leu Ser  Glu Met His Glu Trp  Met Thr Gln Ala Glu  Glu Glu Tyr
    1160                1165                1170

Leu Glu  Arg Asp Phe Glu Tyr  Lys Thr Pro Asp Glu  Leu Gln Thr
    1175                1180                1185
```

-continued

Ala Val Glu Glu Met Lys Arg Ala Lys Glu Glu Ala Leu Gln Lys
1190 1195 1200

Glu Ala Lys Val Lys Leu Leu Thr Glu Thr Val Asn Ser Val Ile
1205 1210 1215

Ser Gln Ala Pro Pro Ala Ala Gln Glu Ala Leu Lys Lys Glu Leu
1220 1225 1230

Glu Thr Leu Thr Thr Asn Tyr Gln Trp Leu Cys Thr Arg Leu Asn
1235 1240 1245

Gly Lys Cys Lys Thr Leu Glu Glu Val Trp Ala Cys Trp His Glu
1250 1255 1260

Leu Leu Ser Tyr Leu Glu Lys Ala Asn Lys Trp Leu Asn Glu Val
1265 1270 1275

Glu Leu Lys Leu Lys Ala Thr Glu Asn Val Pro Ala Gly Ala Glu
1280 1285 1290

Glu Ile Thr Glu Val Leu Glu Ser Leu Glu Asn Leu Met His His
1295 1300 1305

Ser Glu Glu Asn Pro Asn Gln Ile Arg Leu Leu Ala Gln Thr Leu
1310 1315 1320

Thr Asp Gly Gly Val Met Asp Glu Leu Ile Asn Glu Glu Leu Glu
1325 1330 1335

Thr Phe Asn Ser Arg Trp Arg Glu Leu His Glu Glu Ala Val Arg
1340 1345 1350

Lys Gln Lys Leu Leu Glu Gln Ser Ile Gln Ser Ala Gln Glu Ile
1355 1360 1365

Glu Lys Ser Leu His Leu Ile Gln Glu Ser Leu Glu Phe Ile Asp
1370 1375 1380

Lys Gln Leu Ala Ala Tyr Ile Ala Asp Lys Val Asp Ala Ala Gln
1385 1390 1395

Met Pro Gln Glu Ala Gln Lys Ile Gln Ser Asp Leu Thr Ser His
1400 1405 1410

Glu Ile Ser Leu Glu Glu Met Lys Lys His Asn Gln Gly Lys Asp
1415 1420 1425

Ala Asn Gln Arg Val Leu Ser Gln Ile Asp Val Ala Gln Lys Lys
1430 1435 1440

Leu Gln Asp Val Ser Ile Lys Phe Arg Leu Phe Gln Lys Pro Ala
1445 1450 1455

Asn Phe Glu Gln Arg Leu Glu Glu Ser Lys Met Ile Leu Asp Glu
1460 1465 1470

Val Lys Met His Leu Pro Ala Leu Glu Thr Lys Ser Val Glu Gln
1475 1480 1485

Glu Val Val Gln Ser Gln Leu Ser His Cys Val Asn Leu Tyr Lys
1490 1495 1500

Ser Leu Ser Glu Val Lys Ser Glu Val Glu Met Val Ile Lys Thr
1505 1510 1515

Gly Arg Gln Ile Val Gln Lys Lys Gln Thr Glu Asn Pro Lys Glu
1520 1525 1530

Leu Asp Glu Arg Val Thr Ala Leu Lys Leu His Tyr Asn Glu Leu
1535 1540 1545

Gly Ala Lys Val Thr Glu Arg Lys Gln Gln Leu Glu Lys Cys Leu
1550 1555 1560

Lys Leu Ser Arg Lys Met Arg Lys Glu Met Asn Val Leu Thr Glu
1565 1570 1575

Trp Leu Ala Ala Thr Asp Thr Glu Leu Thr Lys Arg Ser Ala Val

-continued

```
    1580                1585                1590

Glu Gly  Met Pro Ser Asn Leu  Asp Ser Glu Val Ala  Trp Gly Lys
    1595                1600                1605

Ala Thr  Gln Lys Glu Ile Glu  Lys Gln Lys Ala His  Leu Lys Ser
    1610                1615                1620

Val Thr  Glu Leu Gly Asp Ser  Leu Lys Thr Val Leu  Gly Lys Lys
    1625                1630                1635

Glu Thr  Leu Val Glu Asp Lys  Leu Thr Leu Leu Asn  Ser Asn Trp
    1640                1645                1650

Ile Ala  Val Thr Ser Arg Val  Glu Glu Trp Leu Asn  Leu Leu Leu
    1655                1660                1665

Glu Tyr  Gln Lys His Met Glu  Ser Phe Asp Gln Asn  Val Glu His
    1670                1675                1680

Ile Thr  Lys Trp Ile Ile His  Thr Asp Glu Leu Leu  Asp Glu Ser
    1685                1690                1695

Glu Lys  Arg Lys Pro Gln Gln  Lys Glu Asp Ile Leu  Lys Arg Leu
    1700                1705                1710

Lys Ala  Glu Met Asn Asp Ile  Arg Pro Lys Val Asp  Ala Thr Arg
    1715                1720                1725

Asp Gln  Ala Ala Lys Leu Met  Ala Asn Arg Gly Asp  Tyr Cys Arg
    1730                1735                1740

Lys Ile  Val Glu Pro Gln Ile  Ser Glu Leu Asn Arg  Arg Phe Ala
    1745                1750                1755

Ala Ile  Ser His Arg Ile Lys  Thr Gly Lys Ala Ser  Ile Pro Leu
    1760                1765                1770

Lys Glu  Leu Glu Gln Phe Asn  Ser Asp Ile Gln Lys  Leu Leu Glu
    1775                1780                1785

Pro Leu  Glu Ala Glu Ile Gln  Gln Gly Val Asn Leu  Lys Glu Glu
    1790                1795                1800

Asp Phe  Asn Lys Asp Met Ser  Glu Asp Asn Glu Gly  Thr Val Asn
    1805                1810                1815

Glu Leu  Leu Gln Arg Gly Asp  Asn Leu Gln Gln Arg  Ile Thr Asp
    1820                1825                1830

Glu Arg  Lys Arg Glu Glu Ile  Lys Leu Lys Gln Gln  Leu Leu Gln
    1835                1840                1845

Thr Lys  His Asn Ala Leu Lys  Asp Leu Arg Ser Gln  Arg Arg Lys
    1850                1855                1860

Lys Ala  Leu Glu Ile Ser His  Gln Trp Tyr Gln Tyr  Lys Ser Gln
    1865                1870                1875

Ala Asp  Asp Leu Leu Lys Cys  Leu Asp Glu Ile Glu  Lys Lys Leu
    1880                1885                1890

Ala Ser  Leu Pro Glu Pro Arg  Asp Glu Arg Lys Ile  Lys Glu Ile
    1895                1900                1905

Asp Arg  Glu Leu Gln Lys Lys  Lys Glu Glu Leu Asn  Ala Val Arg
    1910                1915                1920

Arg Gln  Ala Glu Ser Leu Ser  Glu Asn Gly Ala Ala  Met Ala Val
    1925                1930                1935

Glu Pro  Thr Gln Ile Gln Leu  Ser Lys Arg Trp Arg  Glu Ile Glu
    1940                1945                1950

Ser Asn  Phe Ala Gln Phe Arg  Arg Leu Asn Phe Ala  Gln Ile His
    1955                1960                1965

Thr Leu  His Glu Glu Thr Met  Val Val Thr Thr Glu  Asp Met Pro
    1970                1975                1980
```

-continued

```
Leu Asp  Val Ser Tyr Val Pro  Ser Thr Tyr Leu Thr  Glu Ile Ser
    1985                 1990                 1995

His Ile  Leu Gln Ala Leu Ser  Glu Val Glu Gln Leu  Leu Asn Ala
    2000                 2005                 2010

Pro Glu  Leu Asn Ala Lys Asp  Phe Glu Asp Leu Phe  Lys Gln Glu
    2015                 2020                 2025

Glu Ser  Leu Lys Asn Ile Lys  Glu Asn Leu Gln Gln  Ile Ser Gly
    2030                 2035                 2040

Arg Ile  Asp Val Ile His Lys  Lys Lys Thr Ala Ala  Leu Gln Ser
    2045                 2050                 2055

Ala Thr  Pro Met Glu Arg Val  Lys Leu Gln Glu Ala  Val Ser Gln
    2060                 2065                 2070

Met Asp  Phe His Trp Glu Lys  Leu Asn Arg Met Tyr  Lys Glu Arg
    2075                 2080                 2085

Gln Gly  Arg Phe Asp Arg Ser  Val Glu Lys Trp Arg  His Phe His
    2090                 2095                 2100

Tyr Asp  Met Lys Val Phe Asn  Gln Trp Leu Asn Asp  Val Glu Gln
    2105                 2110                 2115

Phe Phe  Lys Lys Thr Gln Asn  Pro Glu Asn Trp Glu  His Ala Lys
    2120                 2125                 2130

Tyr Lys  Trp Tyr Leu Lys Glu  Leu Gln Asp Gly Ile  Gly Gln Arg
    2135                 2140                 2145

Gln Ala  Val Val Arg Thr Leu  Asn Ala Thr Gly Glu  Glu Ile Ile
    2150                 2155                 2160

Gln Gln  Ser Ser Lys Thr Asp  Ala Asn Ile Leu Gln  Glu Lys Leu
    2165                 2170                 2175

Gly Ser  Leu Ser Leu Arg Trp  His Glu Val Cys Lys  Glu Leu Ala
    2180                 2185                 2190

Glu Arg  Arg Lys Arg Val Glu  Glu Gln Lys Asn Val  Phe Ser Glu
    2195                 2200                 2205

Phe Gln  Arg Asp Leu Asn Glu  Phe Val Ser Trp Leu  Glu Glu Ala
    2210                 2215                 2220

Asp Asn  Ile Ala Thr Thr Pro  Pro Gly Asp Glu Glu  Gln Leu Lys
    2225                 2230                 2235

Glu Lys  Leu Glu Gln Val Lys  Leu Leu Thr Glu Glu  Leu Pro Leu
    2240                 2245                 2250

Arg Gln  Gly Ile Leu Lys Gln  Leu Asn Glu Thr Gly  Gly Ala Val
    2255                 2260                 2265

Leu Val  Ser Ala Pro Ile Arg  Pro Glu Glu Gln Asp  Lys Leu Glu
    2270                 2275                 2280

Lys Lys  Leu Lys Gln Thr Asn  Leu Gln Trp Ile Lys  Val Ser Arg
    2285                 2290                 2295

Ala Leu  Pro Glu Lys Gln Gly  Glu Leu Glu Val His  Ile Lys Asp
    2300                 2305                 2310

Phe Arg  Gln Phe Glu Glu Gln  Leu Asp His Leu Leu  Leu Trp Leu
    2315                 2320                 2325

Ser Pro  Ile Arg Asn Gln Leu  Glu Ile Tyr Asn Gln  Pro Ser Gln
    2330                 2335                 2340

Pro Gly  Pro Phe Asp Leu Lys  Glu Thr Glu Val Thr  Val Gln Ala
    2345                 2350                 2355

Lys Gln  Pro Asp Val Glu Arg  Leu Leu Ser Lys Gly  Gln His Leu
    2360                 2365                 2370
```

-continued

```
Tyr Lys  Glu Lys Pro Ser Thr  Gln Pro Val Lys Arg  Lys Leu Glu
    2375                 2380                 2385

Asp Leu  Arg Ser Glu Trp Glu  Ala Val Asn His Leu  Leu Trp Glu
    2390                 2395                 2400

Leu Arg  Thr Lys Gln Pro Asp  Arg Ala Pro Gly Leu  Ser Thr Thr
    2405                 2410                 2415

Gly Ala  Ser Ala Ser Gln Thr  Val Thr Val Val Thr  Gln Pro Val
    2420                 2425                 2430

Asp Thr  Lys Glu Thr Val Ile  Ser Lys Leu Glu Met  Pro Ser Ser
    2435                 2440                 2445

Leu Leu  Leu Glu Val Pro Ala  Leu Ala Asp Phe Asn  Arg Ala Trp
    2450                 2455                 2460

Thr Glu  Leu Thr Asp Trp Leu  Ser Leu Leu Asp Arg  Val Ile Lys
    2465                 2470                 2475

Ser Gln  Arg Val Met Val Gly  Asp Leu Glu Asp Ile  Asn Glu Met
    2480                 2485                 2490

Ile Ile  Lys Gln Lys Leu Val  Glu Ser Met Met Asn  Ser His Leu
    2495                 2500                 2505

Gln Gly  Ala Thr Leu Gln Asp  Leu Glu Gln Arg Arg  Pro Gln Leu
    2510                 2515                 2520

Glu Glu  Leu Ile Thr Ala Ala  Gln Asn Leu Lys Asn  Lys Thr Ser
    2525                 2530                 2535

Asn Gln  Glu Ala Arg Thr Ile  Ile Thr Asp Arg Ile  Glu Arg Ile
    2540                 2545                 2550

Gln Ile  Gln Trp Asp Glu Val  Gln Glu Gln Leu Gln  Asn Arg Arg
    2555                 2560                 2565

Gln Gln  Leu Asn Glu Met Leu  Lys Asp Ser Thr Gln  Trp Leu Glu
    2570                 2575                 2580

Ala Lys  Glu Glu Ala Glu Gln  Val Ile Gly Gln Ala  Arg Gly Lys
    2585                 2590                 2595

Leu Asp  Ser Trp Lys Glu Gly  Pro His Thr Met Asp  Ala Ile Gln
    2600                 2605                 2610

Lys Lys  Ile Thr Glu Thr Lys  Gln Leu Ala Lys Asp  Leu Arg Gln
    2615                 2620                 2625

Arg Gln  Ile Asn Val Asp Val  Ala Asn Asp Leu Ala  Leu Lys Leu
    2630                 2635                 2640

Leu Arg  Asp Tyr Ser Ala Asp  Asp Thr Arg Lys Val  His Met Ile
    2645                 2650                 2655

Thr Glu  Asn Ile Asn Thr Ser  Trp Gly Asn Ile Leu  Lys Arg Val
    2660                 2665                 2670

Ser Glu  Arg Glu Ala Ala Leu  Glu Glu Thr Gln Arg  Leu Leu Gln
    2675                 2680                 2685

Gln Phe  Pro Leu Asp Leu Glu  Lys Phe Leu Ala Trp  Ile Thr Glu
    2690                 2695                 2700

Ala Glu  Thr Thr Ala Asn Val  Leu Gln Asp Ala Ser  Arg Lys Glu
    2705                 2710                 2715

Lys Leu  Leu Glu Asp Ser Arg  Gly Val Arg Glu Leu  Met Lys Pro
    2720                 2725                 2730

Trp Gln  Asp Leu Gln Gly Glu  Ile Glu Ala His Thr  Asp Ile Tyr
    2735                 2740                 2745

His Asn  Leu Asp Glu Asn Gly  Gln Lys Ile Leu Arg  Ser Leu Glu
    2750                 2755                 2760

Gly Ser  Asp Glu Ala Pro Leu  Leu Gln Arg Arg Leu  Asp Asn Met
```

-continued 2765 2770 2775

Asn Phe Lys Trp Ser Glu Leu Arg Lys Lys Ser Leu Asn Ile Arg
2780 2785 2790

Ser His Leu Glu Val Ser Ser Asp Gln Trp Lys Arg Leu His Leu
2795 2800 2805

Ser Leu Gln Glu Leu Leu Val Trp Leu Gln Leu Lys Asp Asp Glu
2810 2815 2820

Leu Ser Arg Gln Ala Pro Ile Gly Gly Asp Phe Pro Ala Val Gln
2825 2830 2835

Lys Gln Asn Asp Val His Arg Ala Phe Lys Arg Glu Leu Lys Thr
2840 2845 2850

Lys Glu Pro Val Ile Met Ser Thr Leu Glu Thr Val Arg Ile Phe
2855 2860 2865

Leu Thr Glu Gln Pro Leu Glu Gly Leu Glu Lys Leu Tyr Gln Glu
2870 2875 2880

Pro Arg Glu Leu Pro Pro Glu Glu Arg Ala Gln Asn Val Thr Arg
2885 2890 2895

Leu Leu Arg Lys Gln Ala Glu Glu Val Asn Thr Glu Trp Asp Lys
2900 2905 2910

Leu Asn Leu His Ser Ala Asp Trp Gln Arg Lys Ile Asp Glu Ala
2915 2920 2925

Leu Glu Arg Leu Gln Glu Leu Gln Glu Ala Ala Asp Glu Leu Asp
2930 2935 2940

Leu Lys Leu Arg Gln Ala Glu Val Ile Lys Gly Ser Trp Gln Pro
2945 2950 2955

Val Gly Asp Leu Leu Ile Asp Ser Leu Gln Asp His Leu Glu Lys
2960 2965 2970

Val Lys Ala Leu Arg Gly Glu Ile Ala Pro Leu Lys Glu Asn Val
2975 2980 2985

Asn His Val Asn Asp Leu Ala His His Leu Thr Thr Leu Gly Ile
2990 2995 3000

Gln Leu Ser Pro Tyr Asn Leu Ser Ile Leu Glu Asp Leu Asn Thr
3005 3010 3015

Arg Trp Arg Leu Leu Gln Val Ala Val Glu Asp Arg Val Arg Gln
3020 3025 3030

Leu His Glu Ala His Arg Asp Phe Gly Pro Ala Ser Gln His Phe
3035 3040 3045

Leu Ser Thr Ser Val Gln Gly Pro Trp Glu Arg Ala Ile Ser Pro
3050 3055 3060

Asn Lys Val Pro Tyr Tyr Ile Asn His Glu Thr Gln Thr Thr Cys
3065 3070 3075

Trp Asp His Pro Lys Met Thr Glu Leu Tyr Gln Ser Leu Ala Asp
3080 3085 3090

Leu Asn Asn Val Arg Phe Ser Ala Tyr Arg Thr Ala Met Lys Leu
3095 3100 3105

Arg Arg Leu Gln Lys Ala Leu Cys Leu Asp Leu Leu Ser Leu Ser
3110 3115 3120

Ala Ala Cys Asp Ala Leu Asp Gln His Asn Leu Lys Gln Asn Asp
3125 3130 3135

Gln Pro Met Asp Ile Leu Gln Ile Ile Asn Cys Leu Thr Thr Ile
3140 3145 3150

Tyr Asp Arg Leu Glu Gln Glu His Asn Asn Leu Val Asn Val Pro
3155 3160 3165

Leu Cys Val Asp Met Cys Leu Asn Trp Leu Leu Asn Val Tyr Asp
3170 3175 3180

Thr Gly Arg Thr Gly Arg Ile Arg Val Leu Ser Phe Lys Thr Gly
3185 3190 3195

Ile Ile Ser Leu Cys Lys Ala His Leu Glu Asp Lys Tyr Arg Tyr
3200 3205 3210

Leu Phe Lys Gln Val Ala Ser Ser Thr Gly Phe Cys Asp Gln Arg
3215 3220 3225

Arg Leu Gly Leu Leu Leu His Asp Ser Ile Gln Ile Pro Arg Gln
3230 3235 3240

Leu Gly Glu Val Ala Ser Phe Gly Gly Ser Asn Ile Glu Pro Ser
3245 3250 3255

Val Arg Ser Cys Phe Gln Phe Ala Asn Asn Lys Pro Glu Ile Glu
3260 3265 3270

Ala Ala Leu Phe Leu Asp Trp Met Arg Leu Glu Pro Gln Ser Met
3275 3280 3285

Val Trp Leu Pro Val Leu His Arg Val Ala Ala Ala Glu Thr Ala
3290 3295 3300

Lys His Gln Ala Lys Cys Asn Ile Cys Lys Glu Cys Pro Ile Ile
3305 3310 3315

Gly Phe Arg Tyr Arg Ser Leu Lys His Phe Asn Tyr Asp Ile Cys
3320 3325 3330

Gln Ser Cys Phe Phe Ser Gly Arg Val Ala Lys Gly His Lys Met
3335 3340 3345

His Tyr Pro Met Val Glu Tyr Cys Thr Pro Thr Thr Ser Gly Glu
3350 3355 3360

Asp Val Arg Asp Phe Ala Lys Val Leu Lys Asn Lys Phe Arg Thr
3365 3370 3375

Lys Arg Tyr Phe Ala Lys His Pro Arg Met Gly Tyr Leu Pro Val
3380 3385 3390

Gln Thr Val Leu Glu Gly Asp Asn Met Glu Thr Pro Val Thr Leu
3395 3400 3405

Ile Asn Phe Trp Pro Val Asp Ser Ala Pro Ala Ser Ser Pro Gln
3410 3415 3420

Leu Ser His Asp Asp Thr His Ser Arg Ile Glu His Tyr Ala Ser
3425 3430 3435

Arg Leu Ala Glu Met Glu Asn Ser Asn Gly Ser Tyr Leu Asn Asp
3440 3445 3450

Ser Ile Ser Pro Asn Glu Ser Ile Asp Asp Glu His Leu Leu Ile
3455 3460 3465

Gln His Tyr Cys Gln Ser Leu Asn Gln Asp Ser Pro Leu Ser Gln
3470 3475 3480

Pro Arg Ser Pro Ala Gln Ile Leu Ile Ser Leu Glu Ser Glu Glu
3485 3490 3495

Arg Gly Glu Leu Glu Arg Ile Leu Ala Asp Leu Glu Glu Glu Asn
3500 3505 3510

Arg Asn Leu Gln Ala Glu Tyr Asp Arg Leu Lys Gln Gln His Glu
3515 3520 3525

His Lys Gly Leu Ser Pro Leu Pro Ser Pro Pro Glu Met Met Pro
3530 3535 3540

Thr Ser Pro Gln Ser Pro Arg Asp Ala Glu Leu Ile Ala Glu Ala
3545 3550 3555

-continued

```
Lys Leu  Leu Arg Gln His Lys  Gly Arg Leu Glu Ala  Arg Met Gln
    3560                 3565                 3570

Ile Leu  Glu Asp His Asn Lys  Gln Leu Glu Ser Gln  Leu His Arg
    3575                 3580                 3585

Leu Arg  Gln Leu Leu Glu Gln  Pro Gln Ala Glu Ala  Lys Val Asn
    3590                 3595                 3600

Gly Thr  Thr Val Ser Ser Pro  Ser Thr Ser Leu Gln  Arg Ser Asp
    3605                 3610                 3615

Ser Ser  Gln Pro Met Leu Leu  Arg Val Val Gly Ser  Gln Thr Ser
    3620                 3625                 3630

Glu Ser  Met Gly Glu Glu Asp  Leu Leu Ser Pro Pro  Gln Asp Thr
    3635                 3640                 3645

Ser Thr  Gly Leu Glu Glu Val  Met Glu Gln Leu Asn  Asn Ser Phe
    3650                 3655                 3660

Pro Ser  Ser Arg Gly His Asn  Val Gly Ser Leu Phe  His Met Ala
    3665                 3670                 3675

Asp Asp  Leu Gly Arg Ala Met  Glu Ser Leu Val Ser  Val Met Ile
    3680                 3685                 3690

Asp Glu  Glu Gly Ala Glu
    3695
```

<210> SEQ ID NO 8
<211> LENGTH: 3677
<212> TYPE: PRT
<213> ORGANISM: Oryctolagus cuniculus
<220> FEATURE:
<221> NAME/KEY: misc_feature
<222> LOCATION: (2570)..(2570)
<223> OTHER INFORMATION: Xaa can be any naturally occurring amino acid
<220> FEATURE:
<221> NAME/KEY: misc_feature
<222> LOCATION: (2597)..(2597)
<223> OTHER INFORMATION: Xaa can be any naturally occurring amino acid

<400> SEQUENCE: 8

```
Met Leu Trp Trp Glu Glu Val Glu Asp Cys Tyr Glu Arg Glu Asp Val
1               5                   10                  15

Gln Lys Lys Thr Phe Thr Lys Trp Ile Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Gln Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Lys Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Ser Gln Val Asn Val Ile Asn Phe Thr
145                 150                 155                 160

Thr Ser Trp Ser Asp Gly Leu Ala Leu Asn Ala Leu Ile His Ser His
                165                 170                 175
```

-continued

```
Arg Pro Asp Leu Phe Asp Trp Asn Ser Val Val Cys Gln Gln Ser Ala
            180                 185                 190

Thr Gln Arg Leu Glu His Ala Phe Asn Ile Ala Lys Cys Gln Leu Gly
        195                 200                 205

Ile Glu Lys Leu Leu Asp Pro Glu Asp Val Ala Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Leu Leu Pro Arg
                245                 250                 255

Pro Ser Lys Val Thr Arg Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Ser Thr Ser Asp Pro Thr Arg Ser Pro Phe Pro Ser Gln
305                 310                 315                 320

His Leu Glu Ala Pro Gly Asp Lys Ser Phe Gly Ser Ser Leu Met Glu
                325                 330                 335

Thr Glu Val Ser Leu Asp Ser Tyr Gln Thr Ala Leu Glu Glu Val Leu
            340                 345                 350

Ser Trp Leu Leu Ser Ala Glu Asp Thr Leu Gln Ala Gln Lys Glu Ile
        355                 360                 365

Ser Ser Asp Val Glu Glu Val Lys Glu Gln Phe His Thr His Glu Gly
    370                 375                 380

Tyr Met Met Asp Leu Thr Ser His Gln Gly Arg Val Gly Asn Val Leu
385                 390                 395                 400

Gln Leu Gly Ser Gln Leu Ile Arg Thr Gly Lys Leu Ser Glu Glu Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Lys Val
        435                 440                 445

Leu Met Asp Leu Gln Asn Gln Lys Leu Lys Glu Leu Asn Asp Trp Leu
    450                 455                 460

Thr Lys Thr Glu Glu Arg Thr Arg Lys Met Glu Glu Glu Pro Leu Gly
465                 470                 475                 480

Pro Asp Leu Glu Asp Leu Lys Arg Gln Val Gln Gln His Lys Val Leu
                485                 490                 495

Gln Glu Asp Leu Glu Gln Glu Gln Val Arg Val Asn Ser Leu Thr His
            500                 505                 510

Met Val Val Val Val Asp Glu Ser Ser Gly Glu His Ala Thr Ala Ala
        515                 520                 525

Leu Glu Glu Gln Leu Lys Val Leu Gly Asp Arg Trp Ala Asn Ile Cys
    530                 535                 540

Arg Trp Thr Glu Asp Arg Trp Val Leu Leu Gln Asp Ile Leu Leu Lys
545                 550                 555                 560

Trp Gln Arg Phe Thr Glu Glu Gln Cys Leu Phe Ser Thr Trp Leu Ser
                565                 570                 575

Glu Lys Glu Asp Ala Val Asn Lys Ile His Thr Thr Gly Phe Lys Asp
            580                 585                 590

Gln Asn Glu Met Leu Ser Ser Leu His Lys Leu Thr Val Leu Lys Thr
```

-continued

```
        595                 600                 605

Asp Leu Glu Lys Lys Lys Gln Ser Met Asp Lys Leu Ser Ser Leu Asn
    610                 615                 620

Gln Ala Leu Leu Ser Thr Leu Lys Asn Lys Ser Val Thr Gln Lys Met
625                 630                 635                 640

Glu Ala Trp Leu Glu Asn Phe Ala Leu Arg Trp Asp Asn Leu Val Gln
                645                 650                 655

Lys Leu Glu Lys Ser Ser Ala Gln Ile Ser Gln Ala Val Thr Thr Thr
            660                 665                 670

Gln Pro Ser Leu Thr Gln Thr Thr Val Met Glu Thr Val Thr Met Val
        675                 680                 685

Thr Thr Arg Glu Gln Ile Leu Val Lys His Ala Gln Glu Glu Leu Pro
    690                 695                 700

Pro Pro Pro Pro Gln Lys Lys Arg Gln Ile Ile Val Asp Ser Glu Ile
705                 710                 715                 720

Arg Lys Arg Leu Asp Val Asp Ile Thr Glu Leu His Ser Trp Ile Thr
                725                 730                 735

Arg Ser Glu Ala Val Leu Gln Ser Pro Glu Phe Ala Ile Tyr Arg Lys
            740                 745                 750

Glu Gly Asn Phe Ser Asp Leu Lys Glu Lys Val Asn Ala Ile Glu Arg
        755                 760                 765

Glu Lys Ala Glu Lys Phe Arg Lys Leu Gln Asp Ala Ser Arg Ser Ala
    770                 775                 780

Gln Ala Leu Val Glu Gln Met Val Asn Glu Gly Val Asn Ala Asp Ser
785                 790                 795                 800

Ile Lys Gln Ala Leu Glu Gln Leu Asn Ser Arg Trp Ile Glu Phe Cys
                805                 810                 815

Gln Leu Leu Ser Glu Arg Leu His Trp Leu Glu Tyr Gln Asn Ser Ile
            820                 825                 830

Ile Thr Phe Tyr Asn Gln Leu Gln Gln Leu Glu Gln Met Ile Thr Thr
        835                 840                 845

Ala Glu Asn Trp Leu Lys Thr Gln Pro Thr Thr Ala Ser Glu Pro Thr
    850                 855                 860

Ala Ile Lys Ser Gln Leu Lys Met Cys Lys Asp Glu Val Asn Arg Leu
865                 870                 875                 880

Ser Ala Leu Gln Pro Gln Ile Glu Arg Leu Lys Ile Gln Ser Thr Ala
                885                 890                 895

Leu Lys Glu Lys Gly Gln Gly Pro Met Phe Leu Asp Ala Asp Phe Val
            900                 905                 910

Ala Phe Thr Asn His Phe Asn Gln Val Phe Ala Asp Ala Gln Ala Arg
        915                 920                 925

Glu Lys Glu Leu Gln Thr Ile Phe Asp Thr Leu Pro Pro Thr Arg Tyr
    930                 935                 940

Gln Glu Thr Ile Ser Thr Ile Arg Thr Trp Ile Gln Gln Ser Glu Pro
945                 950                 955                 960

Lys Leu Ser Ile Pro Gln Leu Ser Val Thr Glu Tyr Glu Ile Met Glu
                965                 970                 975

Gln Arg Leu Gly Glu Leu Gln Ala Leu Gln Ser Ser Leu Gln Glu Gln
            980                 985                 990

Gln Ser Gly Leu Thr Tyr Leu Ser  Thr Thr Val Lys Glu  Met Ala Lys
        995                 1000                 1005

Lys Ala  Pro Ser Glu Ile Ser  Arg Lys Tyr Gln Ser  Glu Phe Glu
    1010                 1015                 1020
```

```
Glu Ile  Glu Gly His Trp Lys  Lys Leu Ser Tyr Gln  Leu Val Asp
    1025                 1030                 1035

His Cys  Gln Lys Leu Glu Glu  Gln Met Asn Lys Leu  Arg Lys Ile
    1040                 1045                 1050

Gln Asn  His Ile Lys Thr Leu  Lys Lys Trp Met Ala  Glu Val Asp
    1055                 1060                 1065

Val Phe  Leu Lys Glu Glu Trp  Pro Ala Leu Gly Asp  Ser Glu Ile
    1070                 1075                 1080

Leu Lys  Lys Gln Leu Lys Gln  Cys Arg Leu Leu Val  Asn Asp Ile
    1085                 1090                 1095

Gln Thr  Ile Gln Pro Ser Leu  Asn Ser Val Asn Glu  Ser Gly Gln
    1100                 1105                 1110

Lys Ile  Lys Asn Glu Ala Glu  Pro Glu Phe Ala Ser  Arg Leu Glu
    1115                 1120                 1125

Thr Glu  Leu Arg Glu Leu Asn  Ser Gln Trp Asp His  Met Cys Arg
    1130                 1135                 1140

Gln Val  Tyr Thr Arg Lys Asp  Ala Leu Lys Ala Gly  Leu Asp Lys
    1145                 1150                 1155

Thr Leu  Ser Leu Gln Lys Asp  Leu Ser Glu Met His  Glu Trp Met
    1160                 1165                 1170

Thr Gln  Ala Glu Glu Glu Tyr  Leu Glu Arg Asp Phe  Glu Tyr Lys
    1175                 1180                 1185

Thr Pro  Asp Glu Leu Gln Thr  Ala Val Glu Glu Met  Lys Arg Ala
    1190                 1195                 1200

Lys Glu  Glu Ala Gln Gln Lys  Glu Ser Lys Val Lys  Leu Leu Thr
    1205                 1210                 1215

Glu Ser  Val Asn Ser Val Ile  Ala Gln Ala Pro Pro  Ala Ala Gln
    1220                 1225                 1230

Glu Ala  Leu Lys Lys Glu Leu  Asp Thr Leu Thr Thr  Asn Tyr Gln
    1235                 1240                 1245

Trp Leu  Cys Thr Arg Leu Asn  Gly Lys Cys Lys Thr  Leu Glu Glu
    1250                 1255                 1260

Val Trp  Ala Cys Trp His Glu  Leu Leu Ser Tyr Leu  Glu Lys Ala
    1265                 1270                 1275

Asn Lys  Trp Leu Asn Glu Val  Glu Val Lys Leu Lys  Thr Thr Glu
    1280                 1285                 1290

Thr Leu  Pro Gly Gly Ala Glu  Glu Ile Ser Glu Val  Leu Asp Ser
    1295                 1300                 1305

Leu Glu  Asn Leu Met Gln His  Ser Glu Asp Asn Pro  Asn Gln Ile
    1310                 1315                 1320

Arg Ile  Leu Ala Gln Thr Leu  Thr Asp Gly Gly Val  Met Asp Glu
    1325                 1330                 1335

Leu Ile  Asn Glu Glu Leu Glu  Thr Phe Asn Ser Arg  Trp Arg Glu
    1340                 1345                 1350

Leu His  Glu Glu Ala Val Arg  Arg Gln Lys Leu Leu  Glu Gln Ser
    1355                 1360                 1365

Ile Gln  Ser Ala Gln Glu Ile  Glu Lys Ser Leu His  Leu Ile Gln
    1370                 1375                 1380

Glu Ser  Leu Ala Phe Ile Asp  Lys Gln Leu Ala Ala  Tyr Ile Ala
    1385                 1390                 1395

Asp Lys  Val Asp Ala Ala Gln  Met Pro Gln Glu Ala  Gln Lys Ile
    1400                 1405                 1410
```

-continued

```
Gln Ser  Asp Leu Thr Ser His  Glu Ile Ser Leu Glu  Glu Met Lys
    1415                 1420                 1425

Lys His  Asn Gln Gly Lys Glu  Ala Ala Gln Arg Val  Leu Ser Gln
    1430                 1435                 1440

Ile Asp  Val Ala Gln Lys Lys  Leu Gln Asp Val Ser  Met Lys Phe
    1445                 1450                 1455

Arg Leu  Phe Gln Lys Pro Ala  Asn Phe Glu Gln Arg  Leu Glu Glu
    1460                 1465                 1470

Ser Lys  Met Ile Leu Asp Glu  Val Lys Met His Leu  Pro Ala Leu
    1475                 1480                 1485

Glu Thr  Lys Ser Val Glu Gln  Glu Val Val Gln Ser  Gln Leu Asn
    1490                 1495                 1500

His Cys  Val Asn Leu Tyr Lys  Ser Leu Ser Glu Val  Lys Ser Glu
    1505                 1510                 1515

Val Glu  Met Val Ile Lys Thr  Gly Arg Gln Ile Val  Gln Lys Lys
    1520                 1525                 1530

Gln Thr  Glu Asn Pro Lys Glu  Leu Asp Glu Arg Val  Thr Ala Leu
    1535                 1540                 1545

Lys Leu  His Tyr Asn Glu Leu  Gly Ala Lys Val Thr  Glu Arg Lys
    1550                 1555                 1560

Gln Gln  Leu Glu Lys Cys Leu  Lys Leu Ser Arg Lys  Met Arg Lys
    1565                 1570                 1575

Glu Met  Asn Ala Leu Thr Glu  Trp Leu Ala Ala Thr  Asp Met Glu
    1580                 1585                 1590

Leu Thr  Lys Arg Ser Ala Val  Glu Gly Met Pro Ser  Asn Leu Asp
    1595                 1600                 1605

Ala Glu  Ile Ala Trp Gly Lys  Ala Thr Gln Lys Glu  Val Glu Lys
    1610                 1615                 1620

Gln Lys  Ala His Leu Lys Ser  Val Ile Glu Leu Gly  Glu Ala Leu
    1625                 1630                 1635

Lys Thr  Val Leu Gly Lys Lys  Glu Thr Leu Val Glu  Asp Lys Leu
    1640                 1645                 1650

Ser Leu  Leu Asn Ser Asn Trp  Val Ala Val Thr Ser  Arg Ala Glu
    1655                 1660                 1665

Glu Trp  Leu Asn Leu Leu Leu  Glu Tyr Gln Lys His  Met Glu Thr
    1670                 1675                 1680

Phe Asp  Gln Asn Val Asp His  Ile Thr Lys Trp Ile  Ile Gln Ala
    1685                 1690                 1695

Asp Thr  Leu Leu Asp Glu Ser  Glu Lys Lys Lys Pro  Gln Gln Lys
    1700                 1705                 1710

Glu Asp  Val Leu Lys Arg Leu  Lys Ala Glu Met Asn  Asp Ile Arg
    1715                 1720                 1725

Pro Lys  Val Asp Ser Ile Arg  Asp Gln Ala Ala Asn  Leu Met Ala
    1730                 1735                 1740

Asn Arg  Gly Asp His Cys Arg  Lys Val Val Glu Pro  Lys Ile Ser
    1745                 1750                 1755

Glu Leu  Asn His Arg Phe Ala  Ala Ile Ser His Arg  Ile Lys Thr
    1760                 1765                 1770

Gly Lys  Ala Ser Ile Pro Leu  Lys Glu Leu Glu Gln  Phe Asn Ser
    1775                 1780                 1785

Asp Ile  Gln Lys Leu Leu Glu  Pro Leu Glu Ala Glu  Ile Gln Gln
    1790                 1795                 1800

Gly Val  Asn Leu Lys Glu Glu  Asp Phe Asn Lys Asp  Met Ser Glu
```

```
    1805                1810                1815

Asp Asn  Glu Gly Thr Val Lys  Glu Leu Leu Gln Arg  Gly Asp Asn
    1820                1825                1830

Leu His  Glu Arg Ile Thr Asp  Glu Arg Lys Arg Glu  Glu Ile Lys
    1835                1840                1845

Ile Lys  Gln Gln Leu Leu Gln  Thr Lys His Asn Ala  Leu Lys Asp
    1850                1855                1860

Leu Arg  Ser Gln Arg Arg Lys  Lys Ala Leu Glu Ile  Ser His Gln
    1865                1870                1875

Trp Tyr  Gln Tyr Lys Arg Gln  Ala Asp Asp Leu Leu  Lys Cys Leu
    1880                1885                1890

Asp Asp  Ile Glu Lys Lys Leu  Ala Ser Leu Pro Asp  Pro Lys Asp
    1895                1900                1905

Glu Arg  Lys Ile Lys Glu Ile  Asp Arg Glu Leu Gln  Lys Lys Lys
    1910                1915                1920

Glu Glu  Leu Asn Ala Val His  Arg Gln Ala Glu Gly  Leu Ser Glu
    1925                1930                1935

Asp Gly  Ala Ala Met Ala Val  Glu Pro Ile Gln Ile  Gln Leu Ser
    1940                1945                1950

Lys Arg  Trp Arg Glu Ile Glu  Ser Lys Phe Ala Gln  Phe Arg Arg
    1955                1960                1965

Leu Asn  Phe Ala Gln Ile His  Thr Val Arg Glu Glu  Thr Met Val
    1970                1975                1980

Val Met  Thr Glu Asp Met Pro  Leu Glu Ile Ser Tyr  Val Pro Ser
    1985                1990                1995

Thr Tyr  Leu Thr Glu Ile Thr  His Val Ser Gln Ala  Leu Ser Glu
    2000                2005                2010

Val Asp  Gln Leu Leu Asn Ala  Pro Asp Leu Ser Ala  Lys Asp Phe
    2015                2020                2025

Glu Asp  Leu Phe Lys Gln Glu  Glu Ser Leu Lys Asn  Ile Lys Glu
    2030                2035                2040

Cys Met  Gln Gln Ile Ser Gly  Arg Ile Asp Val Ile  His Asn Lys
    2045                2050                2055

Lys Ala  Ala Ala Leu Gln Ser  Ala Thr Ala Ala Glu  Arg Val Lys
    2060                2065                2070

Leu Gln  Glu Ala Leu Ala Gln  Leu Asp Ser Gln Trp  Glu Lys Val
    2075                2080                2085

Asn Lys  Met Tyr Lys Asp Arg  Gln Gly Arg Phe Asp  Arg Ser Val
    2090                2095                2100

Glu Lys  Trp Arg Arg Phe His  Tyr Asp Met Lys Ile  Phe Asn Gln
    2105                2110                2115

Trp Leu  Thr Glu Ala Glu Gln  Phe Leu Lys Lys Thr  Gln Ile Pro
    2120                2125                2130

Glu Asn  Trp Glu His Ala Lys  Tyr Lys Trp Tyr Leu  Lys Glu Leu
    2135                2140                2145

Gln Asp  Gly Ile Gly Gln Arg  Gln Thr Val Val Arg  Thr Leu Asn
    2150                2155                2160

Thr Thr  Gly Glu Glu Ile Ile  Gln Gln Ser Ser Lys  Thr Asp Ala
    2165                2170                2175

Asn Ile  Leu Gln Glu Lys Leu  Gly Asn Leu Asn Leu  Arg Trp Gln
    2180                2185                2190

Glu Val  Cys Lys Gln Leu Ala  Glu Arg Arg Lys Arg  Leu Glu Glu
    2195                2200                2205
```

```
Gln Lys  Asn Ile Leu Ser Glu  Phe Gln Arg Asp Leu  Asn Glu Phe
    2210                 2215                 2220

Val Leu  Trp Leu Glu Glu Ala  Asp Asn Ile Thr Ser  Ile Pro Leu
    2225                 2230                 2235

Glu Pro  Gly Asn Glu Gln Gln  Leu Lys Glu Lys Leu  Glu Gln Val
    2240                 2245                 2250

Lys Leu  Leu Ala Glu Glu Leu  Pro Leu Arg Gln Gly  Ile Leu Lys
    2255                 2260                 2265

Gln Leu  Asn Glu Ala Gly Gly  Thr Ala Leu Val Ser  Ala Pro Ile
    2270                 2275                 2280

Ser Pro  Glu Glu Gln Asp Lys  Leu Glu Asn Lys Leu  Lys Gln Thr
    2285                 2290                 2295

Asn Leu  Gln Trp Ile Lys Val  Ser Lys Ala Leu Pro  Glu Lys Gln
    2300                 2305                 2310

Glu Glu  Ile Val Ala His Val  Lys Glu Leu Gly Gln  Leu Glu Glu
    2315                 2320                 2325

Gln Leu  Asn His Leu Leu Leu  Trp Leu Thr Pro Ile  Arg Asn Gln
    2330                 2335                 2340

Leu Glu  Ile Tyr Asn Gln Pro  Asn Gln Thr Gly Pro  Phe Asp Ile
    2345                 2350                 2355

Lys Glu  Thr Glu Val Ala Val  Gln Ala Lys Gln Pro  Asp Val Glu
    2360                 2365                 2370

Arg Ile  Leu Ser Lys Gly Gln  His Leu Tyr Lys Glu  Lys Pro Ala
    2375                 2380                 2385

Thr Gln  Pro Val Lys Arg Lys  Leu Glu Asp Leu Ser  Ser Glu Trp
    2390                 2395                 2400

Lys Val  Val Asn Tyr Leu Leu  Gln Glu Leu Arg Ala  Lys Arg Pro
    2405                 2410                 2415

Asp Leu  Pro Pro Gly Pro Ala  Thr Ile Gly Ala Ser  Pro Ser Gln
    2420                 2425                 2430

Thr Val  Thr Leu Val Thr Gln  Thr Val Val Thr Lys  Glu Ile Ser
    2435                 2440                 2445

Leu Ser  Glu Leu Glu Met Pro  Ser Ser Leu Leu Leu  Glu Val Pro
    2450                 2455                 2460

Ala Leu  Ala Asp Phe Asn Arg  Ala Trp Thr Glu Leu  Thr Asp Trp
    2465                 2470                 2475

Leu Ser  Leu Leu Asp Arg Val  Leu Lys Ser Gln Gln  Val Ile Val
    2480                 2485                 2490

Gly Asp  Leu Glu Asp Ile Asn  Glu Met Ile Ile Lys  Gln Lys Ala
    2495                 2500                 2505

Thr Leu  Gln Glu Leu Glu Gln  Arg Arg Pro Gln Leu  Glu Glu Leu
    2510                 2515                 2520

Ile Thr  Ala Ala Gln Asn Leu  Lys Asn Lys Thr Ser  Asn Gln Glu
    2525                 2530                 2535

Ala Arg  Thr Ile Ile Thr Asp  Arg Ile Glu Arg Ile  Gln Asn Gln
    2540                 2545                 2550

Trp Asp  Glu Val Gln Glu His  Leu Gln Asn Arg Ser  Ser Ser Leu
    2555                 2560                 2565

Asn Xaa  Met Leu Lys Asp Ser  Thr Gln Trp Leu Glu  Ala Lys Glu
    2570                 2575                 2580

Glu Leu  Ser Ser Leu Gly Gln  Ala Arg Ala Lys Leu  Ser Xaa Met
    2585                 2590                 2595
```

-continued

Glu Glu Gly Pro Tyr Pro Met Asn Ala Leu Gln Lys Lys Ile Glu
2600 2605 2610

Glu Thr Lys Gln Leu Ala Lys Asp Leu Arg Gln Trp Gln Ile Asn
2615 2620 2625

Val Asp Val Ala Asn Asp Leu Ala Leu Lys Leu Leu Arg Asp Tyr
2630 2635 2640

Ser Ala Asp Asp Thr Arg Lys Val His Met Ile Thr Glu Asn Ile
2645 2650 2655

Asn Ala Ser Trp Gly Ser Ile His Lys Arg Val Asn Glu Arg Glu
2660 2665 2670

Ala Thr Leu Glu Glu Ala Tyr Arg Leu Leu Gln Gln Phe Pro Leu
2675 2680 2685

Asp Leu Glu Lys Phe Leu Ala Trp Leu Thr Glu Ala Glu Thr Thr
2690 2695 2700

Ala Asn Val Leu Gln Asp Ala Thr His Lys Glu Arg Leu Pro Glu
2705 2710 2715

Asp Ser Lys Gly Val Arg Glu Leu Met Lys Gln Trp Gln Asp Leu
2720 2725 2730

Gln Gly Glu Ile Glu Ala His Thr Asp Ile Tyr His Asn Leu Asp
2735 2740 2745

Glu Asn Gly Gln Lys Ile Leu Arg Ser Leu Glu Gly Ser Asp Glu
2750 2755 2760

Ala Val Leu Leu Gln Arg Arg Leu Asp Asn Met Asn Phe Lys Trp
2765 2770 2775

Ser Glu Leu Arg Lys Lys Ser Leu Asn Ile Arg Ser His Leu Glu
2780 2785 2790

Ala Ser Ser Asp Gln Trp Lys Arg Leu His Leu Ser Leu Gln Glu
2795 2800 2805

Leu Leu Val Trp Leu Gln Leu Lys Asp Asp Glu Leu Asn Arg Gln
2810 2815 2820

Ala Pro Val Gly Gly Asp Phe Pro Ala Val Gln Lys Gln Asn Asp
2825 2830 2835

Val His Arg Ala Phe Lys Arg Glu Leu Lys Thr Lys Glu Pro Val
2840 2845 2850

Ile Met Ser Thr Leu Glu Thr Val Arg Ile Phe Leu Thr Glu Gln
2855 2860 2865

Pro Leu Gly Gly Leu Glu Lys Leu Tyr Gln Glu Pro Arg Glu Leu
2870 2875 2880

Pro Pro Asp Glu Arg Ala Gln Asn Val Thr Arg Leu Leu Arg Lys
2885 2890 2895

Gln Ala Glu Glu Val Asn Ala Glu Trp Glu Lys Leu Asn Leu His
2900 2905 2910

Ser Thr Asp Trp Gln Arg Lys Leu Asp Glu Ala Leu Glu Arg Leu
2915 2920 2925

Gln Glu Leu Gln Glu Ala Thr Asp Glu Leu Asp Leu Lys Leu Arg
2930 2935 2940

Gln Ala Glu Val Ile Lys Gly Ser Trp Gln Pro Val Gly Asp Leu
2945 2950 2955

Leu Ile Asp Ser Leu Gln Asp His Leu Glu Lys Val Lys Ala Leu
2960 2965 2970

Arg Gly Glu Ile Ala Pro Leu Lys Glu Asn Val Ser His Val Asn
2975 2980 2985

Asp Leu Gly Arg Gln Leu Thr Thr Leu Gly Ile Gln Leu Ser Pro

-continued

```
    2990                2995                3000

Tyr Asn Leu Ser Thr Leu Glu Asp Leu Asn Thr Arg Trp Lys Leu
    3005                3010                3015

Leu Gln Val Ala Val Glu Asp Arg Ile Arg Gln Leu His Glu Ala
    3020                3025                3030

His Arg Asp Phe Gly Pro Ala Ser Gln His Phe Leu Ser Thr Ser
    3035                3040                3045

Val Gln Gly Pro Trp Glu Arg Ala Ile Ser Pro Asn Lys Val Pro
    3050                3055                3060

Tyr Tyr Ile Asn His Glu Thr Gln Thr Thr Cys Trp Asp His Pro
    3065                3070                3075

Lys Met Thr Glu Leu Tyr Gln Ser Leu Ala Asp Leu Asn Asn Val
    3080                3085                3090

Arg Phe Ser Ala Tyr Arg Thr Ala Met Lys Leu Arg Arg Leu Gln
    3095                3100                3105

Lys Ala Leu Cys Leu Asp Leu Leu Thr Leu Ser Ala Ala Cys Asp
    3110                3115                3120

Ala Leu Asp Gln His Asn Leu Lys Gln Asn Asp Gln Pro Met Asp
    3125                3130                3135

Ile Leu Gln Ile Ile Asn Cys Leu Thr Thr Val Tyr Asp Arg Leu
    3140                3145                3150

Glu Gln Glu His Asn Asn Leu Val Asn Val Pro Leu Cys Val Asp
    3155                3160                3165

Met Cys Leu Asn Trp Leu Leu Asn Val Tyr Asp Thr Gly Arg Thr
    3170                3175                3180

Gly Arg Ile Arg Val Leu Ser Phe Lys Thr Gly Ile Ile Ser Leu
    3185                3190                3195

Cys Lys Ala His Leu Glu Asp Lys Tyr Arg Tyr Leu Phe Lys Gln
    3200                3205                3210

Val Ala Ser Ser Thr Gly Phe Cys Asp Gln Arg Arg Leu Gly Leu
    3215                3220                3225

Leu Leu His Asp Ser Ile Gln Ile Pro Arg Gln Leu Gly Glu Val
    3230                3235                3240

Ala Ser Phe Gly Gly Ser Asn Ile Glu Pro Ser Val Arg Ser Cys
    3245                3250                3255

Phe Gln Phe Ala Asn Asn Lys Pro Glu Ile Glu Ala Ala Leu Phe
    3260                3265                3270

Leu Asp Trp Met Arg Leu Glu Pro Gln Ser Met Val Trp Leu Pro
    3275                3280                3285

Val Leu His Arg Val Ala Ala Ala Glu Thr Ala Lys His Gln Ala
    3290                3295                3300

Lys Cys Asn Ile Cys Lys Glu Cys Pro Ile Ile Gly Phe Arg Tyr
    3305                3310                3315

Arg Ser Leu Lys His Phe Asn Tyr Asp Ile Cys Gln Ser Cys Phe
    3320                3325                3330

Phe Ser Gly Arg Val Ala Lys Gly His Lys Met His Tyr Pro Met
    3335                3340                3345

Val Glu Tyr Cys Thr Pro Thr Thr Ser Gly Glu Asp Val Arg Asp
    3350                3355                3360

Phe Ala Lys Val Leu Lys Asn Lys Phe Arg Thr Lys Arg Tyr Phe
    3365                3370                3375

Ala Lys His Pro Arg Met Gly Tyr Leu Pro Val Gln Thr Val Leu
    3380                3385                3390
```

-continued

```
Glu Gly  Asp Asn Met Glu Thr  Pro Val Thr Leu Ile  Asn Phe Trp
    3395                 3400                 3405

Pro Val  Asp Ser Ala Pro Ala  Ser Ser Pro Gln Leu  Ser His Asp
    3410                 3415                 3420

Asp Thr  His Ser Arg Ile Glu  His Tyr Ala Ser Arg  Leu Ala Glu
    3425                 3430                 3435

Met Glu  Asn Ser Asn Gly Ser  Tyr Leu Asn Asp Ser  Ile Ser Pro
    3440                 3445                 3450

Asn Glu  Ser Ile Asp Asp Glu  His Leu Leu Ile Gln  His Tyr Cys
    3455                 3460                 3465

Gln Ser  Leu Asn Gln Asp Ser  Pro Leu Ser Gln Pro  Arg Ser Pro
    3470                 3475                 3480

Ala Gln  Ile Leu Ile Ser Leu  Glu Ser Glu Glu Arg  Gly Glu Leu
    3485                 3490                 3495

Glu Arg  Ile Leu Ala Asp Leu  Glu Glu Glu Asn Arg  Asn Leu Gln
    3500                 3505                 3510

Ala Glu  Tyr Asp Arg Leu Lys  Gln Gln His Glu His  Lys Gly Leu
    3515                 3520                 3525

Ser Pro  Leu Pro Ser Pro Pro  Glu Met Met Pro Thr  Ser Pro Gln
    3530                 3535                 3540

Ser Pro  Arg Asp Ala Glu Leu  Ile Ala Glu Ala Lys  Leu Leu Arg
    3545                 3550                 3555

Gln His  Lys Gly Arg Leu Glu  Ala Arg Met Gln Ile  Leu Glu Asp
    3560                 3565                 3570

His Asn  Lys Gln Leu Glu Ser  Gln Leu His Arg Leu  Arg Gln Leu
    3575                 3580                 3585

Leu Glu  Gln Pro Gln Ala Glu  Ala Lys Val Asn Gly  Thr Thr Val
    3590                 3595                 3600

Ser Ser  Pro Ser Thr Ser Leu  Gln Arg Ser Asp Ser  Ser Gln Pro
    3605                 3610                 3615

Met Leu  Leu Arg Val Val Gly  Ser Gln Thr Ser Glu  Ser Met Gly
    3620                 3625                 3630

Glu Glu  Asp Leu Pro Ser Pro  Pro Gln Asp Thr Ser  Thr Gly Leu
    3635                 3640                 3645

Glu Glu  Val Met Glu Gln Leu  Asn Asn Ser Phe Pro  Ser Ser Arg
    3650                 3655                 3660

Gly Arg  Asn Thr Pro Gly Lys  Pro Met Arg Glu Asp  Thr Met
    3665                 3670                 3675
```

<210> SEQ ID NO 9
<211> LENGTH: 14
<212> TYPE: PRT
<213> ORGANISM: Artificial sequence
<220> FEATURE:
<223> OTHER INFORMATION: Synthetic

<400> SEQUENCE: 9

```
Ala Glu Glu Gln Lys Leu Ile Ser Glu Glu Asp Leu Leu Lys
1               5                   10
```

<210> SEQ ID NO 10
<211> LENGTH: 5
<212> TYPE: PRT
<213> ORGANISM: Artificial sequence
<220> FEATURE:
<223> OTHER INFORMATION: Synthetic

<400> SEQUENCE: 10

Asp Asp Ala Met His
1 5

<210> SEQ ID NO 11
<211> LENGTH: 5
<212> TYPE: PRT
<213> ORGANISM: Artificial sequence
<220> FEATURE:
<223> OTHER INFORMATION: Synthetic

<400> SEQUENCE: 11

Asp Tyr Ser Met His
1 5

<210> SEQ ID NO 12
<211> LENGTH: 5
<212> TYPE: PRT
<213> ORGANISM: Artificial sequence
<220> FEATURE:
<223> OTHER INFORMATION: Synthetic

<400> SEQUENCE: 12

Glu Tyr Thr Ile His
1 5

<210> SEQ ID NO 13
<211> LENGTH: 5
<212> TYPE: PRT
<213> ORGANISM: Artificial sequence
<220> FEATURE:
<223> OTHER INFORMATION: Synthetic

<400> SEQUENCE: 13

Asp Tyr Ser Met His
1 5

<210> SEQ ID NO 14
<211> LENGTH: 5
<212> TYPE: PRT
<213> ORGANISM: Artificial sequence
<220> FEATURE:
<223> OTHER INFORMATION: Synthetic

<400> SEQUENCE: 14

Asp Phe Ser Met His
1 5

<210> SEQ ID NO 15
<211> LENGTH: 5
<212> TYPE: PRT
<213> ORGANISM: Artificial sequence
<220> FEATURE:
<223> OTHER INFORMATION: Synthetic

<400> SEQUENCE: 15

Ala Tyr Ser Met His
1 5

<210> SEQ ID NO 16
<211> LENGTH: 5
<212> TYPE: PRT
<213> ORGANISM: Artificial sequence
<220> FEATURE:
<223> OTHER INFORMATION: Synthetic

<400> SEQUENCE: 16

Asp Tyr Ser Met His
1 5

<210> SEQ ID NO 17
<211> LENGTH: 5
<212> TYPE: PRT
<213> ORGANISM: Artificial sequence
<220> FEATURE:
<223> OTHER INFORMATION: Synthetic

<400> SEQUENCE: 17

Asp Tyr Ser Met His
1 5

<210> SEQ ID NO 18
<211> LENGTH: 17
<212> TYPE: PRT
<213> ORGANISM: Artificial sequence
<220> FEATURE:
<223> OTHER INFORMATION: Synthetic

<400> SEQUENCE: 18

Trp Ile Asn Thr Glu Thr Gly Glu Pro Thr Tyr Ala Asp Asp Phe Lys
1 5 10 15

Gly

<210> SEQ ID NO 19
<211> LENGTH: 17
<212> TYPE: PRT
<213> ORGANISM: Artificial sequence
<220> FEATURE:
<223> OTHER INFORMATION: Synthetic

<400> SEQUENCE: 19

Trp Ile Asn Thr Glu Thr Gly Glu Pro Thr Tyr Ala Asp Asp Phe Lys
1 5 10 15

Gly

<210> SEQ ID NO 20
<211> LENGTH: 17
<212> TYPE: PRT
<213> ORGANISM: Artificial sequence
<220> FEATURE:
<223> OTHER INFORMATION: Synthetic

<400> SEQUENCE: 20

Gly Ile Asn Cys Asn Ser Gly Gly Thr Ser Tyr Thr Gln Lys Phe Lys
1 5 10 15

Asp

<210> SEQ ID NO 21
<211> LENGTH: 17
<212> TYPE: PRT
<213> ORGANISM: Artificial sequence
<220> FEATURE:
<223> OTHER INFORMATION: Synthetic

<400> SEQUENCE: 21

Trp Ile Asn Thr Glu Thr Gly Glu Pro Thr Tyr Ala Asp Asp Phe Lys
1 5 10 15

Gly

<210> SEQ ID NO 22

-continued

<211> LENGTH: 17
<212> TYPE: PRT
<213> ORGANISM: Artificial sequence
<220> FEATURE:
<223> OTHER INFORMATION: Synthetic

<400> SEQUENCE: 22

Trp Ile Asn Thr Glu Thr Gly Asp Pro Thr Tyr Ala Asp Asp Phe Lys
1 5 10 15

Gly

<210> SEQ ID NO 23
<211> LENGTH: 17
<212> TYPE: PRT
<213> ORGANISM: Artificial sequence
<220> FEATURE:
<223> OTHER INFORMATION: Synthetic

<400> SEQUENCE: 23

Trp Ile Asn Thr Glu Thr Gly Glu Ala Thr Tyr Ala Asp Asp Phe Lys
1 5 10 15

Gly

<210> SEQ ID NO 24
<211> LENGTH: 17
<212> TYPE: PRT
<213> ORGANISM: Artificial sequence
<220> FEATURE:
<223> OTHER INFORMATION: Synthetic

<400> SEQUENCE: 24

Trp Ile Asn Thr Glu Thr Gly Glu Pro Thr Tyr Ala Asp Asp Phe Lys
1 5 10 15

Gly

<210> SEQ ID NO 25
<211> LENGTH: 17
<212> TYPE: PRT
<213> ORGANISM: Artificial sequence
<220> FEATURE:
<223> OTHER INFORMATION: Synthetic

<400> SEQUENCE: 25

Trp Ile Asn Thr Glu Thr Gly Glu Pro Thr Tyr Ala Asp Asp Phe Lys
1 5 10 15

Gly

<210> SEQ ID NO 26
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid

<400> SEQUENCE: 26

Xaa Leu Asp Phe
1

<210> SEQ ID NO 27
<211> LENGTH: 5
<212> TYPE: PRT

-continued

<213> ORGANISM: Artificial sequence
<220> FEATURE:
<223> OTHER INFORMATION: Synthetic

<400> SEQUENCE: 27

Gly Ala Ser Gly Tyr
1 5

<210> SEQ ID NO 28
<211> LENGTH: 11
<212> TYPE: PRT
<213> ORGANISM: Artificial sequence
<220> FEATURE:
<223> OTHER INFORMATION: Synthetic

<400> SEQUENCE: 28

Arg Phe Phe Tyr Gly Ser Ser Gln Phe Ala Tyr
1 5 10

<210> SEQ ID NO 29
<211> LENGTH: 4
<212> TYPE: PRT
<213> ORGANISM: Artificial sequence
<220> FEATURE:
<223> OTHER INFORMATION: Synthetic

<400> SEQUENCE: 29

Arg Gly Glu Phe
1

<210> SEQ ID NO 30
<211> LENGTH: 4
<212> TYPE: PRT
<213> ORGANISM: Artificial sequence
<220> FEATURE:
<223> OTHER INFORMATION: Synthetic

<400> SEQUENCE: 30

Arg Gly Asp Tyr
1

<210> SEQ ID NO 31
<211> LENGTH: 4
<212> TYPE: PRT
<213> ORGANISM: Artificial sequence
<220> FEATURE:
<223> OTHER INFORMATION: Synthetic

<400> SEQUENCE: 31

Arg Gly Asp Tyr
1

<210> SEQ ID NO 32
<211> LENGTH: 4
<212> TYPE: PRT
<213> ORGANISM: Artificial sequence
<220> FEATURE:
<223> OTHER INFORMATION: Synthetic

<400> SEQUENCE: 32

Arg Gly Asp Tyr
1

<210> SEQ ID NO 33
<211> LENGTH: 5
<212> TYPE: PRT
<213> ORGANISM: Artificial sequence
<220> FEATURE:
<223> OTHER INFORMATION: Synthetic

<400> SEQUENCE: 33

Gly Arg Ser Ala Tyr
1               5

<210> SEQ ID NO 34
<211> LENGTH: 16
<212> TYPE: PRT
<213> ORGANISM: Artificial sequence
<220> FEATURE:
<223> OTHER INFORMATION: Synthetic

<400> SEQUENCE: 34

Arg Ser Ser Gln Ser Leu Val His Ser Asn Gly Lys Thr Tyr Leu His
1               5                   10                  15

<210> SEQ ID NO 35
<211> LENGTH: 11
<212> TYPE: PRT
<213> ORGANISM: Artificial sequence
<220> FEATURE:
<223> OTHER INFORMATION: Synthetic

<400> SEQUENCE: 35

Lys Ala Ser Gln Ser Val Ser Lys Asn Val Ala
1               5                   10

<210> SEQ ID NO 36
<211> LENGTH: 15
<212> TYPE: PRT
<213> ORGANISM: Artificial sequence
<220> FEATURE:
<223> OTHER INFORMATION: Synthetic

<400> SEQUENCE: 36

Arg Ala Ser Lys Ser Val Thr Thr Ser Gly Tyr Ser Tyr Met His
1               5                   10                  15

<210> SEQ ID NO 37
<211> LENGTH: 11
<212> TYPE: PRT
<213> ORGANISM: Artificial sequence
<220> FEATURE:
<223> OTHER INFORMATION: Synthetic

<400> SEQUENCE: 37

Lys Ala Ser Gln Ser Val Asn Lys Asn Val Ala
1               5                   10

<210> SEQ ID NO 38
<211> LENGTH: 16
<212> TYPE: PRT
<213> ORGANISM: Artificial sequence
<220> FEATURE:
<223> OTHER INFORMATION: Synthetic

<400> SEQUENCE: 38

Arg Ser Ser Gln Ser Leu Val His Ser Asn Arg Asn Ile Tyr Leu His
1               5                   10                  15

<210> SEQ ID NO 39
<211> LENGTH: 16
<212> TYPE: PRT
<213> ORGANISM: Artificial sequence
<220> FEATURE:

<223> OTHER INFORMATION: Synthetic

<400> SEQUENCE: 39

Arg Ser Ser Gln Ser Leu Val Arg Ser Asn Arg Asn Ile Tyr Leu His
1 5 10 15

<210> SEQ ID NO 40
<211> LENGTH: 16
<212> TYPE: PRT
<213> ORGANISM: Artificial sequence
<220> FEATURE:
<223> OTHER INFORMATION: Synthetic

<400> SEQUENCE: 40

Arg Ser Ser Gln Ser Leu Val His Asn Asn Arg Asn Ile Tyr Leu His
1 5 10 15

<210> SEQ ID NO 41
<211> LENGTH: 11
<212> TYPE: PRT
<213> ORGANISM: Artificial sequence
<220> FEATURE:
<223> OTHER INFORMATION: Synthetic

<400> SEQUENCE: 41

Lys Ala Ser Gln Thr Val Ser Asn Asn Val Ala
1 5 10

<210> SEQ ID NO 42
<211> LENGTH: 7
<212> TYPE: PRT
<213> ORGANISM: Artificial sequence
<220> FEATURE:
<223> OTHER INFORMATION: Synthetic

<400> SEQUENCE: 42

Lys Val Ser Asn Arg Phe Ser
1 5

<210> SEQ ID NO 43
<211> LENGTH: 7
<212> TYPE: PRT
<213> ORGANISM: Artificial sequence
<220> FEATURE:
<223> OTHER INFORMATION: Synthetic

<400> SEQUENCE: 43

Ser Ser Ser Lys Arg Tyr Ser
1 5

<210> SEQ ID NO 44
<211> LENGTH: 7
<212> TYPE: PRT
<213> ORGANISM: Artificial sequence
<220> FEATURE:
<223> OTHER INFORMATION: Synthetic

<400> SEQUENCE: 44

Leu Ala Ser Asn Leu Glu Ser
1 5

<210> SEQ ID NO 45
<211> LENGTH: 7
<212> TYPE: PRT
<213> ORGANISM: Artificial sequence
<220> FEATURE:
<223> OTHER INFORMATION: Synthetic

<400> SEQUENCE: 45

Ser Ala Ser Lys Arg Tyr Thr
1 5

<210> SEQ ID NO 46
<211> LENGTH: 7
<212> TYPE: PRT
<213> ORGANISM: Artificial sequence
<220> FEATURE:
<223> OTHER INFORMATION: Synthetic

<400> SEQUENCE: 46

Lys Val Ser Asn Arg Phe Ser
1 5

<210> SEQ ID NO 47
<211> LENGTH: 7
<212> TYPE: PRT
<213> ORGANISM: Artificial sequence
<220> FEATURE:
<223> OTHER INFORMATION: Synthetic

<400> SEQUENCE: 47

Lys Val Ser Asn Arg Phe Ser
1 5

<210> SEQ ID NO 48
<211> LENGTH: 7
<212> TYPE: PRT
<213> ORGANISM: Artificial sequence
<220> FEATURE:
<223> OTHER INFORMATION: Synthetic

<400> SEQUENCE: 48

Lys Val Ser Asn Arg Phe Ser
1 5

<210> SEQ ID NO 49
<211> LENGTH: 7
<212> TYPE: PRT
<213> ORGANISM: Artificial sequence
<220> FEATURE:
<223> OTHER INFORMATION: Synthetic

<400> SEQUENCE: 49

Ser Ala Ser Asn Arg Tyr Thr
1 5

<210> SEQ ID NO 50
<211> LENGTH: 9
<212> TYPE: PRT
<213> ORGANISM: Artificial sequence
<220> FEATURE:
<223> OTHER INFORMATION: Synthetic

<400> SEQUENCE: 50

Ser Gln Ser Thr His Val Pro Trp Thr
1 5

<210> SEQ ID NO 51
<211> LENGTH: 9
<212> TYPE: PRT
<213> ORGANISM: Artificial sequence
<220> FEATURE:
<223> OTHER INFORMATION: Synthetic

<400> SEQUENCE: 51

His Gln Asp Tyr Asn Ser Pro Trp Thr
1               5

<210> SEQ ID NO 52
<211> LENGTH: 9
<212> TYPE: PRT
<213> ORGANISM: Artificial sequence
<220> FEATURE:
<223> OTHER INFORMATION: Synthetic

<400> SEQUENCE: 52

Gln His Ser Arg Glu Leu Pro Leu Thr
1               5

<210> SEQ ID NO 53
<211> LENGTH: 9
<212> TYPE: PRT
<213> ORGANISM: Artificial sequence
<220> FEATURE:
<223> OTHER INFORMATION: Synthetic

<400> SEQUENCE: 53

Leu Gln Asp Tyr Thr Ser Pro Trp Thr
1               5

<210> SEQ ID NO 54
<211> LENGTH: 9
<212> TYPE: PRT
<213> ORGANISM: Artificial sequence
<220> FEATURE:
<223> OTHER INFORMATION: Synthetic

<400> SEQUENCE: 54

Ser Gln Asp Lys Tyr Ile Pro Trp Thr
1               5

<210> SEQ ID NO 55
<211> LENGTH: 9
<212> TYPE: PRT
<213> ORGANISM: Artificial sequence
<220> FEATURE:
<223> OTHER INFORMATION: Synthetic

<400> SEQUENCE: 55

Ser Gln Asp Ser His Ile Pro Trp Thr
1               5

<210> SEQ ID NO 56
<211> LENGTH: 9
<212> TYPE: PRT
<213> ORGANISM: Artificial sequence
<220> FEATURE:
<223> OTHER INFORMATION: Synthetic

<400> SEQUENCE: 56

Ser Gln Asp Arg Tyr Ile Pro Trp Thr
1               5

<210> SEQ ID NO 57
<211> LENGTH: 9
<212> TYPE: PRT
<213> ORGANISM: Artificial sequence
<220> FEATURE:
<223> OTHER INFORMATION: Synthetic

<400> SEQUENCE: 57

-continued

```
Gln Gln Asp Tyr Ser Ser Pro Trp Thr
1               5


<210> SEQ ID NO 58
<211> LENGTH: 5
<212> TYPE: PRT
<213> ORGANISM: Artificial sequence
<220> FEATURE:
<223> OTHER INFORMATION: Synthetic

<400> SEQUENCE: 58

Thr Tyr Gly Met Ser
1               5


<210> SEQ ID NO 59
<211> LENGTH: 5
<212> TYPE: PRT
<213> ORGANISM: Artificial sequence
<220> FEATURE:
<223> OTHER INFORMATION: Synthetic

<400> SEQUENCE: 59

Thr Tyr Gly Met Thr
1               5


<210> SEQ ID NO 60
<211> LENGTH: 17
<212> TYPE: PRT
<213> ORGANISM: Artificial sequence
<220> FEATURE:
<223> OTHER INFORMATION: Synthetic

<400> SEQUENCE: 60

Trp Ile Asn Thr Ser Ser Gly Val Pro Thr Tyr Ala Asp Asp Phe Lys
1               5                   10                  15

Gly


<210> SEQ ID NO 61
<211> LENGTH: 17
<212> TYPE: PRT
<213> ORGANISM: Artificial sequence
<220> FEATURE:
<223> OTHER INFORMATION: Synthetic

<400> SEQUENCE: 61

Trp Ile Asn Thr Tyr Ser Gly Val Pro Thr Tyr Ala Asn Asp Phe Lys
1               5                   10                  15

Gly


<210> SEQ ID NO 62
<211> LENGTH: 17
<212> TYPE: PRT
<213> ORGANISM: Artificial sequence
<220> FEATURE:
<223> OTHER INFORMATION: Synthetic

<400> SEQUENCE: 62

Trp Ile Asn Thr Tyr Ser Gly Leu Pro Thr Tyr Thr Asn Asp Phe Lys
1               5                   10                  15

Gly


<210> SEQ ID NO 63
<211> LENGTH: 17
<212> TYPE: PRT
```

-continued

<213> ORGANISM: Artificial sequence
<220> FEATURE:
<223> OTHER INFORMATION: Synthetic

<400> SEQUENCE: 63

Trp Ile Asn Thr Tyr Ser Gly Leu Pro Thr Tyr Ala Asp Asp Phe Lys
1 5 10 15

Gly

<210> SEQ ID NO 64
<211> LENGTH: 17
<212> TYPE: PRT
<213> ORGANISM: Artificial sequence
<220> FEATURE:
<223> OTHER INFORMATION: Synthetic

<400> SEQUENCE: 64

Trp Ile Asn Thr Tyr Ser Gly Val Pro Thr Tyr Ala Asp Asp Phe Lys
1 5 10 15

Gly

<210> SEQ ID NO 65
<211> LENGTH: 17
<212> TYPE: PRT
<213> ORGANISM: Artificial sequence
<220> FEATURE:
<223> OTHER INFORMATION: Synthetic

<400> SEQUENCE: 65

Trp Ile Asn Thr Phe Ser Gly Val Pro Thr Tyr Thr Asp Asp Phe Lys
1 5 10 15

Gly

<210> SEQ ID NO 66
<211> LENGTH: 10
<212> TYPE: PRT
<213> ORGANISM: Artificial sequence
<220> FEATURE:
<223> OTHER INFORMATION: Synthetic

<400> SEQUENCE: 66

Pro Ile His Met Val Val Ala Glu Asp Tyr
1 5 10

<210> SEQ ID NO 67
<211> LENGTH: 10
<212> TYPE: PRT
<213> ORGANISM: Artificial sequence
<220> FEATURE:
<223> OTHER INFORMATION: Synthetic

<400> SEQUENCE: 67

Pro Ile His Lys Val Val Ala Glu Asp Tyr
1 5 10

<210> SEQ ID NO 68
<211> LENGTH: 10
<212> TYPE: PRT
<213> ORGANISM: Artificial sequence
<220> FEATURE:
<223> OTHER INFORMATION: Synthetic

<400> SEQUENCE: 68

Pro Ile Thr Thr Val Val Pro Phe Asp Tyr
1 5 10

<210> SEQ ID NO 69
<211> LENGTH: 10
<212> TYPE: PRT
<213> ORGANISM: Artificial sequence
<220> FEATURE:
<223> OTHER INFORMATION: Synthetic

<400> SEQUENCE: 69

```
Pro Ile Thr Thr Val Val Pro Phe Asp Tyr
1               5                   10
```

<210> SEQ ID NO 70
<211> LENGTH: 10
<212> TYPE: PRT
<213> ORGANISM: Artificial sequence
<220> FEATURE:
<223> OTHER INFORMATION: Synthetic

<400> SEQUENCE: 70

```
Pro Ile Thr Lys Val Val Ala Gly Asp Phe
1               5                   10
```

<210> SEQ ID NO 71
<211> LENGTH: 10
<212> TYPE: PRT
<213> ORGANISM: Artificial sequence
<220> FEATURE:
<223> OTHER INFORMATION: Synthetic

<400> SEQUENCE: 71

```
Pro Ile Thr Thr Val Val Pro Phe Asp Tyr
1               5                   10
```

<210> SEQ ID NO 72
<211> LENGTH: 17
<212> TYPE: PRT
<213> ORGANISM: Artificial sequence
<220> FEATURE:
<223> OTHER INFORMATION: Synthetic

<400> SEQUENCE: 72

```
Lys Ser Ser Gln Ile Leu Leu Tyr Gly Arg Asn Gln Lys Asn Tyr Leu
1               5                   10                  15

Ala
```

<210> SEQ ID NO 73
<211> LENGTH: 17
<212> TYPE: PRT
<213> ORGANISM: Artificial sequence
<220> FEATURE:
<223> OTHER INFORMATION: Synthetic

<400> SEQUENCE: 73

```
Arg Ser Ser Gln Ser Leu Leu Tyr Ser Gly Asn Gln Lys Asn Tyr Leu
1               5                   10                  15

Ala
```

<210> SEQ ID NO 74
<211> LENGTH: 16
<212> TYPE: PRT
<213> ORGANISM: Artificial sequence
<220> FEATURE:
<223> OTHER INFORMATION: Synthetic

<400> SEQUENCE: 74

Arg Ser Ser Gln Ser Leu Val Tyr Thr Tyr Gly Asn Thr Tyr Leu His
1 5 10 15

<210> SEQ ID NO 75
<211> LENGTH: 16
<212> TYPE: PRT
<213> ORGANISM: Artificial sequence
<220> FEATURE:
<223> OTHER INFORMATION: Synthetic

<400> SEQUENCE: 75

Arg Ser Ser Gln Ser Leu Val Tyr Asn Tyr Gly Asn Thr Tyr Leu His
1 5 10 15

<210> SEQ ID NO 76
<211> LENGTH: 17
<212> TYPE: PRT
<213> ORGANISM: Artificial sequence
<220> FEATURE:
<223> OTHER INFORMATION: Synthetic

<400> SEQUENCE: 76

Lys Ser Ser Gln Ser Leu Leu Tyr Arg Ser Asn Gln Lys Asn Tyr Leu
1 5 10 15

Ala

<210> SEQ ID NO 77
<211> LENGTH: 16
<212> TYPE: PRT
<213> ORGANISM: Artificial sequence
<220> FEATURE:
<223> OTHER INFORMATION: Synthetic

<400> SEQUENCE: 77

Arg Ser Ser Gln Ser Leu Val Tyr Ser Thr Gly Asn Thr Tyr Leu His
1 5 10 15

<210> SEQ ID NO 78
<211> LENGTH: 7
<212> TYPE: PRT
<213> ORGANISM: Artificial sequence
<220> FEATURE:
<223> OTHER INFORMATION: Synthetic

<400> SEQUENCE: 78

Trp Ala Ser Thr Arg Glu Ser
1 5

<210> SEQ ID NO 79
<211> LENGTH: 7
<212> TYPE: PRT
<213> ORGANISM: Artificial sequence
<220> FEATURE:
<223> OTHER INFORMATION: Synthetic

<400> SEQUENCE: 79

Trp Ala Ser Thr Trp Glu Ser
1 5

<210> SEQ ID NO 80
<211> LENGTH: 7
<212> TYPE: PRT
<213> ORGANISM: Artificial sequence
<220> FEATURE:
<223> OTHER INFORMATION: Synthetic

<400> SEQUENCE: 80

Lys Val Ser Asn Arg Phe Ser
1               5

<210> SEQ ID NO 81
<211> LENGTH: 7
<212> TYPE: PRT
<213> ORGANISM: Artificial sequence
<220> FEATURE:
<223> OTHER INFORMATION: Synthetic

<400> SEQUENCE: 81

Lys Val Ser Asn Arg Phe Ser
1               5

<210> SEQ ID NO 82
<211> LENGTH: 7
<212> TYPE: PRT
<213> ORGANISM: Artificial sequence
<220> FEATURE:
<223> OTHER INFORMATION: Synthetic

<400> SEQUENCE: 82

Trp Ala Ser Thr Arg Glu Ser
1               5

<210> SEQ ID NO 83
<211> LENGTH: 7
<212> TYPE: PRT
<213> ORGANISM: Artificial sequence
<220> FEATURE:
<223> OTHER INFORMATION: Synthetic

<400> SEQUENCE: 83

Lys Val Ser Asn Arg Phe Ser
1               5

<210> SEQ ID NO 84
<211> LENGTH: 9
<212> TYPE: PRT
<213> ORGANISM: Artificial sequence
<220> FEATURE:
<223> OTHER INFORMATION: Synthetic

<400> SEQUENCE: 84

Gln Gln Tyr Tyr Ser Lys Pro Tyr Thr
1               5

<210> SEQ ID NO 85
<211> LENGTH: 9
<212> TYPE: PRT
<213> ORGANISM: Artificial sequence
<220> FEATURE:
<223> OTHER INFORMATION: Synthetic

<400> SEQUENCE: 85

Gln Gln Tyr Tyr Thr Phe Pro Tyr Thr
1               5

<210> SEQ ID NO 86
<211> LENGTH: 9
<212> TYPE: PRT
<213> ORGANISM: Artificial sequence
<220> FEATURE:
<223> OTHER INFORMATION: Synthetic

<400> SEQUENCE: 86

Ser Gln Ser Arg His Ser Pro Trp Thr
1 5

<210> SEQ ID NO 87
<211> LENGTH: 9
<212> TYPE: PRT
<213> ORGANISM: Artificial sequence
<220> FEATURE:
<223> OTHER INFORMATION: Synthetic

<400> SEQUENCE: 87

Ser Gln Ser Arg His Ser Pro Trp Thr
1 5

<210> SEQ ID NO 88
<211> LENGTH: 9
<212> TYPE: PRT
<213> ORGANISM: Artificial sequence
<220> FEATURE:
<223> OTHER INFORMATION: Synthetic

<400> SEQUENCE: 88

Gln Gln Tyr Phe Ser Ser Pro Tyr Thr
1 5

<210> SEQ ID NO 89
<211> LENGTH: 9
<212> TYPE: PRT
<213> ORGANISM: Artificial sequence
<220> FEATURE:
<223> OTHER INFORMATION: Synthetic

<400> SEQUENCE: 89

Ser Gln Ser Arg His Gly Pro Trp Thr
1 5

<210> SEQ ID NO 90
<211> LENGTH: 5
<212> TYPE: PRT
<213> ORGANISM: Mus musculus
<220> FEATURE:
<221> NAME/KEY: VARIANT
<222> LOCATION: (5)..(5)
<223> OTHER INFORMATION: X is S or T

<400> SEQUENCE: 90

Thr Tyr Gly Met Xaa
1 5

<210> SEQ ID NO 91
<211> LENGTH: 17
<212> TYPE: PRT
<213> ORGANISM: Mus musculus
<220> FEATURE:
<221> NAME/KEY: VARIANT
<222> LOCATION: (5)..(5)
<223> OTHER INFORMATION: X is Y or F or S
<220> FEATURE:
<221> NAME/KEY: VARIANT
<222> LOCATION: (8)..(8)
<223> OTHER INFORMATION: X is L or V
<220> FEATURE:
<221> NAME/KEY: VARIANT
<222> LOCATION: (12)..(12)
<223> OTHER INFORMATION: X is A or T
<220> FEATURE:
<221> NAME/KEY: VARIANT
<222> LOCATION: (13)..(13)
<223> OTHER INFORMATION: X is D or N

```
<400> SEQUENCE: 91

Trp Ile Asn Thr Xaa Ser Gly Xaa Pro Thr Tyr Xaa Xaa Asp Phe Lys
1               5                   10                  15

Gly


<210> SEQ ID NO 92
<211> LENGTH: 10
<212> TYPE: PRT
<213> ORGANISM: Mus musculus
<220> FEATURE:
<221> NAME/KEY: VARIANT
<222> LOCATION: (3)..(3)
<223> OTHER INFORMATION: X is H or T
<220> FEATURE:
<221> NAME/KEY: VARIANT
<222> LOCATION: (4)..(4)
<223> OTHER INFORMATION: X is M or K or T
<220> FEATURE:
<221> NAME/KEY: VARIANT
<222> LOCATION: (7)..(7)
<223> OTHER INFORMATION: X is A or P
<220> FEATURE:
<221> NAME/KEY: VARIANT
<222> LOCATION: (8)..(8)
<223> OTHER INFORMATION: X is E or F or G

<400> SEQUENCE: 92

Pro Ile Xaa Xaa Val Val Xaa Xaa Asp Tyr
1               5                   10


<210> SEQ ID NO 93
<211> LENGTH: 12
<212> TYPE: PRT
<213> ORGANISM: Mus musculus
<220> FEATURE:
<221> NAME/KEY: VARIANT
<222> LOCATION: (1)..(1)
<223> OTHER INFORMATION: X is K or R
<220> FEATURE:
<221> NAME/KEY: VARIANT
<222> LOCATION: (7)..(7)
<223> OTHER INFORMATION: X is L or V
<220> FEATURE:
<221> NAME/KEY: VARIANT
<222> LOCATION: (9)..(9)
<223> OTHER INFORMATION: X is GRNQKN or SGNQKN or TYGNT or NYGNT or
      RSNQKN or STGNT
<220> FEATURE:
<221> NAME/KEY: VARIANT
<222> LOCATION: (12)..(12)
<223> OTHER INFORMATION: X is A or H

<400> SEQUENCE: 93

Xaa Ser Ser Gln Ser Leu Xaa Tyr Xaa Tyr Leu Xaa
1               5                   10


<210> SEQ ID NO 94
<211> LENGTH: 7
<212> TYPE: PRT
<213> ORGANISM: Mus musculus
<220> FEATURE:
<221> NAME/KEY: VARIANT
<222> LOCATION: (1)..(1)
<223> OTHER INFORMATION: X is K or W
<220> FEATURE:
<221> NAME/KEY: VARIANT
<222> LOCATION: (2)..(2)
<223> OTHER INFORMATION: X is A or V
<220> FEATURE:
<221> NAME/KEY: VARIANT
<222> LOCATION: (4)..(4)
```

<223> OTHER INFORMATION: X is N or T
<220> FEATURE:
<221> NAME/KEY: VARIANT
<222> LOCATION: (6)..(6)
<223> OTHER INFORMATION: X is E or F

<400> SEQUENCE: 94

Xaa Xaa Ser Xaa Arg Xaa Ser
1               5

<210> SEQ ID NO 95
<211> LENGTH: 9
<212> TYPE: PRT
<213> ORGANISM: Mus musculus
<220> FEATURE:
<221> NAME/KEY: VARIANT
<222> LOCATION: (3)..(3)
<223> OTHER INFORMATION: X is S or Y
<220> FEATURE:
<221> NAME/KEY: VARIANT
<222> LOCATION: (4)..(4)
<223> OTHER INFORMATION: X is F or R or Y
<220> FEATURE:
<221> NAME/KEY: VARIANT
<222> LOCATION: (5)..(5)
<223> OTHER INFORMATION: X is H or S or T
<220> FEATURE:
<221> NAME/KEY: VARIANT
<222> LOCATION: (6)..(6)
<223> OTHER INFORMATION: X is K or F or S or G
<220> FEATURE:
<221> NAME/KEY: misc_feature
<222> LOCATION: (8)..(8)
<223> OTHER INFORMATION: Xaa can be any naturally occurring amino acid

<400> SEQUENCE: 95

Gln Gln Xaa Xaa Xaa Xaa Pro Xaa Thr
1               5

<210> SEQ ID NO 96
<211> LENGTH: 5
<212> TYPE: PRT
<213> ORGANISM: Mus musculus
<220> FEATURE:
<221> NAME/KEY: VARIANT
<222> LOCATION: (1)..(1)
<223> OTHER INFORMATION: X is D or E
<220> FEATURE:
<221> NAME/KEY: VARIANT
<222> LOCATION: (3)..(3)
<223> OTHER INFORMATION: X is S or T
<220> FEATURE:
<221> NAME/KEY: VARIANT
<222> LOCATION: (4)..(4)
<223> OTHER INFORMATION: X is I or M

<400> SEQUENCE: 96

Xaa Tyr Xaa Xaa His
1               5

<210> SEQ ID NO 97
<211> LENGTH: 17
<212> TYPE: PRT
<213> ORGANISM: Mus musculus
<220> FEATURE:
<221> NAME/KEY: VARIANT
<222> LOCATION: (6)..(6)
<223> OTHER INFORMATION: X is S or T
<220> FEATURE:
<221> NAME/KEY: VARIANT
<222> LOCATION: (8)..(8)
<223> OTHER INFORMATION: X is D or E
<220> FEATURE:

-continued

<221> NAME/KEY: VARIANT
<222> LOCATION: (9)..(9)
<223> OTHER INFORMATION: X is P or T or A
<220> FEATURE:
<221> NAME/KEY: VARIANT
<222> LOCATION: (10)..(10)
<223> OTHER INFORMATION: X is T or S

<400> SEQUENCE: 97

Trp Ile Asn Thr Glu Xaa Gly Xaa Xaa Xaa Tyr Ala Asp Asp Phe Lys
1               5                   10                  15

Gly

<210> SEQ ID NO 98
<211> LENGTH: 4
<212> TYPE: PRT
<213> ORGANISM: Mus musculus
<220> FEATURE:
<221> NAME/KEY: VARIANT
<222> LOCATION: (2)..(2)
<223> OTHER INFORMATION: X is F or G or R
<220> FEATURE:
<221> NAME/KEY: VARIANT
<222> LOCATION: (3)..(3)
<223> OTHER INFORMATION: X is D or E or A or F
<220> FEATURE:
<221> NAME/KEY: VARIANT
<222> LOCATION: (3)..(3)
<223> OTHER INFORMATION: X is D or E or A or F or G

<400> SEQUENCE: 98

Arg Xaa Xaa Tyr
1

<210> SEQ ID NO 99
<211> LENGTH: 9
<212> TYPE: PRT
<213> ORGANISM: Mus musculus
<220> FEATURE:
<221> NAME/KEY: VARIANT
<222> LOCATION: (1)..(1)
<223> OTHER INFORMATION: X is R or K
<220> FEATURE:
<221> NAME/KEY: VARIANT
<222> LOCATION: (2)..(2)
<223> OTHER INFORMATION: X is A or S
<220> FEATURE:
<221> NAME/KEY: VARIANT
<222> LOCATION: (6)..(6)
<223> OTHER INFORMATION: X is L or V
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: VARIANT
<222> LOCATION: (9)..(9)
<223> OTHER INFORMATION: X is N or S
<220> FEATURE:
<221> NAME/KEY: VARIANT
<222> LOCATION: (9)..(9)
<223> OTHER INFORMATION: X is N or S or T
<220> FEATURE:
<221> NAME/KEY: VARIANT
<222> LOCATION: (9)..(9)
<223> OTHER INFORMATION: X is N or S or T or H or R or K

<400> SEQUENCE: 99

Xaa Xaa Ser Gln Ser Xaa Xaa Xaa Xaa
1               5

<210> SEQ ID NO 100

-continued

```
<211> LENGTH: 6
<212> TYPE: PRT
<213> ORGANISM: Mus musculus
<220> FEATURE:
<221> NAME/KEY: VARIANT
<222> LOCATION: (1)..(1)
<223> OTHER INFORMATION: X is V or A
<220> FEATURE:
<221> NAME/KEY: VARIANT
<222> LOCATION: (5)..(5)
<223> OTHER INFORMATION: X is F and Y
<220> FEATURE:
<221> NAME/KEY: VARIANT
<222> LOCATION: (6)..(6)
<223> OTHER INFORMATION: X is S or T

<400> SEQUENCE: 100

Xaa Ser Asn Arg Xaa Xaa
1               5


<210> SEQ ID NO 101
<211> LENGTH: 8
<212> TYPE: PRT
<213> ORGANISM: Mus musculus
<220> FEATURE:
<221> NAME/KEY: VARIANT
<222> LOCATION: (3)..(3)
<223> OTHER INFORMATION: X is S or D
<220> FEATURE:
<221> NAME/KEY: VARIANT
<222> LOCATION: (4)..(4)
<223> OTHER INFORMATION: X is T or Y or R or K or S
<220> FEATURE:
<221> NAME/KEY: VARIANT
<222> LOCATION: (5)..(5)
<223> OTHER INFORMATION: X is H or N or E or T or Y or S
<220> FEATURE:
<221> NAME/KEY: VARIANT
<222> LOCATION: (5)..(5)
<223> OTHER INFORMATION: X is H or N or E or T or Y or S or V or L or I

<400> SEQUENCE: 101

Gln Asp Xaa Xaa Xaa Pro Trp Thr
1               5
```

NON-VIRAL IMMUNO-TARGETING

CROSS-REFERENCES TO RELATED APPLICATIONS

This application is a National Stage of International Application No. PCT/US2020/041441, filed Jul. 9, 2020, which claims priority benefit of U.S. Provisional Application No. 62/872,425, filed Jul. 10, 2019, the entire disclosures of which are incorporated by reference herein in their entirety.

STATEMENT OF GOVERNMENT LICENSE RIGHTS

This invention was made with government support under Grant No. W81XWH-22-1-0659, awarded by the Department of Defense (DOD). The government has certain rights in the invention.

STATEMENT REGARDING SEQUENCE LISTING

The sequence listing associated with this application is provided in text format in lieu of a paper copy and is hereby incorporated by reference into the specification. The name of the text file containing the sequence listing is 3915-P916US.PNP.UW_Seq_List_20250924. The text file is 152,836 bytes; was created on Sep. 24, 2025; and is being submitted electronically via Patent Center.

BACKGROUND

Human diseases involving muscle range from relatively rare conditions such as muscular dystrophies, to common ailments such as diabetes and age-related muscle weakness (sarcopenia). Currently, there are no effective treatments for many muscle diseases, including the most common and severe form of muscular dystrophy, known as Duchenne muscular dystrophy (DMD). A brief overview of the main features of DMD is shown schematically in FIG. 1. Since dystrophin, the gene responsible for DMD, was discovered in 1987, researchers have attempted to develop techniques to deliver the dystrophin gene to muscles and thereby improve or even cure the disease. However, a major drawback to this approach for DMD is the huge size of the wild-type dystrophin gene, ~14 kilobases for the mature transcript, which is far too large to fit into viral vectors available for delivering genes to tissues. To illustrate, the most commonly used gene therapy viral vector is adeno-associated virus (AAV), which has a total packaging capacity of only 5 kilobases. Consequently, to provide a deliverable therapeutic dystrophin transgene, the dystrophin gene must be truncated to 'micro-dystrophins', which are about one third the size of full-length dystrophin and provide only partial improvement of in vivo muscle function in the mdx (DMD) mouse. Other major problems associated with viral vectors include a lack of specificity in targeting the vector to the desired cell type and potential immune responses associated with viral delivery. The potential of eliciting an immune response is a significant limitation of AAV approaches because it functionally limits therapeutic delivery to a single administration. This is very likely to be insufficient for treating degenerative muscle diseases such as DMD, which can require intervention over years or even decades. In addition, many humans have already been exposed to certain AAV serotypes, which would exclude them from AAV gene therapy altogether.

Accordingly, despite the advances in the art of understanding muscular diseases and viral vectors for therapeutic payloads, a need remains for non-immunogenic vector platforms that can specifically deliver therapeutic payloads to muscle cells without limitations on payload size or type. This disclosure addresses these and related needs.

SUMMARY

This summary is provided to introduce a selection of concepts in an abbreviated form that are further described below in the Detailed Description. This summary is not intended to identify key features of the claimed subject matter, nor is it intended to be used as an aid in determining the scope of the claimed subject matter.

In one aspect, the disclosure provides a composition comprising a binding domain, e.g., an antibody, or fragment or derivative thereof, that specifically binds to glucose transporter 4 ("GLUT4") protein, and a therapeutic payload conjugated to the binding domain.

In another aspect, the disclosure provides a method of targeting a therapeutic payload for delivery to a cell that expresses GLUT4, the method comprising contacting the cell with the disclosed composition. The method can be in vitro. Alternatively, the method can be an in vivo method of treating a disease or condition associated with GLUT4 expressing cells.

In another aspect, the disclosure provides a method of treating a disease or condition in a subject with a genetic mutation in a gene encoding dystrophin protein, comprising administering to a subject a therapeutically effective amount of the disclosed composition. The composition in this method aspect comprises a binding domain, e.g., an antibody, or fragment or derivative thereof, that specifically binds glucose transporter 4 ("GLUT4") protein, and a therapeutic payload conjugated to the antibody, or fragment or derivative thereof. The therapeutic payload comprises a nucleic acid with a promoter sequence operatively linked to a sequence encoding a dystrophin protein, or a functional fragment thereof.

DETAILED DESCRIPTION

Figure 1:
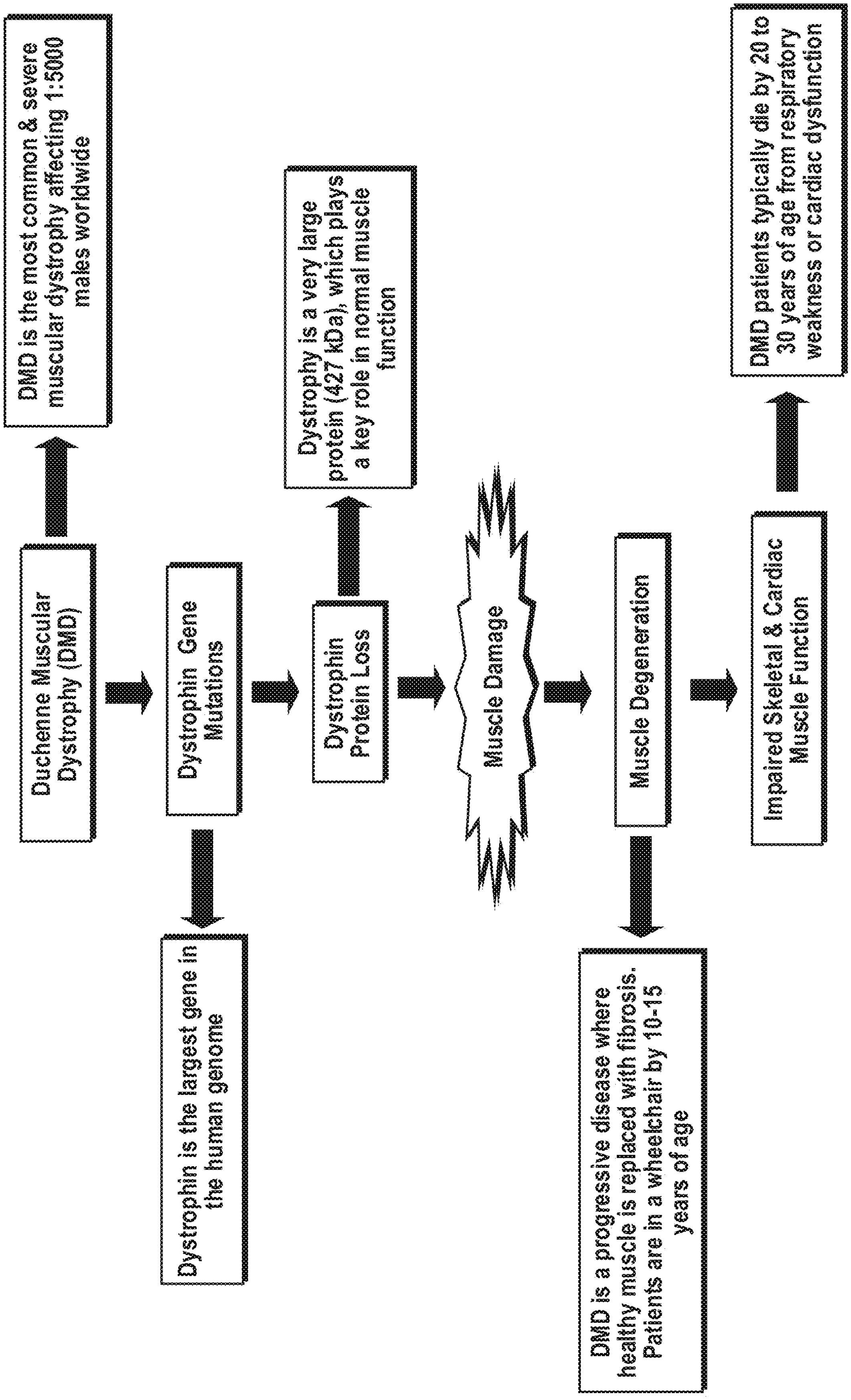
FIG. 1 is a schematic overview of Duchenne muscular dystrophy (DMD).
Figure 2:
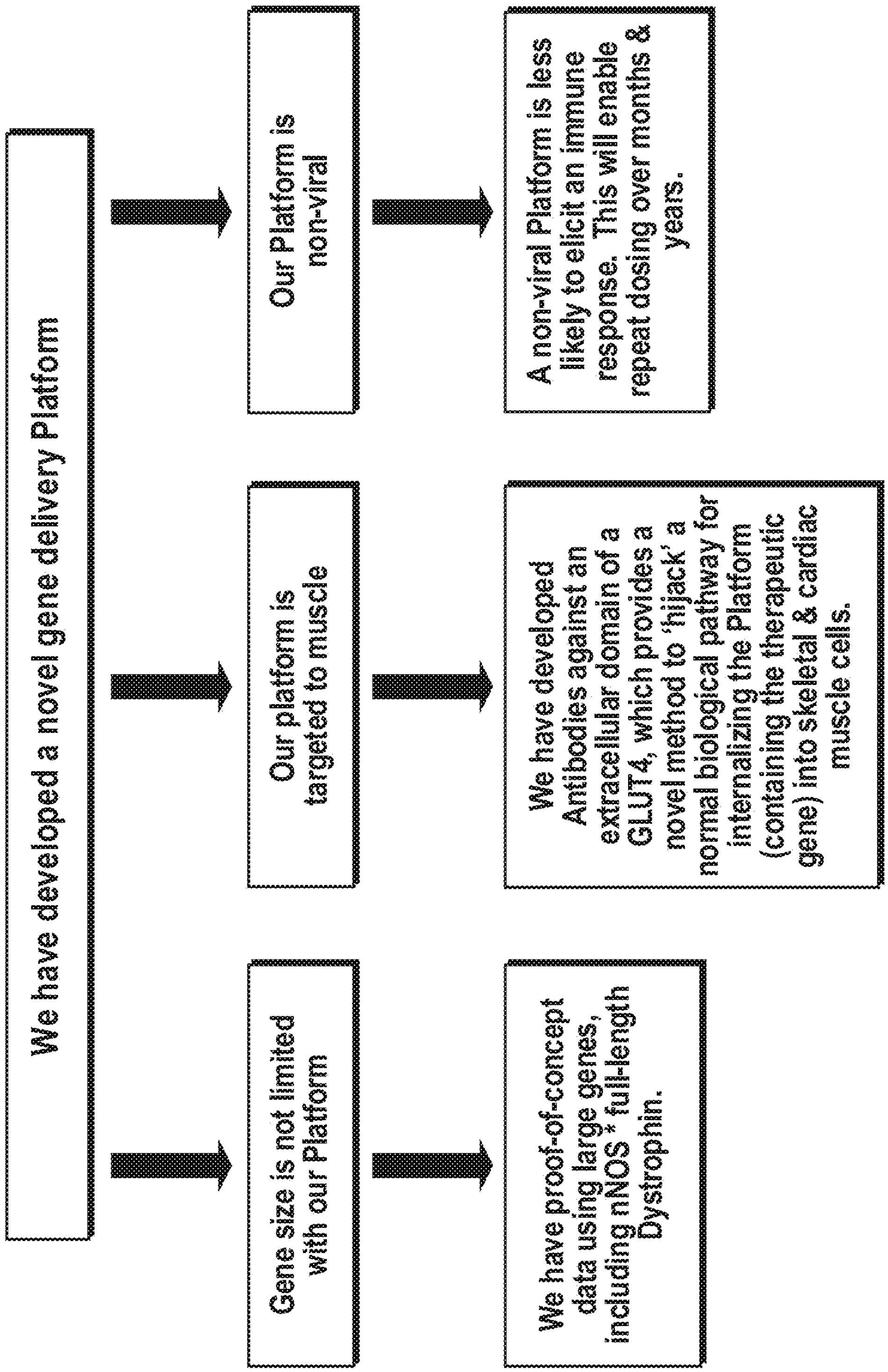
FIG. 2 is a schematic overview of aspects of the non-viral, muscle-targeted gene delivery platform disclosed herein.

This disclosure is based on the inventors' development of non-viral vector platforms for specifically targeting therapeutic payloads, both genetic and pharmacological, to skeletal and cardiac muscle tissue. Briefly, the platform design, outlined in FIG. 2, was focused on permitting large payload capacities, such as the full-length dystrophin gene transcript to permit treatment of diseases relating to dysfunction of the dystrophin expression or gene product.

The platform leverages the specific and insulin-dependent expression of glucose transporter 4 (GLUT4) protein in muscle and other limited tissues. GLUT4 is encoded by the SLC2A4 gene, which is predominantly expressed in striated muscle (skeletal and cardiac) and adipose tissue, but is also expressed in certain areas of the brain, including the hippocampus and cerebellum. GLUT4 is a member of a family of glucose transport proteins. Glucose transporters are integral membrane proteins containing 12 membrane-spanning helix domains. GLUT4 is highly expressed in muscle and fat tissue while other members of the glucose transporter family are specific to other tissues. For example, GLUT3, a high-affinity glucose transporter, is the primary glucose transporter in neurons. Under basal conditions, GLUT4 mostly resides in intracellular vesicles but traffics to, and fuses with, the plasma membrane upon treatment with insulin, thereby mediating insulin-dependent glucose uptake. Following insulin binding to the insulin receptor, a signaling pathway is activated, leading to GLUT4 translocation to the plasma membrane. This process occurs within 15 min of insulin binding. Once insulin concentrations decrease, over time GLUT4 is internalized in vesicles and either traffics through the endosomal system or is recycled back to the plasma membrane.

The disclosed vector platform leverages this bidirectional, vesicle-mediated movement of GLUT4 to the plasma membrane and then back inside the cell to provide a strategy to deliver therapeutics into GLUT4 expressing cells and tissues. As described in more detail below, novel antibodies, both rabbit polyclonal and mouse monoclonal, were first developed that bind to an extracellular domain of the mouse GLUT4 protein. Using various antibody conjugation techniques, several payload/vector structures were produced. A series of in vitro and in vivo experiments were conducted to assess the specificity, carrying capacity, and other useful aspects of these representative embodiments of the platform vector. For example, it was demonstrated that an effectively targeted therapeutic transgene, including plasmid DNA as large as 19 kilobases containing the full-length dystrophin gene, can be taken up and expressed by muscle cells. The plasmid DNA was successfully transported into the cell following GLUT4 internalization and expression of the dystrophin gene was established. The assays ultimately demonstrate the usefulness of the platform for addressing muscle diseases that have heretofore been difficult to treat. Not only is the platform flexible to permit a variety of therapeutic payload types, it also does not require viral components. Accordingly, the platform permits repeated administration over time, including periods of years, to address chronic and degenerative muscle diseases without risk of immunogenicity.

In accordance with the foregoing, the disclosure provides a composition comprising a binding domain that specifically binds to glucose transporter 4 ("GLUT4") protein. The composition further comprises a therapeutic payload conjugated to the binding domain.

Binding Domain

In some embodiments, the binding domain is or comprises an antibody, or fragment or derivative thereof. In such embodiments, the therapeutic payload can be directly or indirectly conjugated to antibody, or fragment or derivative thereof.

The term "antibody" is used herein in the broadest sense and encompasses various antibody structures derived from any antibody-producing mammal (e.g., mouse, rat, rabbit, and primate including human), and which specifically bind to an antigen of interest. An antibody fragment specifically refers to an intact portion or subdomain of a source antibody that still retains antigen-binding capability. An antibody derivative refers to a molecule that incorporates one or more antibodies or antibody fragments. Typically, there is at least some additional modification in the structure of the antibody or fragment thereof, or in the presentation or configuration of the antibody or fragment thereof. Exemplary antibodies of the disclosure include polyclonal, monoclonal and recombinant antibodies. Exemplary antibodies or antibody derivatives of the disclosure also include multispecific antibodies (e.g., bispecific antibodies); humanized antibodies; murine antibodies; chimeric, mouse-human, mouse-primate, primate- As indicated, an antibody fragment is a portion or subdomain derived from or related to a full-length antibody, preferably including the complementarity-determining regions (CDRs), antigen binding regions, or variable regions thereof, and antibody derivatives refer to further structural modification or combinations in the resulting molecule. Illustrative examples of antibody fragments or derivatives encompassed by the present disclosure include Fab, Fab', $F(ab)_2$, $F(ab')_2$ and Fv fragments, diabodies, single-chain antibody molecules, $V_HH$ fragments, $V_{NAR}$ fragments, multispecific antibodies formed from antibody fragments, nanobodies and the like. For example, an exemplary single chain antibody derivative encompassed by the disclosure is a "single-chain Fv" or "scFv" antibody fragment, which comprises the $V_H$ and $V_L$ domains of an antibody, wherein these domains are present in a single polypeptide chain. The Fv polypeptide can further comprise a polypeptide linker between the $V_H$ and $V_L$ domains, which enables the scFv to form the desired structure for antigen binding. Another exemplary single-chain antibody encompassed by the disclosure is a single-chain Fab fragment (scFab).

As indicated, antibodies can be further modified to created derivatives that suit various uses. For example, a "chimeric antibody" is a recombinant protein that contains domains from different sources. For example, the variable domains and complementarity-determining regions (CDRs) can be derived from a non-human species (e.g., rodent) antibody, while the remainder of the antibody molecule is derived from a human antibody. A "humanized antibody" is a chimeric antibody that comprises a minimal sequence that conforms to specific complementarity-determining regions derived from non-human immunoglobulin that is transplanted into a human antibody framework. Humanized antibodies are typically recombinant proteins in which only the antibody complementarity-determining regions (CDRs) are of non-human origin. Any of these antibodies, or fragments or derivatives thereof, are encompassed by the disclosure.

Antibody fragments and derivatives that recognize specific epitopes can be generated by any technique known to those of skill in the art. For example, Fab and $F(ab')_2$ fragments of the disclosure can be produced by proteolytic cleavage of immunoglobulin molecules, using enzymes such as papain (to produce Fab fragments) or pepsin (to produce $F(ab')_2$ fragments). $F(ab')_2$ fragments contain the variable region, the light chain constant region and the CHI domain of the heavy chain. Further, the antibodies, or fragments or derivatives thereof, of the present disclosure can also be generated using various phage display methods known in the art. Finally, the antibodies, or fragments or derivatives thereof, can be produced recombinantly according to known techniques.

It will be apparent to the skilled practitioner that the binding domain can comprise antigen binding molecules other than antibody-based domain, such as peptidobodies, antigen-binding scaffolds (e.g., DARPins, HEAT repeat proteins, ARM repeat proteins, tetratricopeptide repeat proteins, and other scaffolds based on naturally occurring repeat proteins, etc. [see, e.g., Boersma and Pluckthun, *Curr. Opin. Biotechnol.* 22:849-857, 2011, and references cited therein, incorporated herein by reference]), which include a functional binding domain or antigen-binding fragment thereof.

In some embodiments, the binding domain (e.g., an antibody, or fragment or derivative thereof) is biotinylated. As described in more detail below, biotinylation facilitates some embodiments of composition assembly/conjugation.

As used herein, the term "specifically bind" or variations thereof refer to the ability of the binding domain (e.g., of the antibody, or fragment or derivative thereof) to bind to the antigen of interest (e.g., GLUT4), without significant binding to other molecules, under standard conditions known in the art. The binding domain can bind to other peptides, polypeptides, or proteins, but with lower affinity as determined by, e.g., immunoassays, BIAcore, or other assays known in the art. However, the binding domain preferably does not substantially cross-react with other antigens.

In some embodiments, the GLUT4-binding domain of the composition has a binding affinity has a binding affinity within a range characterized by a dissociation constant ($K_d$) from about 50 nM (lower binding affinity) to about 0.001 nM (higher binding affinity). For example, the binding domain has a binding affinity for the GLUT protein characterized by ($K_d$) of about 50 nM, 40 nM, 30 nM, 20 nM, 10 nM, 5 nM, 1 nM, 0.75 nM, 0.5 nM, 0.1 nM, 0.05 nM, 0.01 nM, 0.005 nM, and 0.001 nM, or even smaller. Typical ($K_d$) ranges characterizing the binding affinity of the cell-targeting domain for the antigen characteristic of the cell-type of interest include from about 30 nM to about 10 nM, from about 20 nM to about 1 nM, from about 10 nM to about 0.1 nM, from about 0.5 nM to about 0.05 nM, and from about 0.1 nM to about 0.001 nM, or even lower, or any subrange therein.

Binding Target

As indicated above, the binding domain (e.g., an antibody, or fragment or derivative thereof) specifically binds to glucose transporter 4 (GLUT4) protein. GLUT 4 is encoded by the SLC2A4 gene (or homologs thereof), which is predominantly expressed in striated muscle (skeletal and cardiac) and adipose tissue, but is also expressed in certain areas of the brain, including the hippocampus and cerebellum. This disclosure encompasses GLUT4 from any mammal, such as human, mouse, rat, cat, dog, horse, etc. In some embodiments, the binding domain specifically binds to an extracellular domain of GLUT4 protein.

In some embodiments, the binding domain specifically binds to a first extracellular loop domain of GLUT4. In some embodiments, the first extracellular loop domain of GLUT4 comprises an amino acid sequence with at least about 80% sequence identity (e.g., at least about 80%, at least about 85%, at least about 90%, at least about 92%, at least about 94%, at least about 96%, at least about 98%, and 100% sequence identity) to the sequence set forth in SEQ ID NO:2, which is a subdomain of a human GLUT4 first extracellular loop domain. For example, exemplary GLUT4 domain contemplated by the present disclosure include the domains set forth in Genbank Accession No. M91463.1 (human), Genbank Accession No. AB008453.1 (mouse), Genbank Accession No. NM_001159327.1 (dog), and Genbank Accession No. L36125.1 (rat), each of this is incorporated herein by reference in its entirety. In some embodiments, the GLUT4 first extracellular loop domain comprises an amino acid sequence with at least about 80% sequence identity (e.g., at least about 80%, at least about 85%, at least about 90%, at least about 92%, at least about 94%, at least about 96%, at least about 98%, and 100% sequence identity) to the sequence set forth in SEQ ID NO:1, which is a representative human GLUT4 first extracellular loop domain. In some embodiments, the binding domain specifically binds to a subdomain of the first extracellular loop domain of GLUT4 that comprises a sequence with at least 80% sequence identity (e.g., at least about 80%, at least about 85%, at least about 90%, at least about 92%, at least about 94%, at least about 96%, at least about 98% sequence identity, and 100% sequence identity) to the sequence set forth in SEQ ID NO:2.

In some embodiments, the first extracellular loop domain of GLUT4 comprises an amino acid sequence with at least about 80% sequence identity (e.g., at least about 80%, at least about 85%, at least about 90%, at least about 92%, at least about 94%, at least about 96%, at least about 98%, and 100% sequence identity) to the sequence set forth in SEQ ID NO: 4, which is a subdomain of a murine GLUT4 first extracellular loop domain. In some embodiments, the GLUT4 first extracellular loop domain comprises an amino acid sequence with at least about 80% sequence identity (e.g., at least about 80%, at least about 85%, at least about 90%, at least about 92%, at least about 94%, at least about 96%, at least about 98%, and 100% sequence identity) to the sequence set forth in SEQ ID NO:3, which is a representative murine GLUT4 first extracellular loop domain. In some embodiments, the binding domain specifically binds to a subdomain of the first extracellular loop domain of GLUT4 that comprises a sequence with at least 80% sequence identity (e.g., at least about 80%, at least about 85%, at least about 90%, at least about 92%, at least about 94%, at least about 96%, at least about 98% sequence identity) to the sequence set forth in SEQ ID NO:4.

Payload

The therapeutic payload can be any payload capable of inducing a change in a target cell that expresses, at least transiently, a GLUT4 on its surface. The change can be to a therapeutic effect if it is in vivo. Exemplary, non-limiting therapeutic payloads can comprise a nucleic acid, a protein or peptide, a lipid, a small molecule pharmaceutical, and/or a radioisotope.

For example, in some embodiments, the therapeutic payload comprises a nucleic acid, such as DNA (including cDNA), mRNA, siRNA, shRNA, and gRNA. Guide RNA molecules can be utilized in applications of DNA editing (e.g., CRISPR/Cas9 applications) and RNA editing.

In some embodiments, the nucleic acid comprises a sequence (e.g., open reading frame) encoding a protein that has a therapeutic effect in the target cell. In some embodiments, the nucleic acid comprises an open reading frame operatively linked to a promoter sequence to provide for expression of the open reading frame in the target cell. This open reading frame can be referred to as a transgene. The term "promoter" refers to a regulatory nucleotide sequence that can activate transcription (expression) of the transgene and/or splice variant isoforms thereof. The promoter is typically located upstream of the gene, but can be located at other regions proximal to the gene, or even within the gene. The promoter typically contains binding sites for RNA polymerase and one or more transcription factors, which participate in the assembly of the transcriptional complex. As used herein, the term "operatively linked" indicates that the promoter and the encoding nucleic acid are configured and positioned relative to each other a manner such that the promoter can activate transcription of the encoding nucleic acid by the transcriptional machinery of the cell. The promoter can be constitutive or inducible. Constitutive promoters can be determined based on the character of the target cell and the particular transcription factors available in the cytosol. A person of ordinary skill in the art can select an appropriate promoter based on the intended person, as various promoters are known and commonly used in the art. Exemplary, non-limiting promoters include muscle creatine kinase (CK) promoter (Genbank Accession No. AF188002.1) and human skeletal actin promoter (Genbank Accession No. NG_006672.1), each of which is incorporated herein by reference. While the advances provided herein permit use of full-length promoters, abbreviated promoters that retain some activity are still encompassed by the present disclosure. Exemplary, non-limiting examples of abbreviated CK promoters that retain activity are described in Hauser M A, et al., Analysis of muscle creatine kinase regulatory elements in recombinant adenoviral vectors, *Mol Ther.* 20001 2 (1): 16-25, and Brennan K J and Hardeman E C, Quantitative analysis of the human alpha-skeletal actin gene in transgenic mice, *J Biol Chem.* 1993 268 (1): 719-725, each of which is incorporated herein by reference in its entirety.

The nucleic acid therapeutic payload can be of any size and in any configuration, such as in linear form, in plasmid form (e.g., circular form), or in minicircle form. As demonstrated below, the compositions of the present disclosure were demonstrated as being able to deliver very large transgenes for successful expression in target cells. Thus, the nucleic acid payloads are not limited in a manner that practically restricts the use of typical viral vectors. Thus, linear forms of nucleic acids can encompass short oligos or longer transgenes, without limitation. As understood by skilled practitioners, minicircles are smaller circular plasmid derivatives that lack most or all prokaryotic vector components. Minicircles can function as transgene carriers with an advantage of being less susceptible to degradation due to the smaller size and/or the lack of prokaryotic sequence.

As indicated above, the nucleic acid can be a transgene configured to comprise a sequence encoding any desired protein or protein fragment to be expressed in the target cell. The transgene can encode any protein that is desired to be expressed in the cell. In some embodiments, the transgene encodes a protein that has a beneficial effect on the cell compared to a mutant endogenous version existing in the target cell. For example, as described above, Duchenne muscular dystrophy (DMD) is a debilitating sex-linked disease resulting from aberrant dystrophin protein (or aberrant dystrophin protein expression). The gene encoding dystrophin, referred to as the "DMD" gene, is one of the longest human genes, covering about 2.3 megabases (0.08% of the human genome) at locus Xp21 with about 79 exons. The primary wild-type transcript is about 21 kilobases, and the mature mRNA is about 14 kilobases. As described below, the inventors established that the disclosed vector platform can deliver such long transgenes to GLUT4+ cells (e.g., muscle cells) to successfully achieve expression. Accordingly, an exemplary and non-limiting example of a nucleic acid payload encompasses the encoding nucleotide sequence encoding dystrophin protein, or a functional fragment thereof, operatively linked to a promoter sequence. In some embodiments, the encoded dystrophin protein is a full length human dystrophin protein or a substantially full length human dystrophin protein. An exemplary full length protein sequence for human dystrophin is set forth in SEQ ID NO:5. In some embodiments, the nucleic acid payload encodes a dystrophin with at least about 80% sequence identity (e.g., at least about 80%, at least about 85%, at least about 90%, at least about 92%, at least about 94%, at least about 96%, at least about 98%, and 100% sequence identity) to the sequence set forth in SEQ ID NO: 5.

The term "substantially full length" encompasses embodiments where a significant but incomplete version of dystrophin is encoded, such as at least about 85%, at least about 90%, at least about 92%, at least about 94%, at least about 96%, at least about 98%, or at least about 99% of a full length dystrophin protein (e.g., with at least 80% sequence identity to SEQ ID NO:5, as described above) is encoded providing a degree of phenotypic improvement in the target cell.

It has also been shown that "micro-dystrophin" proteins administered to or expressed in a cell with an aberrant or mutated DMD gene can provide at least some ameliorative effect compensating for the endogenous mutation in the DMD gene. While not being bound to any particular theory, it is believed that many truncated versions of dystrophin have improved functionality over the mutated or aberrant expression of dystrophin in subjects with DMD and other dystrophin related diseases. Accordingly, delivery or inducement of expression of these truncated or micro-dystrophin proteins with the muscle cell can begin to restore a relatively healthy or improved phenotype. Accordingly, in some embodiments, the nucleic acid payload can encode a functional fragment of the dystrophin protein, such as any micro-dystrophin known in the art. For example, Ramos et al., 2019 *Molecular Therapies* 27:623-635, incorporated herein by reference, describe several miniaturized micro-dystrophin constructs that are optimized to improve performance. Exemplary and non-limiting regions and domains of the dystrophin protein that have been shown to possess characteristics contributing to functionality of micro-dystrophin constructs include: a rod domain with at least 4 SR domains, α-syntrophin-binding domain in SR16-17, an actin binding domain, and cysteine-rich domain for binding β-dystroglycan.

In some embodiments, the full length dystrophin protein has an amino acid sequence with at least 80% sequence identity (e.g., at least about 80%, at least about 85%, at least about 90%, at least about 92%, at least about 94%, at least about 96%, at least about 98%, and 100% sequence identity) to the sequence set forth as SEQ ID NO:5, which is a predicted full-length human protein sequence for dystrophin. The sequence has a Genbank accession number AAA53189.1 and is incorporated herein by reference in its entirety. In other embodiments, the full length dystrophin protein has an amino acid sequence with at least 80% sequence identity (e.g., at least about 80%, at least about 85%, at least about 90%, at least about 92%, at least about 94%, at least about 96%, at least about 98%, and 100% sequence identity) to the sequence set forth as SEQ ID NO:6, which is a predicted full-length murine protein sequence for dystrophin. The sequence has a Genbank accession number NP_031894.1 and is incorporated herein by reference in its entirety. In yet other embodiments, the full length human dystrophin protein has an amino acid sequence with at least 80% sequence identity (e.g., at least about 80%, at least about 85%, at least about 90%, at least about 92%, at least about 94%, at least about 96%, at least about 98%, and 100% sequence identity) to the sequence set forth as SEQ ID NO:7, which is a predicted full-length rat protein sequence for dystrophin. The sequence has a Genbank accession number XP_017457396.1 and is incorporated herein by reference in its entirety. In yet other embodiments, the full length human dystrophin protein has an amino acid sequence with at least 80% sequence identity (e.g., at least about 80%, at least about 85%, at least about 90%, at least about 92%, at least about 94%, at least about 96%, at least about 98%, and 100% sequence identity) to the sequence set forth as SEQ ID NO:8, which is a predicted full-length rabbit protein sequence for dystrophin. The sequence has a Genbank accession number XP_017205220.1 and is incorporated herein by reference in its entirety. As indicated above, the nucleic acid therapeutic payload in these embodiments can comprise the full length dystrophin protein sequence, substantially full length dystrophin sequence, or be a functional fragment thereof that retains the ability to provide at least some therapeutic effect towards restoring an improved phenotype.

As indicated above, the nucleic acid payload can comprise linear nucleic acids, such short oligomers. In some embodiments, the nucleic acid is not a transgene that encodes a protein, but rather alters the endogenous expression and translation of proteins in the target cell. For example, in some therapeutic approaches for treating genomic diseases such as DMD, nucleic acid oligos are administered to promote skipping of exons in the pre-mRNA that contain a mutation resulting in a frameshift. The administered nucleic acid oligos (e.g., phosphodiamedate morpholino oligomers) are configured to hybridize to the mutated pre-mRNA in a sequence specific manner and sterically hinder spliceosome from binding at the junctions of the mutated exon in the encoding pre-mRNA molecule. The result is that the spliceosome excises not only the introns but the exon containing the frameshifting mutation. The resulting mature mRNA encodes for a slightly truncated protein lacking the mutated exon and maintaining the reading frame along all the remaining introns. The truncated protein retains at least some wild-type characteristics compared to the version containing the frameshift. This approach has been implemented for DMD. However, typical approaches require very large quantities of oligos due to the high rate of degradation after administration. See, e.g., Verhaart I E C and Aartsma-Rus A, Therapeutic developments for Duchenne muscular dystrophy, Nat Rev Neurol. 2019 July; 15 (7): 373-386, incorporated herein by reference in its entirety. The nucleic acid payload of the present disclosure encompasses therapeutic oligomers such as these. The disclosed platform provides the advantage of specific targeting of the oligomers to the target cell, which leads to efficient uptake into the cell. Thus, the disclosed targeting platform does not require such high doses of oligos and provides higher likelihood of delivery to and uptake by the target cells.

In other embodiments, the nucleic acid payload of the present disclosure can be configured to promote RNA interference. For instance, in some embodiments the nucleic acid payload is or comprises short interfering RNA (siRNA) or short hairpin RNA (shRNA) molecules, or nucleic acid encoding the siRNA or shRNA molecules. The sequences of such nucleic acid molecules can be readily configured according to skill and knowledge in the art to result in binding to and subsequence degradation of mRNA transcripts to result in knockdown of any desired target protein in the cell.

In any embodiment of a nucleic acid payload, but particularly when the nucleic acid payload is quite large (for example for long nucleic acids encoding dystrophin or large portions thereof) the composition can further comprise additional components to facilitate efficient coiling or packaging (e.g., condensing) of the nucleic acid. The additional packaging can be useful for linear (e.g., oligo or long sequences), plasmid, and minicircle embodiments of the nucleic acid payload, as described above, without limitation. For example, in one embodiment, the composition further comprises a histone protein or a plurality of histone proteins associated with the nucleic acid. The histone protein(s) can facilitate the coiling of the nucleic acid payload for effective packaging and transfer. In some embodiments, the histone protein or at least a portion of the plurality of histone proteins is/are biotinylated to facilitate conjugation, as described in more detail below.

In other embodiments, the composition further comprises a plurality of cationic moieties associated with the nucleic acid, thereby resulting in condensed nucleic acid. Without being limited to any particular theory, cationic molecules can potentially condense DNA, which is a polymeric anionic molecule. Thus, peptides containing a plurality of positively charged amino acids are useful for condensing the polymeric nucleic acid payload. Exemplary cationic amino acids include Lysine (Lys, K), Histidine (His, H), and Arginine (Arg, R). Accordingly, in some embodiments, the composition further comprises one or more cationic peptides, where the cationic peptides comprise a plurality of cationic amino acids, e.g., selected from His, Arg, and Lys, potentially in combination. The peptide typically has a net positive charge. In some embodiment, the peptide comprises one or more poly-L-Lys ("PLL") peptide moieties. Additional, non-limiting cationic molecules or moieties that can be included in the composition to condense the nucleic acid payload include linear Polyethylenimine ("LPEI"), branched Polyethylenimine ("BPEI"), chitosan, spermidine and spermine, Polyamidoamine ("PAMAM"), poly(2-dimethylaminoethyl methacrylate) ("PDMAEMA"), Poly(beta-amino ester) s ("PBAEs"), poly {N—[N-(2-aminoethyl)-2-aminoethyl]aspartamide ("PAsp (DET)"), poly(2-aminoethyl ethylene phosphate ("PPEEA"), and the like.

In some embodiments, at least a portion of the cationic moieties, such as PLL or other cationic molecules indicated above, is biotinylated to facilitate conjugation, as described in more detail below.

Conjugation

The binding domain, e.g., antibody, or fragments or derivative thereof, can be conjugated to the therapeutic payload according to any known technique. The conjugation can be covalent or ionic.

In some illustrative, non-limiting embodiments, the conjugation relies on the interaction between biotin and a binding partner, such as avidin, neutravidin, and streptavidin, to provide a very high affinity and specific conjugation of the component parts of the composition.

For example, in one embodiment, the binding domain (e.g., antibody, or fragment or derivative thereof), and a DNA coiling or condensing element (e.g., histone or cationic peptide) are each biotinylated. The nucleic acid payload is associated with the DNA coiling or condensing element (e.g., coiled around or condensed by the coiling or condensing element). Through the mutual interactions with the multiple biotinylated components with the same neutravidin molecule, the binding domain and the coiling or condensing element and associate nucleic acid payload are conjugated together with high affinity.

Figure 3:
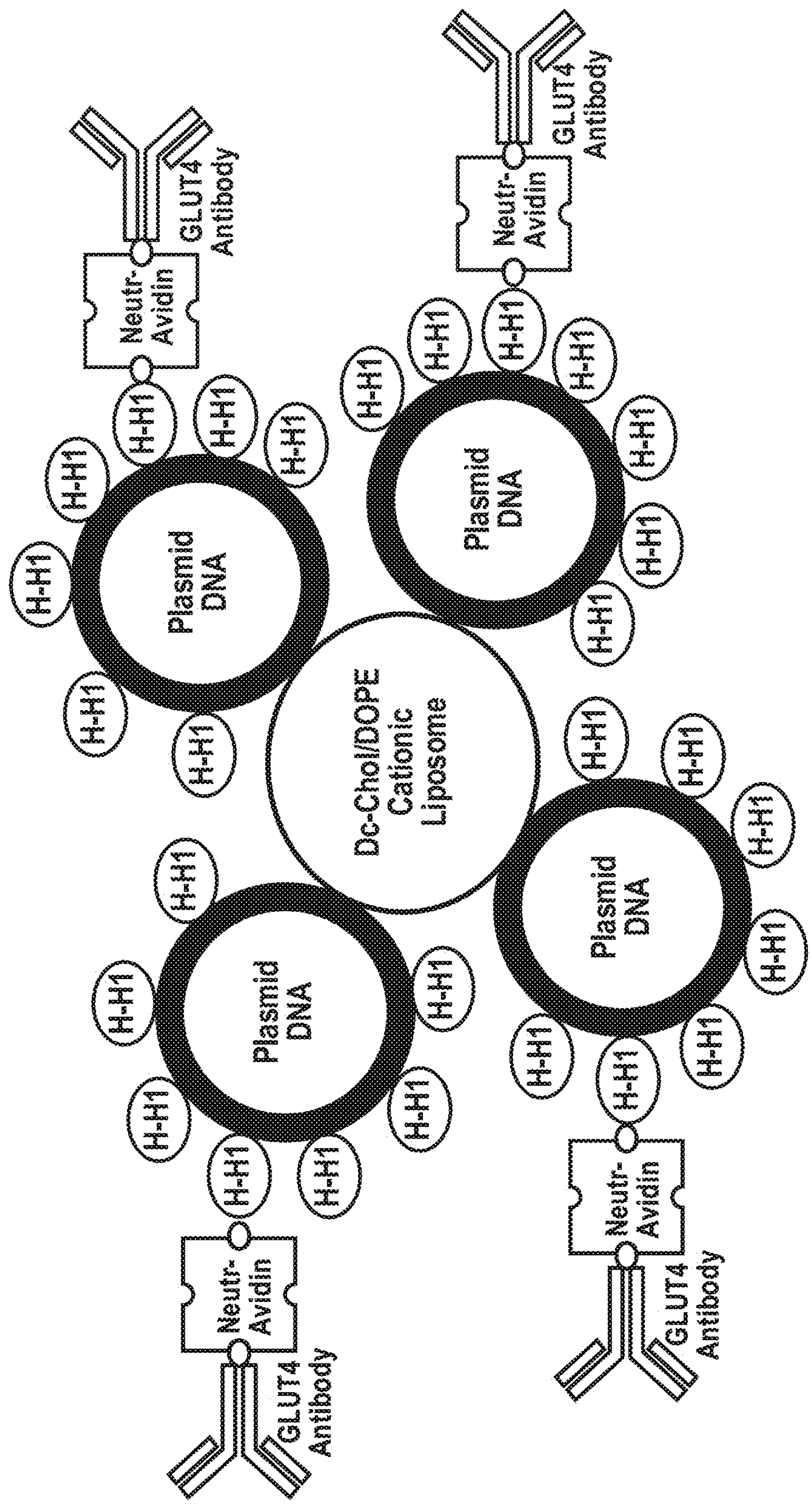
FIG. 3 is a schematic of the general structure of a representative platform of the disclosed compositions that were used for in vitro cell culture experiments as described in more detail below.

In some further embodiments, a plurality of binding domains and nucleic acid payloads (with associated DNA coiling or condensing elements) can be aggregated. This can be accomplished simply by having multiple biotinylated elements bound to the same avidin-based binding partner. Alternatively, there can be multiple biotinylated DNA coiling or condensing elements associated with the same nucleic acid payload, each of which is bound to a different avidin-based binding partner, which in turn is bound to a different binding domain. This aggregation can be further promoted by inclusion in the composition of one or more particles, such as liposomes, which can associate with multiple nucleic acid payloads. For example, as illustrated in FIG. 3, multiple nucleic acid plasmid payloads are associated with a cationic liposome structure. Each plasmid is in turn associated with a plurality of histone proteins, a portion of which are biotinylated. The biotinylated histones are bound to biotinylated binding domains (e.g., anti-GLUT4 antibodies) by mutual binding to neutravidin. The generation of such exemplary composition is described in more detail below.

Accordingly, in some embodiments, the disclosed composition can further comprise a cationic particle, such as a liposome, that can further associate and/or aggregate with the nucleic acid payload. Cationic liposomes are known and can be readily constructed by persons of ordinary skill in the art to facilitate proper aggregation and/or association with the nucleic acid payload. In some illustrative, non-limiting embodiments the liposome can comprise one or more lipids selected from DC-Cholesterol·HCl,3b-[N—(N',N'-dimethylaminoethane)-caramoyl]cholesterol hydrochloride ("DC-Chol"), 1,2-dioleoyl-sn-glycero-3-phosphoethanolamine ("DOPE"), 1,2-di-O-octadecenyl-3-trimethylammonium ("DOTMA"), N-[1-(2,3-Dioleoyloxy) propyl]-N,N,N-trimethylammonium propane ("DOTAP"), dimethyldioctadecylammonium bromide ("DDAB"), 1,2-dimyristoyl-3-trimethylammonium-propane ("DMTAP"), 1,2-dioleoyl-3-dimethylammonium-propane ("DODAP"), cholesteryl hemisuccinate ("CHEMS") and cholesterol ("CHOL"), 2,3-dioleyloxy-N-[2 (sperminecarboxamido)ethyl]-N,N-dimethyl-1-propanaminium ("DOSPA"), Di-octadecyl-amido-glycyl-spermine ("DOGS"), dioleoylphosphatidylcholine ("DOPC"), and the like. In some embodiments, the liposome further comprises polyethylene glycol ("PEG").

Figure 8:
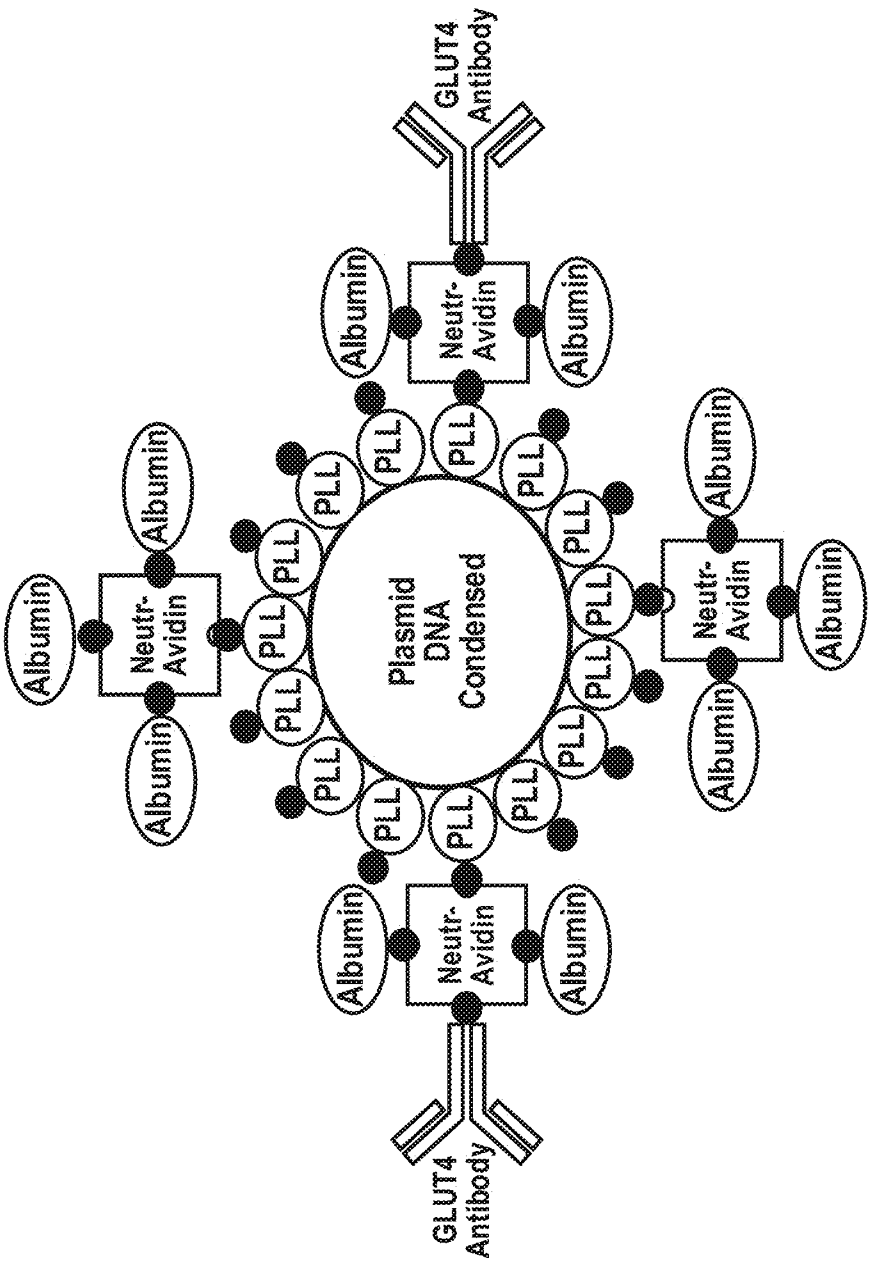
FIG. 8 is a schematic of the general structure and components of another aspect of the disclosed composition, which was for the in vivo experiments as described in more detail below.

In another exemplary embodiment, illustrated in FIG. 8, a plasmid DNA payload is associated with a plurality of PLL cationic moieties, which are biotinylated. The biotinylated PLL moieties are bound to the binding domains (e.g., anti-GLUT4 antibodies) by mutual association with the same neutravidin binding partner.

In additional embodiments, the composition further comprises albumin, which can contribute to the enhanced expression of the nucleic acid payloads. As described in more detail below, recent evidence has shown that albumin can enhance protein expression from delivered DNA/liposomal vectors. Among other reasons, albumin is believed to enhance delivery of the composition to the target cells, including enhancing endosomal escape and nuclear uptake of the nucleic acid payload. Albumin, which is negatively charged, can bind to positively charged liposomes that are associated with the nucleic acid payloads. In other embodiments where biotin and avidin-based binding partners are used for conjugation, the albumin can be biotinylated. Thus, a positively charged liposome is not a prerequisite for efficacy of albumin. This is illustrated in FIG. 8.

In one aspect, the disclosure provides the compositions described herein for use in treating a disease, wherein the disease is treatable by delivery of a payload to a cell that expresses GLUT4. Applicable diseases encompassed by this aspect, in addition to other elements of "treating" as used herein, are described in more detail below. In some embodiments, the use is for treating a disease or condition in a subject with a genetic mutation in a gene encoding dystrophin protein. In some embodiments, the compositions described herein are for use in treating of Duchenne muscular dystrophy ("DMD") or Becker muscular dystrophy ("BMD"), which are described in more detail above and below. In these embodiments, the payload of the disclosed compositions can comprise a nucleic acid that encodes full-length (e.g., wildtype) dystrophin protein, or a functional fragment thereof (e.g., about 80%, 85%, 90%, 95%, 98%), or a variant thereof with at least about 90%, 95%, or 98% amino acid sequence identity to a wildtype sequence. In some embodiments, variation in sequence identity from a wildtype sequence results from conservative substitutions that do not significantly affect protein function. In some embodiments, the use can further comprise administering to the subject insulin to increase the accessible GLUT4 target and targeting of the payload.

Methods

The disclosure also encompasses methods of using and making the disclosed compositions.

In one aspect, the disclosure provides a method of targeting a payload (e.g., therapeutic payload) for delivery to a cell that expresses GLUT4. The method comprises contacting the cell with any embodiment of the disclosed composition, e.g., as recited above.

In some embodiments, the method further comprises contacting the cell with insulin prior to contacting the cell with the composition. As described above, GLUT4 is highly expressed in striated muscle and fat tissue, in addition in cells within certain areas of the brain, including the hippocampus and cerebellum. GLUT4 mostly resides in intracellular GLUT4 storage vesicles (GSV). However, following insulin binding to the insulin receptor (in insulin-sensitive cells including skeletal muscle, heart and fat cells and some neurons), a signaling pathway is activated, leading to GLUT4 translocation to the plasma membrane. See, e.g., Klip, A, et al., 30 sweet years of GLUT4. 2019, REV119.008351, incorporated herein by reference in its entirety. Thus, in some embodiments, insulin is contacted to the cell at least about 10 minutes (such as about 10, 15, 20, 25, 30, 35, 40, 45, 50, 55, 60, 80, 90, 120 minutes or more) prior to contacting the cell with the composition.

In some embodiments, the cell is a skeletal muscle cell, a cardiac muscle cell, a smooth muscle cell, an adipose tissue cell, a hippocampal cell, or a cerebellum cell.

As indicated above, the payload (e.g., therapeutic payload) can be any composition that improves or alters the phenotype of the target cell. In some embodiments, the therapeutic payload is a nucleic acid, such as a transgene that provides for expression of a desired protein in the cell. An illustrative embodiment is a transgene encoding dystrophin, or a functional fragment thereof, to provide for expression of a dystrophin protein in the cell. Accordingly, in some embodiments, the method is characterized as a method of expressing, or increasing expression of, functional dystrophin protein in the cell, or increasing expression of, a functional fragment of dystrophin protein in the cell. The increase can be any expression level from a starting point of no expression prior to performance of the method. In some embodiments, the cell can have residual (i.e., detectable) expression of the dystrophin protein or a functional fragment thereof. In some embodiments, the cell can express dystrophin protein or a functional fragment thereof at a level that is at least about 0.01%, 0.025%, 0.05%, 0.1%, 1%, 2.5%, 5%, 10%, 25%, 20%, 25%, 30%, 35%, 40%, 45%, 50%, 55%, 60%, 65%, 70%, 75%, 80%, 85%, 90%, 95%, 100%, or more as compared to a similar cell (e.g., from a same tissue source) that has an intact wild-type gene encoding dystrophin. In some embodiments, the cell is a muscle cell.

In other embodiments, the cell is a cancer cell that expressed GLUT4 on the surface. Non-limiting examples of such cancer cells include melanoma cells, prostate cancer cells, cancer cells of muscle tissue, such as rhabdomyosarcoma cell, and breast cancer cells. In such embodiments, the therapeutic payload can be any anti-cancer therapeutic payload, such as a radioisotope or other toxin.

The method can be performed in vitro. Alternatively, the method can be an in vivo method directed to treatment of a disease associated with dysfunction of cells that express GLUT4, either constitutively or transiently, on the surface. The in vivo method comprises administering an effective amount of the disclosed composition to the subject in need thereof.

As used herein, the term “treat” refers to medical management of a disease, disorder, or condition (e.g., muscular dystrophy, such as Duchenne muscular dystrophy (DMD) or Becker muscular dystrophy (BMD) or cancer) of a subject (e.g., a human or non-human mammal, such as another primate, horse, dog, mouse, rat, guinea pig, rabbit, and the like). Treatment can encompass any indicia of success in the treatment or amelioration of a disease or condition (e.g., DMD, BMD, or cancer), including any parameter such as abatement, remission, diminishing of symptoms or making the disease or condition more tolerable to the patient, slowing in the rate of degeneration or decline, or making the degeneration less debilitating. In non-limiting examples, the term “treat” in the context of DMD can encompass slowing or inhibiting the progression of muscle loss or weakness; stabilizing or increasing muscle strength, muscle control, or motor skills; reducing muscle fatigue; stabilizing or improving diaphragm function; stabilizing or improving cardiac output, etc. In non-limiting examples, the term “treat” in the context of cancer can encompass slowing or inhibiting the rate of cancer growth, or reducing the likelihood of recurrence, compared to not having the treatment. In some embodiments, the treatment encompasses resulting in some detectable degree of cancer cell death in the patient. The treatment or amelioration of symptoms can be based on objective or subjective parameters, including the results of an examination by a physician. Accordingly, the term “treating” includes the administration of the compositions of the present disclosure to alleviate, or to arrest or inhibit development of the symptoms or conditions associated with disease or condition (e.g., DMD, BMD, or cancer). The term “therapeutic effect” refers to the amelioration, reduction, or elimination of the disease or condition, symptoms of the disease or condition, or side effects of the disease or condition in the subject. The term “therapeutically effective” refers to an amount of the composition that results in a therapeutic effect and can be readily determined.

As indicated above, the method can comprise administering to the subject a therapeutically effective amount of the disclosed composition. As indicated, the nucleic acid payload is typically configured for expression in the target cell, e.g., being operatively linked to an appropriate promoter. An effective amount is an amount that provides results in a beneficial change in phenotype. A benefit to having a cell specific promoter, e.g., a muscle specific promoter, is that it will confer additional specificity to that already provided by the GLUT4 targeting of the binding domain.

In some embodiments, the method of treatment is combined or coordinated with other therapeutic strategies. Any other therapeutic strategy addressing conditions associated with mutated or aberrant dystrophin expression is contemplated in this combinatorial aspect. In the context of cancers expressing GLUT4, the other cancer strategy can be a cancer immunotherapy that utilizes immunomodulatory compositions (e.g., antibodies, immune cells, cytokines, etc.), which may boost the subject’s own immune response against the cancer target. Such immune-therapies include adoptive immune cell therapies, including CAR T-cells, immune checkpoint inhibitor therapies, cancer vaccines, and the like.

The methods of treatment can incorporate the disclosed composition to address a number of conditions associated with cells expressing GLUT4. For example, the diseases that can be addressed with administration of the disclosed composition include skeletal muscle diseases such as: the muscular dystrophies (myotonic dystrophy (Steinert disease), Duchenne muscular dystrophy, Becker muscular dystrophy, limb-girdle muscular dystrophies, facioscapulohumeral muscular dystrophy, congenital muscular dystrophy, oculopharyngeal muscular dystrophy, distal muscular dystrophy and Emery-Dreifuss muscular dystrophy), other myopathies such as the inflammatory myopathies (for example polymyositis, dermatomyositis and inclusion-body myositis), myopathies due to endocrine abnormalities (hyperthyroid and hypothyroid myopathies), diseases causing muscle atrophy, such as cancer cachexia and sarcopenia, myotonia congenital, paramyotonia congenital, central core disease, nemaline myopathy, myotubular myopathy periodic paralysis, RYR-1 myopathies, and the inflammatory myopathies (for example polymyositis, dermatomyositis and inclusion-body myositis). The disclosed method can also be applied to treat the motor neuron diseases (for example amyotrophic lateral sclerosis (ALS), infantile progressive spinal muscular atrophy (Type 1—Werdnig-Hoffmann disease), intermediate spinal muscular atrophy (Type 2), juvenile spinal muscular atrophy (Type 3—Kugelberg-Welander disease), adult spinal muscular atrophy (Type 4) and spinal-bulbar muscular atrophy (Kennedy disease)), diseases of the neuromuscular junction such as myasthenia gravis, Lambert-Eaton (myasthenic) syndrome and congenital myasthenic syndromes, diseases of the peripheral nerves such as Charcot-Marie-Tooth disease, Friedreich's ataxia and Derjerine-Sottas disease, cardiomyopathies, metabolic diseases affecting muscle for example phosphorylase deficiency (McArdle disease), acid maltase deficiency (Pompe disease), phosphofructokinase deficiency (Tarui disease), debrancher enzyme deficiency (Cori or Forbes disease), mitochondrial myopathy, carnitine deficiency, carnitine palmityl transferase deficiency, phosphoglycerate kinase deficiency, phosphoglycerate mutase deficiency, lactate dehydrogenase deficiency and myoadenylate deaminase deficiency), and diseases affecting adipose tissue such as diabetes, adipose dolorosa, congenital generalized lipodystrophy (Berardinelli-Seip congenital lipodystrophy), familial partial lipodystrophy, familial lipoprotein lipase deficiency, neutral lipid storage disease and Chanarin-Dorfman syndrome. Because GLUT4 is expressed in the hippocampus and cerebellum, brain disorders including Alzheimer's disease, ataxia telangiectasia, NBIA (neurodegeneration with brain iron accumulation), Fahr's syndrome, Barth syndrome, and Parkinson's disease can be treated using the disclosed compositions. Finally, since GLUT4 is overexpressed in several cancers, the disclosed compositions can be used to target and treat malignant melanoma and prostate cancer, as well as cancers affecting muscle such as rhabdomyosarcoma.

In a specific aspect, the disclosure provides a method of treating a disease or condition in a subject with a genetic mutation in a gene encoding dystrophin protein. The method comprises administering to a subject a therapeutically effective amount of a composition comprising:

- a binding domain that specifically binds glucose transporter 4 ("GLUT4") protein, and
- a therapeutic payload conjugated to the binding domain, wherein the therapeutic payload comprises a nucleic acid with a promoter sequence operatively linked to a sequence encoding a dystrophin protein, or a functional fragment thereof.

In some embodiments, the subject has or is a genetic carrier of Duchenne muscular dystrophy ("DMD"). As described above, Duchenne muscular dystrophy (DMD) is a debilitating sex-linked disease resulting from aberrant dystrophin protein (or aberrant dystrophin protein expression). As a sex-linked disease, DMD mostly affects males and typically manifests first with muscle loss in the legs and pelvis, followed by the arms. Cases can progress to where the subject experiences difficulty breathing and poor cardiac output. Affected subjects ultimately have a significantly shortened life-span due to the extensive loss and degradation. In some embodiments, the subject has or is a genetic carrier of Becker muscular dystrophy ("BMD"). Becker muscular dystrophy ("BMD") is related to DMD in that it also results from mutations in the dystrophin gene. Becker muscular dystrophy ("BMD"), however, follows a milder course of symptoms compared to DMD likely because there are relatively higher levels of remaining dystrophin function in BDM subjects compared to DMD subjects due to the location of the mutation in the dystrophin gene.

Exemplary elements of the composition are described in more detail above and are applicable to this aspect. In some embodiments, the binding domain is an antibody, or fragment or derivative thereof, that specifically binds to GLUT4. Such antibodies, or fragments or derivatives thereof, are described in more detail above. In some embodiments, the antibody, or fragment or derivative thereof, specifically binds to the first extracellular domain of GLUT4. The domain and particular epitopes therein are described in more detail above. In some embodiments, the binding domain specifically binds to a first extracellular loop domain of GLUT4. In some embodiments, the first extracellular loop domain of GLUT4 comprises an amino acid sequence with at least about 80% sequence identity (e.g., at least about 80%, at least about 85%, at least about 90%, at least about 92%, at least about 94%, at least about 96%, at least about 98%, and 100% sequence identity) to the sequence set forth in SEQ ID NO:2, which is a subdomain of a human GLUT4 first extracellular loop domain. In some embodiments, the GLUT4 first extracellular loop domain comprises an amino acid sequence with at least about 80% sequence identity (e.g., at least about 80%, at least about 85%, at least about 90%, at least about 92%, at least about 94%, at least about 96%, at least about 98%, and 100% sequence identity) to the sequence set forth in SEQ ID NO:1, which is a representative human GLUT4 first extracellular loop domain. In some embodiments, the binding domain specifically binds to a subdomain of the first extracellular loop domain of GLUT4 that comprises a sequence with at least 80% sequence identity (e.g., at least about 80%, at least about 85%, at least about 90%, at least about 92%, at least about 94%, at least about 96%, at least about 98% sequence identity) to the sequence set forth in SEQ ID NO:2.

In some embodiments, the binding domain is a monoclonal antibody that binds to GLUT4 as described above. In some embodiments, the binding domain is an antibody fragment or antibody derivative. The antibody fragment or antibody derivative can be or comprise a single chain antibody, an Fab fragment, an F(ab)2 fragment, a $V_HH$ fragment, a $V_{NAR}$ fragment, or a nanobody. The single chain antibody can be a single chain variable fragment (scFv) or a single-chain Fab fragment (scFab).

In some embodiments, the antibody, or fragment or derivative thereof, is biotinylated.

The nucleic acid in this method aspect can be any nucleic acid payload as described above. For example, the nucleic acid is in linear form, plasmid form, or minicircle form.

In some embodiments, the composition further comprises a histone protein or a plurality of histone proteins associated with the nucleic acid. In some embodiments, the histone protein or at least a portion of the plurality of histone proteins is biotinylated.

In some embodiments, the composition further comprises a liposome associated with the nucleic acid. Elements of liposomes are described in more detail above and are applicable to this aspect of the disclosure. In some embodiments, the liposome comprises one or more lipids selected from DC-Cholesterol·HCl,3b-[N—(N',N'-dimethylaminoethane)-caramoyl]cholesterol hydrochloride ("DC-Chol"), 1,2-dioleoyl-sn-glycero-3-phosphoethanolamine ("DOPE"), 1,2-di-O-octadecenyl-3-trimethylammonium ("DOTMA"), N-[1-(2,3-Dioleoyloxy) propyl]-N,N,N-trimethylammonium propane ("DOTAP"), dimethyldioctadecylammonium bromide ("DDAB"), 1,2-dimyristoyl-3-trimethylammonium-propane ("DMTAP"), 1,2-dioleoyl-3-dimethylammonium-propane ("DODAP"), cholesteryl hemisuccinate ("CHEMS") and cholesterol ("CHOL"), 2,3-dioleyloxy-N-[2 (sperminecarboxamido)ethyl]-N,N-dimethyl-1-propanaminium ("DOSPA"), Di-octadecyl-amido-glycyl-spermine ("DOGS"), dioleoylphosphatidylcholine ("DOPC"), and the like. In some embodiments, the liposome further comprises polyethylene glycol ("PEG").

In some embodiments, the composition comprises a plurality of cationic peptide moieties associated with the nucleic acid, thereby resulting in condensed nucleic acid. In some embodiments, the cationic moieties are or comprise poly-L-Lysine ("PLL"), linear Polyethylenimine ("LPEI"), branched Polyethylenimine ("BPEI"), chitosan, spermidine and spermine, Polyamidoamine ("PAMAM"), poly(2-dimethylaminoethyl methacrylate) ("PDMAEMA"), Poly(beta-amino ester) s ("PBAEs"), poly {N—[N-(2-aminoethyl)-2-aminoethyl]aspartamide ("PAsp (DET)"), poly(2-aminoethyl ethylene phosphate ("PPEEA"), and the like. In some embodiments, at least a portion of the plurality the cationic peptide moieties is biotinylated.

In some embodiments, the composition further comprises albumin. In some embodiments, at least a portion of the albumin is biotinylated.

In some embodiments, the antibody, or fragment or derivative thereof, is biotinylated and the composition further comprises neutravidin.

In some embodiments, the encoded dystrophin protein is a substantially full length human dystrophin protein. In some embodiments, the full length human dystrophin protein has an amino acid sequence with at least 80% sequence identity to the sequence set forth in SEQ ID NO:5.

The subject can be a mammal, such as a human, non-human primate, rat, mouse, rabbit, cat, dog, and the like. In certain embodiments, the subject is a human.

Formulation and Administration

The disclosure also encompasses formulations appropriate for methods of administration for application to in vivo therapeutic settings in subjects (e.g., mammalian subjects with DMD, BMD, cancer, or the conditions described above). According to skill and knowledge common in the art, the disclosed compositions can be formulated with appropriate carriers and non-active binders, and the like, for administration to target specific cells. Because the compositions comprise binding domains that confer target cell specificity, the compositions can be formulated for direct or systemic administration according to skill and knowledge in the art.

Illustrative Anti-GLUT4 Antibodies.

Anti-GLUT4 antibodies that bind the extracellular domain of human GLUT4 are known (see, e.g., Tucker et al, Proc. Natl. Acad. Sci. 115: E4990-E4999, published online May 16, 2018). In a further aspect, provided herein are monoclonal antibodies that bind a human GLUT4 peptide GRQGPEGPSSI (SEQ ID NO:2). Thus, in certain embodiments, the disclosure provides an anti-GLUT4 antibody, or fragment or derivative thereof comprising a heavy chain variable region ($V_H$) and a light chain variable region ($V_L$). In some aspects, the $V_H$ comprises a CDR1 comprising a sequence (D/E)Y(S/T)(I/M)H (SEQ ID NO: 96), a CDR2 comprising a sequence WINTE(S/T)G(D/E)$X_1$(T/S) YADDFKG (SEQ ID NO: 97), and a CDR3 comprising a sequence R$X_2X_3$Y (SEQ ID NO: 98); and the $V_L$ comprises a CDR1 comprising a sequence (R/K)(A/S)SQS L/V)$X_4X_5$ (N/S) (SEQ ID NO: 99), a CDR2 comprising a sequence (V/A)SNR(F/Y)(S/T) (SEQ ID NO: 100), and a CDR3 comprising a sequence QD$X_6X_7X_8$P T (SEQ ID NO: 101). In some embodiments, $X_1$ is P or T; $X_2$, is A, F, S, or G; $X_3$ is A, D, E, or G; $X_4$ is S, V, N, or T; $X_5$ is N, H, R, K, or T; $X_6$ is R, Y, S, T, or K; $X_7$ is H N, E, T, Y, or S; or $X_8$ is V, S, L or I.

Accordingly, in some embodiments, the anti-GLUT4 antibody, or fragment or derivative thereof comprises at least one, two, three, four, five, or six CDRs selected from (a) a VH-CDR1 comprising a sequence (D/E)Y(S/T)(I/M) H (SEQ ID NO: 96); (b) a VH-CDR2 comprising a sequence WINTE(S/T)G(D/E)$X_1$(T/S)YADDFKG (SEQ ID NO: 97); (c) a VH-CDR3 comprising a sequence R$X_2X_3$Y (SEQ ID NO: 98); (d) a VL-CDR1 comprising a sequence (R/K)(A/S)SQS(L/V)$X_4X_5$ (N/S) (SEQ ID NO: 99); (e) a VL-CDR2 comprising a sequence (V/A)SNR(F/Y)(S/T) (SEQ ID NO: 100); and (f) a VL-CDR3 comprising a sequence QD$X_6X_7X_8$P T (SEQ ID NO: 101). In some embodiments, $X_1$ is P or T; $X_2$, is A, F, S, or G; $X_3$ is A, D, E, or G; $X_4$ is S, V, N, or T; $X_5$ is N, H, R, K, or T; $X_6$ is R, Y, S, T, or K; $X_7$ is H N, E, T, Y, or S; or $X_8$ is V, S, L or I.

In some embodiments, the anti-GLUT4 antibody, or fragment or derivative thereof comprises at least one, two, three, four, five, or six CDRs selected from (a) a VH-CDR1 having a sequence selected from SEQ ID NOs: 10-17; (b) a VH-CDR2 having a sequence selected from SEQ ID NOs: 18-25; (c) a VH-CDR3 having a sequence selected from LDF and SEQ ID NOs: 27-33; (d) a VL-CDR1 having a sequence selected from SEQ ID NOs: 34-41; (e) a VL-CDR2 having a sequence selected from SEQ ID NOs: 42-49; and (f) a VL-CDR3 having a sequence selected from SEQ ID NOs: 50-57.

In some embodiments, the disclosure provides an anti-GLUT4 antibody, or fragment or derivative thereof comprising a heavy chain variable region ($V_H$) and a light chain variable region ($V_L$). In some embodiments, the $V_H$ comprises a VH-CDR1 having a sequence selected from SEQ ID NOs: 10-17, a VH-CDR2 having a sequence selected from SEQ ID NOs: 18-25, and a VH-CDR3 having a sequence selected from LDF and SEQ ID NOs: 27-33; and the $V_L$ comprises a VL-CDR1 having a sequence selected from SEQ ID NOs: 34-41, a VL-CDR2 having a sequence selected from SEQ ID NOs: 42-49, and a VL-CDR3 having a sequence selected from SEQ ID NOs: 50-57.

In some embodiments, the $V_H$ comprises a VH-CDR1 having a sequence set forth in SEQ ID NO 10, a VH-CDR2 having a sequence set forth in SEQ ID NO:18, and a VH-CDR3 having a sequence LDF; and the $V_L$ comprises a VL-CDR1 having a sequence set forth in SEQ ID NO:34, a VL-CDR2 having a sequence set forth in SEQ ID NO:42, and a VL-CDR3 having a sequence set forth in SEQ ID NO:50.

In some embodiments, the $V_H$ comprises a VH-CDR1 having a sequence set forth in SEQ ID NO:11, a VH-CDR2 having a sequence set forth in SEQ ID NO:19, and a VH-CDR3 having a sequence set forth in SEQ ID NO:27; and the $V_L$ comprises a VL-CDR1 having a sequence set forth in SEQ ID NO:35, a VL-CDR2 having a sequence set forth in SEQ ID NO:43, and a VL-CDR3 having a sequence set forth in SEQ ID NO:51.

In some embodiments, the $V_H$ comprises a VH-CDR1 having a sequence set forth in SEQ ID NO:12, a VH-CDR2 having a sequence set forth in SEQ ID NO:20, and a VH-CDR3 having a sequence set forth in SEQ ID NO:28; and the $V_L$ comprises a VL-CDR1 having a sequence set forth in SEQ ID NO:36, a VL-CDR2 having a sequence set forth in SEQ ID NO:44, and a VL-CDR3 having a sequence set forth in SEQ ID NO:52.

In some embodiments, the $V_H$ comprises a VH-CDR1 having a sequence set forth in SEQ ID NO 13, a VH-CDR2 having a sequence set forth in SEQ ID NO:21, and a VH-CDR3 having a sequence set forth in SEQ ID NO:29; and the $V_L$ comprises a VL-CDR1 having a sequence set forth in SEQ ID NO:37, a VL-CDR2 having a sequence set forth in SEQ ID NO:45, and a VL-CDR3 having a sequence set forth in SEQ ID NO:53.

In some embodiments, the $V_H$ comprises a VH-CDR1 having a sequence set forth in SEQ ID NO:14, a VH-CDR2 having a sequence set forth in SEQ ID NO:22, and a VH-CDR3 having a sequence set forth in SEQ ID NO:30; and the $V_L$ comprises a VL-CDR1 having a sequence set forth in SEQ ID NO:38, a VL-CDR2 having a sequence set forth in SEQ ID NO:46, and a VL-CDR3 having a sequence set forth in SEQ ID NO:54

In some embodiments, the $V_H$ comprises a VH-CDR1 having a sequence set forth in SEQ ID NO:15, a VH-CDR2 having a sequence set forth in SEQ ID NO:23, and a VH-CDR3 having a sequence set forth in SEQ ID NO:31; and the $V_L$ comprises a VL-CDR1 having a sequence set forth in SEQ ID NO:39, a VL-CDR2 having a sequence set forth in SEQ ID NO:47, and a VL-CDR3 having a sequence set forth in SEQ ID NO:55

In another embodiment, the $V_H$ comprises a VH-CDR1 having a sequence set forth in SEQ ID NO:16, a VH-CDR2 having a sequence set forth in SEQ ID NO:24, and a VH-CDR3 having a sequence set forth in SEQ ID NO:32; and the $V_L$ comprises a VL-CDR1 having a sequence set forth in SEQ ID NO:40, a VL-CDR2 having a sequence set forth in SEQ ID NO:48, and a VL-CDR3 having a sequence set forth in SEQ ID NO:56.

In yet another embodiment, the $V_H$ comprises a VH-CDR1 having a sequence set forth in SEQ ID NO:17, a VH-CDR2 having a sequence set forth in SEQ ID NO:25, and a VH-CDR3 having a sequence set forth in SEQ ID NO:33; and the $V_L$ comprises a VL-CDR1 having a sequence set forth in SEQ ID NO:41, a VL-CDR2 having a sequence set forth in SEQ ID NO:49, and a VL-CDR3 having a sequence set forth in SEQ ID NO:57.

In certain embodiments, substitutions, insertions, or deletions may occur within one or more CDRs without substantially reducing the ability of the antibody to bind antigen. For example, conservative alterations (e.g., conservative substitutions as provided herein) that do not substantially reduce binding affinity may be made in CDRs. In certain embodiments, each CDR provided above either is unaltered, or contains one, two, three or four amino acid substitutions.

In some embodiments, the anti-GLUT4 antibody, or fragment or derivative thereof further comprises CDRs as defined in the preceding paragraphs in this section and a framework regions sequence having at least 90% identity, or at least 95% identity to a human immunoglobulin framework sequences. In some embodiments, each of framework region 1 (FR1), framework region 2 (FR2), framework region 3 (FR3), and framework region 4 (FR4) have at least 90% identity, or at least 95% identity to a corresponding human FR1, FR2, FR3, or FR4 sequence.

An antibody as defined above that binds a human GLUT4 peptide of amino acid sequence GRQGPEGPSSI (SEQ ID NO:2) can be used to deliver a payload as described in any of the embodiments detailed herein.

ILLUSTRATIVE EMBODIMENTS

Illustrative embodiments include, but are not limited, to the following:

In some embodiments, the disclosure provides a composition comprising an antibody, or fragment or derivative thereof, that specifically binds to glucose transporter 4 ("GLUT4") protein, and a therapeutic payload conjugated to the antibody, or fragment or derivative thereof. In one embodiment, the antibody, or fragment or derivative thereof, specifically binds to a first extracellular loop domain of GLUT4. In some aspects, the first extracellular loop domain of GLUT4 comprises an amino acid sequence with at least 80% identity to the sequence INAPQKVIEQSYNETWLGRQGPEGPSSIPPGTLTTL (SEQ ID NO: 1). In one aspect, the first extracellular loop domain of GLUT4 comprises an amino acid sequence with at least 80% identity to the sequence GRQGPEGPSSI (SEQ ID NO:2). In some aspects, the antibody, or fragment or derivative thereof, specifically binds to a subdomain of the first extracellular loop domain of GLUT4 that comprises an amino acid sequence with at least 80% identity to the sequence GRQGPGGPDSI (SEQ ID NO:4). In one aspect, the antibody, or fragment or derivative thereof, specifically binds to a subdomain of the first extracellular loop domain of GLUT4 that comprises a sequence with at least 80% identity to the sequence GRQGPEGPSSI (SEQ ID NO:2).

In some embodiments, the antibody is a monoclonal antibody. In one embodiment, the antibody fragment or antibody derivative is or comprises a single chain antibody, an Fab fragment, an F(ab)2 fragment, a $V_H$H fragment, a $V_{NAR}$ fragment, or a nanobody. In some aspects, the single-chain antibody is a single chain variable fragment (scFv), or a single-chain Fab fragment (scFab).

In some embodiments, the antibody, or fragment or derivative thereof, is biotinylated.

In some embodiments, the therapeutic payload comprises a nucleic acid, a protein or peptide, a lipid, a small molecule pharmaceutical, or a radioisotope. In one embodiment, the therapeutic payload comprises a nucleic acid, wherein the nucleic acid is selected from DNA, mRNA, siRNA, and shRNA. In one embodiment, the therapeutic payload comprises a nucleic acid, wherein the nucleic acid comprises an open reading frame operatively linked to a promoter sequence. In one embodiment, the therapeutic payload comprises a nucleic acid in linear form, a nucleic acid in plasmid form, or a nucleic acid in minicircle form.

In some embodiments, the composition further comprises a histone protein or a plurality of histone proteins associated with the nucleic acid. In one aspect, the histone protein or at least a portion of the plurality of histone proteins is biotinylated.

In some embodiments, the composition further comprises a liposome associated with the nucleic acid. In one aspect, the liposome comprises one or more lipids selected from DC-Cholesterol·HCl,3b-[N—(N',N'-dimethylaminoethane)-caramoyl]cholesterol hydrochloride ("DC-Chol"), 1,2-dioleoyl-sn-glycero-3-phosphoethanolamine ("DOPE"), 1,2-di-O-octadecenyl-3-trimethylammonium ("DOTMA"), N-[1-(2,3-Dioleoyloxy) propyl]-N,N,N-trimethylammonium propane ("DOTAP"), dimethyldioctadecylammonium bromide ("DDAB"), 1,2-dimyristoyl-3-trimethylammonium-propane ("DMTAP"), 1,2-dioleoyl-3-dimethylammonium-propane ("DODAP"), cholesteryl hemisuccinate ("CHEMS") and cholesterol ("CHOL"), 2,3-dioleyloxy-N-[2 (sperminecarboxamido)ethyl]-N,N-dimethyl-1-propanaminium ("DOSPA"), Di-octadecyl-amido-glycyl-spermine ("DOGS"), dioleoylphosphatidylcholine ("DOPC"), and the like. In one aspect, the liposome further comprises polyethylene glycol ("PEG").

In some embodiments, the composition further comprises a plurality of cationic peptide moieties associated with the nucleic acid, thereby resulting in condensed nucleic acid. In one embodiment, the cationic peptide moieties are or comprise poly-L-Lysine ("PLL"), linear Polyethylenimine ("LPEI"), branched Polyethylenimine ("BPEI"), chitosan, spermidine and spermine, Polyamidoamine ("PAMAM"), poly(2-dimethylaminoethyl methacrylate) ("PDMAEMA"), Poly(beta-amino ester) s ("PBAEs"), poly {N—[N-(2-aminoethyl)-2-aminoethyl]aspartamide ("PAsp (DET)"), poly (2-aminoethyl ethylene phosphate ("PPEEA"), and the like. In one aspect, at least a portion of the plurality the cationic peptide moieties is biotinylated.

In some embodiments, the composition of the present disclosure further comprises albumin. In one embodiment, at least a portion of the albumin is biotinylated.

In some embodiment, the antibody, or fragment or derivative thereof, is biotinylated and the composition further comprises neutravidin.

In some embodiment, the therapeutic payload comprises a nucleic acid with a promoter sequence operatively linked to a sequence encoding a dystrophin protein, or a functional fragment thereof. In one embodiment, the dystrophin protein is a substantially full-length human dystrophin protein. In one aspect, the full-length human dystrophin protein has an amino acid sequence with at least 80% sequence identity to the sequence set forth in SEQ ID NO:5.

The disclosure further provides a method of targeting a therapeutic payload for delivery to a cell that expresses GLUT4, the method comprising contacting the cell with the composition. In some embodiments, the method further comprises contacting the cell with insulin prior to contacting the cell with the composition. In one embodiment, the cell is a skeletal muscle cell, a cardiac muscle cell, a smooth muscle cell, an adipose tissue cell, a hippocampal cell, or a cerebellum cell. In one aspect, the cell is a melanoma cell, prostate cancer cell, cancer cell of muscle tissue, such as rhabdomyosarcoma cell, or a breast cancer cell.

In another aspect, the disclosure includes method of treating a disease or condition in a subject with a genetic mutation in a gene encoding dystrophin protein, comprising administering to a subject a therapeutically effective amount of a composition comprising: an antibody, or fragment or derivative thereof, that specifically binds glucose transporter 4 ("GLUT4") protein, and a therapeutic payload conjugated to the antibody, or fragment or derivative thereof, wherein the therapeutic payload comprises a nucleic acid with a promoter sequence operatively linked to a sequence encoding a dystrophin protein, or a functional fragment thereof. In some embodiments, the subject has or is a genetic carrier of Duchenne muscular dystrophy ("DMD") or Becker muscular dystrophy ("BMD").

In some embodiments, the antibody, or fragment or derivative thereof, employed in the method of treating a disease or condition described in the preceding two paragraphs specifically binds to a first extracellular loop domain of GLUT4. In one embodiment, the first extracellular loop domain of GLUT4 comprises an amino acid sequence with at least 80% identity to the sequence INAPQKVIEQSYNETWLGRQGPEGPSSIPPGTLTTL (SEQ ID NO: 1). In some aspects, the antibody, or fragment or derivative thereof, specifically binds to a subdomain of the first extracellular loop domain of GLUT4 that comprises a sequence with at least 80% identity to the sequence GRQGPEGPSSI (SEQ ID NO:2). In some embodiments, the antibody is a monoclonal antibody. In one embodiment, the antibody fragment or antibody derivative is or comprises a single chain antibody, an Fab fragment, an F(ab)2 fragment, a $V_H$H fragment, a $V_{NAR}$ fragment, or a nanobody. In some aspects, the single-chain antibody is a single chain variable fragment (scFv), or a single-chain Fab fragment (scFab). In some embodiments, the antibody, or fragment or derivative thereof, is biotinylated. In some embodiments, the nucleic acid is in linear form, plasmid form, or minicircle form. In one embodiment, the composition further comprises a histone protein or a plurality of histone proteins associated with the nucleic acid. In one aspect, the histone protein or at least a portion of the plurality of histone proteins is biotinylated. In some embodiments, the composition further comprises a liposome associated with the nucleic acid. In one embodiment, the liposome comprises one or more lipids selected from DC-Cholesterol·HCl,3b-[N—(N',N'-dimethylaminoethane)-caramoyl]cholesterol hydrochloride ("DC-Chol"), 1,2-dioleoyl-sn-glycero-3-phosphoethanolamine ("DOPE"), 1,2-di-O-octadecenyl-3-trimethylammonium ("DOTMA"), N-[1-(2,3-Dioleoyloxy) propyl]-N,N,N-trimethylammonium propane ("DOTAP"), dimethyldioctadecylammonium bromide ("DDAB"), 1,2-dimyristoyl-3-trimethylammonium-propane ("DMTAP"), 1,2-dioleoyl-3-dimethylammonium-propane ("DODAP"), cholesteryl hemisuccinate ("CHEMS") and cholesterol ("CHOL"), 2,3-dioleyloxy-N-[2 (sperminecarboxamido)ethyl]-N,N-dimethyl-1-propanaminium ("DOSPA"), Di-octadecyl-amido-glycyl-spermine ("DOGS"), dioleoylphosphatidylcholine ("DOPC"), and the like. In one aspect, the liposome further comprises polyethylene glycol ("PEG"). In some embodiments, the composition further comprises a plurality of cationic peptide moieties associated with the nucleic acid, thereby resulting in condensed nucleic acid. In one embodiment, the cationic peptide moieties are or comprise poly-L-Lysine ("PLL"), linear Polyethylenimine ("LPEI"), branched Polyethylenimine ("BPEI"), chitosan, spermidine and spermine, Polyamidoamine ("PAMAM"), poly(2-dimethylaminoethyl methacrylate) ("PDMAEMA"), Poly(beta-amino ester) s ("PBAEs"), poly {N—[N-(2-aminoethyl)-2-aminoethyl]aspartamide ("PAsp (DET)"), poly(2-aminoethyl ethylene phosphate ("PPEEA"), and the like. In one aspect, at least a portion of the plurality the cationic peptide moieties is biotinylated. In some embodiments, the composition further comprises albumin. In one embodiment, at least a portion of the albumin is biotinylated. In some embodiments, the antibody, or fragment or derivative thereof, is biotinylated and the composition further comprises neutravidin. In some embodiments, the encoded dystrophin protein is a substantially full-length human dystrophin protein. In one embodiment, the full-length human dystrophin protein has an amino acid sequence with at least 80% sequence identity to the sequence (SEQ ID NO:5). In some embodiments, the subject is a human.

In still another aspect, the disclosure provides an anti-GLUT4 antibody, or fragment or derivative thereof comprising a heavy chain variable region ($V_H$) and a light chain variable region ($V_L$), wherein: (a) the $V_H$ comprises a CDR1 comprising a sequence (D/E)Y(S/T)(I/M)H (SEQ ID NO: 96), a CDR2 comprising a sequence WINTE(S/T)G(D/E)$X_1$(T/S)YADDFKG (SEQ ID NO: 97), and a CDR3 comprising a sequence R$X_2$$X_3$Y (SEQ ID NO: 98); and (b) the $V_L$ comprises a CDR1 comprising a sequence (R/K)(A/S)SQS(L/V)$X_4$$X_5$(N/S) (SEQ ID NO: 99), a CDR2 comprising a sequence (V/A)SNR(F/Y)(S/T) (SEQ ID NO: 100), and a CDR3 comprising a sequence QD$X_6$$X_7$$X_8$PT (SEQ ID NO: 101). In some embodiments, $X_1$ is P or T; $X_2$, is A, F, S, or G; $X_3$ is A, D, E, or G; $X_4$ is S, V, N, or T; $X_5$ is N, H, R, K, or T; $X_6$ is R, Y, S, T, or K; $X_7$ is H N, E, T, Y, or S; or $X_8$ is V, S, L or I.

In yet another aspect, the disclosure includes an anti-GLUT4 antibody, or fragment or derivative thereof comprising a heavy chain variable region ($V_H$) and a light chain variable region ($V_L$), wherein: (a) the $V_H$ comprises a VH-CDR1 having a sequence selected from SEQ ID NOs: 10-17, a VH-CDR2 having a sequence selected from SEQ ID NOs: 18-25, and a VH-CDR3 having a sequence selected from LDF and SEQ ID NOs: 27-33; and (b) the $V_L$ comprises a VL-CDR1 having a sequence selected from SEQ ID NOs: 34-41, a VL-CDR2 having a sequence selected from SEQ ID NOs: 42-49, and a VL-CDR3 having a sequence selected from SEQ ID NOs: 50-57.

In some embodiments, the anti-GLUT4 antibody, or fragment or derivative thereof comprising a heavy chain variable region ($V_H$) and a light chain variable region ($V_L$), wherein: (a) the $V_H$ comprises a VH-CDR1 having a sequence set forth in SEQ ID NO 10, a VH-CDR2 having a sequence set forth in SEQ ID NO:18, and a VH-CDR3 having a sequence LDF; and the $V_L$ comprises a VL-CDR1 having a sequence set forth in SEQ ID NO:34, a VL-CDR2 having a sequence set forth in SEQ ID NO:42, and a VL-CDR3 having a sequence set forth in SEQ ID NO:50; (b) the $V_H$ comprises a VH-CDR1 having a sequence set forth in SEQ ID NO: 11, a VH-CDR2 having a sequence set forth in SEQ ID NO:19, and a VH-CDR3 having a sequence set forth in SEQ ID NO:27; and the $V_L$ comprises a VL-CDR1 having a sequence set forth in SEQ ID NO:35, a VL-CDR2 having a sequence set forth in SEQ ID NO:43, and a VL-CDR3 having a sequence set forth in SEQ ID NO:51; (c) the $V_H$ comprises a VH-CDR1 having a sequence set forth in SEQ ID NO:12, a VH-CDR2 having a sequence set forth in SEQ ID NO:20, and a VH-CDR3 having a sequence set forth in SEQ ID NO:28; and the VL comprises a VL-CDR1 having a sequence set forth in SEQ ID NO:36, a VL-CDR2 having a sequence set forth in SEQ ID NO:44, and a VL-CDR3 having a sequence set forth in SEQ ID NO: 52; (d) the $V_H$ comprises a VH-CDR1 having a sequence set forth in SEQ ID NO 13, a VH-CDR2 having a sequence set forth in SEQ ID NO:21, and a VH-CDR3 having a sequence set forth in SEQ ID NO:29; and the $V_L$ comprises a VL-CDR1 having a sequence set forth in SEQ ID NO:37, a VL-CDR2 having a sequence set forth in SEQ ID NO:45, and a VL-CDR3 having a sequence set forth in SEQ ID NO:53; (e) the $V_H$ comprises a VH-CDR1 having a sequence set forth in SEQ ID NO:14, a VH-CDR2 having a sequence set forth in SEQ ID NO: 22, and a VH-CDR3 having a sequence set forth in SEQ ID NO:30; and the $V_L$ comprises a VL-CDR1 having a sequence set forth in SEQ ID NO:38, a VL-CDR2 having a sequence set forth in SEQ ID NO:46, and a VL-CDR3 having a sequence set forth in SEQ ID NO:54; (f) the $V_H$ comprises a VH-CDR1 having a sequence set forth in SEQ ID NO:15, a VH-CDR2 having a sequence set forth in SEQ ID NO:23, and a VH-CDR3 having a sequence set forth in SEQ ID NO:31; and the $V_L$ comprises a VL-CDR1 having a sequence set forth in SEQ ID NO: 39, a VL-CDR2 having a sequence set forth in SEQ ID NO:47, and a VL-CDR3 having a sequence set forth in SEQ ID NO:55; (g) the $V_H$ comprises a VH-CDR1 having a sequence set forth in SEQ ID NO:16, a VH-CDR2 having a sequence set forth in SEQ ID NO:24, and a VH-CDR3 having a sequence set forth in SEQ ID NO:32; and the $V_L$ comprises a VL-CDR1 having a sequence set forth in SEQ ID NO:40, a VL-CDR2 having a sequence set forth in SEQ ID NO:48, and a VL-CDR3 having a sequence set forth in SEQ ID NO:56; or (h) the $V_H$ comprises a VH-CDR1 having a sequence set forth in SEQ ID NO:17, a VH-CDR2 having a sequence set forth in SEQ ID NO:25, and a VH-CDR3 having a sequence set forth in SEQ ID NO: 33; and the $V_L$ comprises a VL-CDR1 having a sequence set forth in SEQ ID NO:41, a VL-CDR2 having a sequence set forth in SEQ ID NO:49, and a VL-CDR3 having a sequence set forth in SEQ ID NO:57.

In some embodiments, the disclosure provides a composition comprising an antibody, or fragment or derivative thereof, of any one of the embodiments above described in the three preceding paragraphs, and a therapeutic payload conjugated to the antibody, or fragment or derivative thereof. In some embodiments, the antibody fragment or antibody derivative is or comprises a single chain antibody, an Fab fragment, an F(ab)2 fragment, a $V_H$H fragment, a $V_{NAR}$ fragment, or a nanobody. In one aspect, the single-chain antibody is a single chain variable fragment (scFv), or a single-chain Fab fragment (scFab). In some embodiments, the therapeutic payload comprises a nucleic acid, a protein or peptide, a lipid, a small molecule pharmaceutical, or a radioisotope. In some embodiments, the therapeutic payload comprises a nucleic acid, wherein the nucleic acid is selected from DNA, mRNA, siRNA, and shRNA. In some embodiments, the therapeutic payload comprises a nucleic acid, wherein the nucleic acid comprises an open reading frame operatively linked to a promoter sequence. In some embodiments, the therapeutic payload comprises a nucleic acid in linear form, a nucleic acid in plasmid form, or a nucleic acid in minicircle form. In some embodiments, the composition further comprises a histone protein or a plurality of histone proteins associated with the nucleic acid. In some embodiments, the composition further comprises a liposome associated with the nucleic acid. In some embodiments, the composition further comprises a plurality of cationic peptide moieties associated with the nucleic acid, thereby resulting in condensed nucleic acid. In some embodiments, the therapeutic payload comprises a nucleic acid with a promoter sequence operatively linked to a sequence encoding a dystrophin protein, or a functional fragment thereof. In one embodiment, the dystrophin protein is a substantially full-length human dystrophin protein having an amino acid sequence with at least 80% sequence identity to the sequence set forth in SEQ ID NO:5.

In some embodiments, the disclosure provides a method of targeting a therapeutic payload for delivery to a cell that expresses GLUT4, the method comprising contacting the cell with the composition comprising an anti-GLUT4 antibody, or fragment or derivative thereof as described in the preceding paragraph. In some embodiments, the method further comprises contacting the cell with insulin prior to contacting the cell with the composition. In one embodiment, the cell is a skeletal muscle cell, a cardiac muscle cell, a smooth muscle cell, an adipose tissue cell, a hippocampal cell, or a cerebellum cell. In one embodiment, the cell is a melanoma cell, prostate cancer cell, cancer cell of muscle tissue, such as rhabdomyosarcoma cell, or a breast cancer cell. In some embodiments, the subject is a human.

In some embodiments, the disclosure provides a method of treating a disease or condition in a subject with a genetic mutation in a gene encoding dystrophin protein, comprising administering to a subject a therapeutically effective amount of a composition comprising an antibody as specified in any of the embodiments above. In some embodiment, the subject has or is a genetic carrier of Duchenne muscular dystrophy ("DMD") or Becker muscular dystrophy ("BMD"). In some embodiments, the encoded dystrophin protein has at least 80% sequence identity to SEQ ID NO:5. In some embodiments, the subject is a human.

General Definitions

Unless specifically defined herein, all terms used herein have the same meaning as they would to one skilled in the art of the present disclosure. Practitioners are particularly directed to Ausubel, F. M., et al. (eds.), *Current Protocols in Molecular Biology*, John Wiley & Sons, New York (2010), Coligan, J. E., et al. (eds.), *Current Protocols in Immunology*, John Wiley & Sons, New York (2010), Mirzaei, H. and Carrasco, M. (eds.), Modern Proteomics—Sample Preparation, Analysis and Practical Applications in *Advances in Experimental Medicine and Biology*, Springer International Publishing, 2016, and Comai, L, et al., (eds.), Proteomic: Methods and Protocols in *Methods in Molecular Biology*, Springer International Publishing, 2017, for definitions and terms of art.

For convenience, certain terms employed in this description and/or the claims are provided here. The definitions are provided to aid in describing particular embodiments and are not intended to limit the claimed invention, because the scope of the invention is limited only by the claims.

The use of the term "or" in the claims is used to mean "and/or" unless explicitly indicated to refer to alternatives only or the alternatives are mutually exclusive, although the disclosure supports a definition that refers to only alternatives and "and/or."

The words "a" and "an," when used in conjunction with the word "comprising" in the claims or specification, denotes one or more, unless specifically noted.

Unless the context clearly requires otherwise, throughout the description and the claims, the words "comprise," "comprising," and the like, are to be construed in an inclusive sense as opposed to an exclusive or exhaustive sense, which is to indicate, in the sense of "including, but not limited to." Words using the singular or plural number also include the plural and singular number, respectively. The word "about" indicates a number within range of minor variation above or below the stated reference number. For example, "about" can refer to a number within a range of 10%, 9%, 8%, 7%, 6%, 5%, 4%, 3%, 2%, or 1% above or below the indicated reference number.

As used herein, the term "polypeptide" or "protein" refers to a polymer in which the monomers are amino acid residues that are joined together through amide bonds. When the amino acids are alpha-amino acids, either the L-optical isomer or the D-optical isomer can be used, the L-isomers being preferred. The term polypeptide or protein as used herein encompasses any amino acid sequence and includes modified sequences such as glycoproteins. The term polypeptide is specifically intended to cover naturally occurring proteins, as well as those that are recombinantly or synthetically produced.

One of skill will recognize that individual substitutions, deletions or additions to a peptide, polypeptide, or protein sequence which alters, adds or deletes a single amino acid or a percentage of amino acids in the sequence is a "conservatively modified variant" where the alteration results in the substitution of an amino acid with a chemically similar amino acid. Conservative amino acid substitution tables providing functionally similar amino acids are well known to one of ordinary skill in the art. The following six groups are examples of amino acids that are considered to be conservative substitutions for one another:

(1) Alanine (A), Serine(S), Threonine (T),
(2) Aspartic acid (D), Glutamic acid (E),
(3) Asparagine (N), Glutamine (Q),
(4) Arginine (R), Lysine (K),
(5) Isoleucine (I), Leucine (L), Methionine (M), Valine (V), and
(6) Phenylalanine (F), Tyrosine (Y), Tryptophan (W).

Reference to sequence identity addresses the degree of similarity of two polymeric sequences, such as protein sequences. Determination of sequence identity can be readily accomplished by persons of ordinary skill in the art using accepted algorithms and/or techniques. Sequence identity is typically determined by comparing two optimally aligned sequences over a comparison window, where the portion of the peptide or polynucleotide sequence in the comparison window may comprise additions or deletions (e.g., gaps) as compared to the reference sequence (which does not comprise additions or deletions) for optimal alignment of the two sequences. The percentage is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. Various software driven algorithms are readily available, such as BLAST N or BLAST P to perform such comparisons.

Disclosed are materials, compositions, and components that can be used for, can be used in conjunction with, can be used in preparation for, or are products of the disclosed methods and compositions. It is understood that, when combinations, subsets, interactions, groups, etc., of these materials are disclosed, each of various individual and collective combinations is specifically contemplated, even though specific reference to each and every single combination and permutation of these compounds may not be explicitly disclosed. This concept applies to all aspects of this disclosure including, but not limited to, steps in the described methods. Thus, specific elements of any foregoing embodiments can be combined or substituted for elements in other embodiments. For example, if there are a variety of additional steps that can be performed, it is understood that each of these additional steps can be performed with any specific method steps or combination of method steps of the disclosed methods, and that each such combination or subset of combinations is specifically contemplated and should be considered disclosed. Additionally, it is understood that the embodiments described herein can be implemented using any suitable material such as those described elsewhere herein or as known in the art.

Publications cited herein and the subject matter for which they are cited are hereby specifically incorporated by reference in their entireties.

EXAMPLES

The following is a description of a series of exemplary assays conducted on representative embodiments of the platform muscle-specific vector compositions to establish the utility of the platform design for efficiently delivering therapeutic payloads to muscle tissues and other tissues.

Introduction

The disclosed non-viral vector platform utilizes a GLUT4 targeting antibody (or other binding agents (e.g., antibody fragment, peptides, receptors, etc.) capable of specific binding to an extracellular domain of GLUT4. The first extracellular loop is the largest, most accessible and likely immunogenic region for targeting GLUT4 extracellularly. This domain comprises amino 45-80 in acids the mouse GLUT4 sequence; INAPQKVIEQSYNATWL-GRQGPGGPDSIPQGTLTTL (SEQ ID NO:3). The antibodies were generated against a peptide produced from amino acids 61-72 of this sequence; GRQGPGGPDSI (SEQ ID NO:4). The analogous region of the human sequence, GRQGPEGPSSI (SEQ ID NO:2), shares 83.3% homology to the mouse sequence. This sequence is predicted to not have any secondary structure, and was hypothesized to be amenable to generating antibodies that could bind to this domain of the native GLUT4 protein.

Using this platform, the GLUT4 antibody (or fragment thereof) can then be conjugated to a therapeutic gene or other drug using a wide variety of materials, such as proteins, peptides, lipids, liposomes, etc., to encapsulate the therapeutic agent, optimize its stability and bioavailability in vivo, and enhance endosomal escape and nuclear delivery (for nucleic acids) once inside the target cell. As demonstrated in the following experiments, the DNA size is not a limiting factor, allowing delivery of large genes such as full-length dystrophin (~14 Kb) and also use strong muscle-specific promoters to drive gene expression.

In Vitro Cell Culture Experiments

For the initial in vitro cell culture experiments, a Biotin-NeutrAvidin system was used to conjugate targeting antibody to a cationic liposome containing the therapeutic plasmid. This embodiment of the vector platform for in vitro experiments is shown schematically in FIG. 3. First, the plasmid is mixed with Histone H1 (H-H1), some of which is biotinylated. H-H1 is a positively charged nuclear protein that binds to the negatively charged DNA and partly condenses it. Second, the GLUT4 antibody, which is also biotinylated, is added. Third, NeutrAvidin (deglycosylated avidin), a highly specific biotin binding protein with minimal non-specific binding compared to Avidin, is added to bind the biotinylated proteins. Fourth, the proteins and DNA are mixed with cationic liposomes comprising two lipids, DC-Chol (DC-Cholesterol·HCl,3b-[N—(N',N'-dimethyl-aminoethane)-caramoyl]cholesterol hydrochloride) and DOPE (1,2-dioleoyl-sn-glycero-3-phosphoethanolamine). The DC-Chol:DOPE molar ratio is 30:70. Each of the four incubation steps described above are at room temperature for 30 min.

In initial proof-of-concept experiments, this conjugate structure was assessed for whether it could be taken up by muscle cells in vitro and the protein encoded by the DNA plasmid expressed in the cells. These experiments used a commercially available rat myoblast cell line (L6-GLUT4myc), which overexpresses GLUT4 containing a myc tag (amino acid sequence AEEQKLISEEDLLK; SEQ ID NO:9) inserted into the first extracellular loop between amino acids 66 and 67. For the initial experiments using this cell line, a commercial antibody that binds specifically to the myc tag was biotinylated.

Experiment 1

Figure 4:
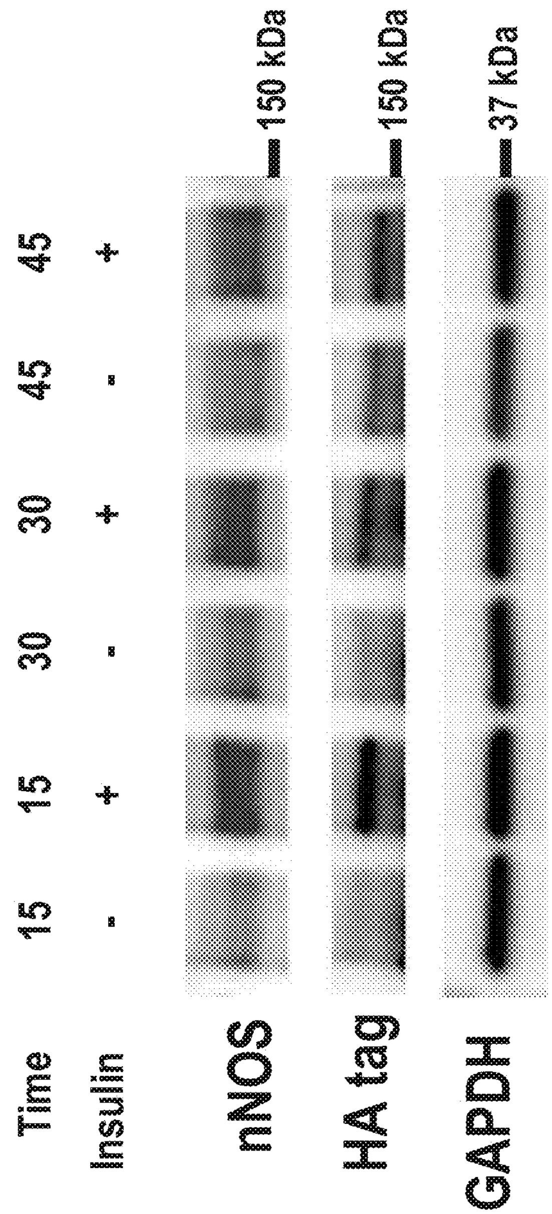
FIG. 4 illustrates western blot results from Experiment 1, described below, showing expression of nNOS and HA tag. GAPDH was used as a protein loading control. Incubation of the platform with muscle cells for only 15 min are shown to lead to expression of nNOS.

L6-GLUT4myc myoblasts in 6 well plates were transfected with the structure shown in FIG. 3. In this experiment, a plasmid was used containing a modified neuronal nitric oxide synthase construct (NOS-M), which included a C-terminal HA tag for detection and a RAS palmitoylation sequence for plasma membrane targeting (Rebolledo D L, et al. (2016). Sarcolemmal targeting of nNOSmu improves contractile function of mdx muscle. *Hum Mol Genet* 25, 158-166). This plasmid is driven by the human skeletal actin (HSA) promoter and is ~11 Kb in length. In this experiment, 10 μg of NOS-M plasmid were used for each well. The primary aims of this experiment were to test whether short-term incubation periods 15 to 45 minutes were sufficient for the antibody to bind to GLUT4myc, and to determine if the level of binding was enhanced by insulin. Following the incubation, the cells were washed and then harvested 3 days later for analysis of nNOS and HA tag expression by Western blot. As shown in FIG. 4, as little as 15 min incubation was sufficient to produce nNOS and HA expression, and protein levels after incubation for 30 and 40 min were similar. Importantly, at each time-point, 100 nM insulin markedly increased protein expression, indicating that binding and uptake of the structure into the cell was dependent on the movement of GLUT4 from the cytosol to the membrane.

Experiment 2

Figure 5:
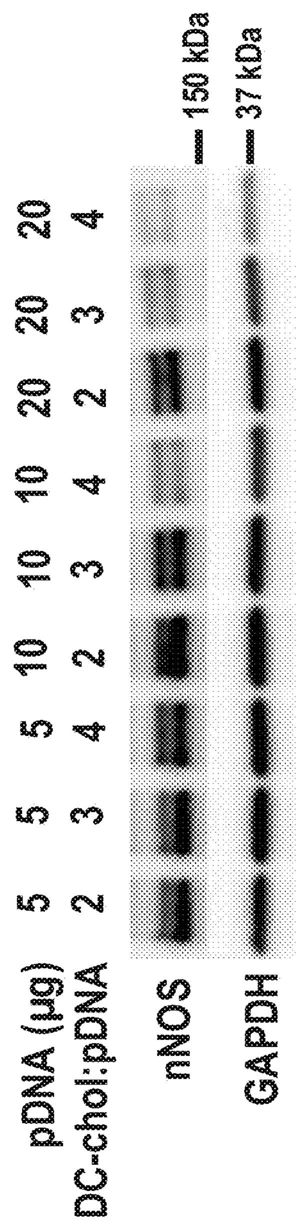
FIG. 5 illustrates western blot results from Experiment 2, described below, showing expression of nNOS. GAPDH was used as a protein loading control. Here, the effect of different plasmid DNA concentrations (pDNA) and different ratios of DC-chol:pDNA were tested.

There were two primary aims for the second experiment. The first aim was to test the effect of different amounts of plasmid DNA on uptake and expression. The second aim was to determine the optimal amounts of DNA relative to liposomes, as determined by the ratio of DC-Chol to DNA (w/w). As shown in FIG. 5, of all DNA concentrations, a DC-Chol to DNA ratio of 2.0 produced the highest expression of nNOS, in agreement with prior studies. In terms of DNA, 5 μg was sufficient to produce strong nNOS expression, while levels decreased at 20 μg, particularly for the higher DC-Chol to DNA ratios. Therefore, in future cell culture experiments between 5 and 10 μg of DNA were used at a DC-Chol to DNA ratio of 2.0.

Experiment 3

Figure 6:
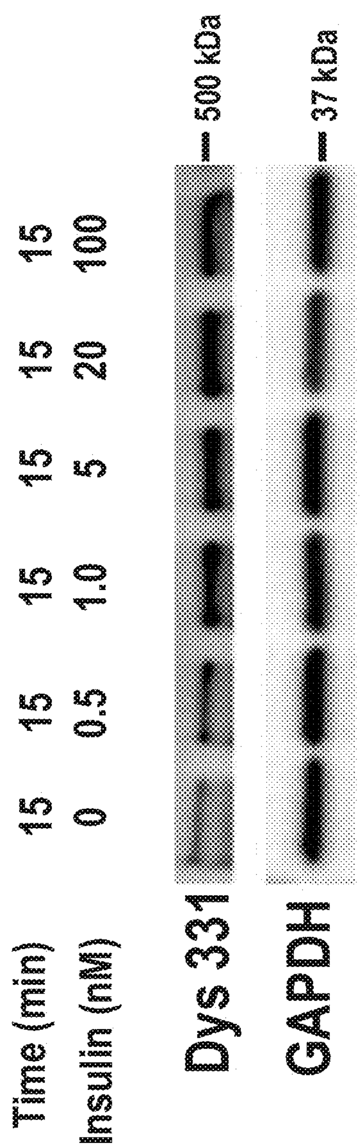
FIG. 6 illustrates western blot results from Experiment 3, described below, showing expression of full-length Dystrophin using the antibody 331 (C-terminal antibody) with increasing concentrations of administered insulin. GAPDH was used as a protein loading control. The results indicated that adding insulin up to 5 nM increased the expression of Dystrophin.

In this experiment, L6-GLUT4myc myoblasts were incubated with the same structure shown in FIG. 3, except here the NOS-M plasmid was replaced with a full-length Dystrophin plasmid. This construct is driven by the ubiquitous CAG promoter and is ~20 Kb in length (Farruggio A P, et al. (2017), *Biotechnol J* 12 (4), 1600477). The two primary aims of this experiment were (1) to test whether the very large dystrophin gene could be taken up in a targeted muscle cell and expressed using this targeting platform, and (2) to test the effects of a wide-range of insulin concentrations on the targeting and transduction of expression in muscle cells. The range of insulin begins with low levels normally found in human blood. In this experiment, cells were incubated with the vector for 15 min, washed and then harvested 3 days later. As shown in FIG. 6, full-length dystrophin was strongly expressed and dystrophin levels were greater in cells treated with insulin. Importantly, at low insulin concentrations normally found in human blood (0.5 and 1.0 nM), dystrophin expression increased compared to cells without insulin. These results support the hypothesis that enhancing or inducing GLUT4 movement to the plasma membrane by insulin leads to greater binding and uptake of the platform, and subsequent dystrophin expression.

Experiment 4

Both rabbit polyclonal and mouse monoclonal antibodies were generated against the peptide sequence (GRQGPGGPDSI; SEQ ID NO:4), taken from the first extracellular loop of mouse GLUT4. These antibodies all show strong binding to the peptide in an ELISA assay. See, e.g., Table 1, which show results of ELISA tests for 20 select mouse monoclonal antibodies.

TABLE 1

ELISA data showing the absorbance levels at various dilutions for 20 mouse monoclonal antibodies against the GLUT4 peptide sequence GRQGPGGPDSI (SEQ ID NO:4). All antibody cell lines strongly bind to the peptide.

| mAb | Supernatant Dilution | | | | | | Negative | |
|---|---|---|---|---|---|---|---|---|
| Cell lines | 1:10 | 1:30 | 1:90 | 1:270 | 1:810 | 1.2,430 | Control | Titer |
| 1B12-1 | 2.807 | 2.792 | 2.417 | 2.115 | 1.504 | 0.746 | 0.065 | >1:2,430 |
| 1B12-2 | 2.761 | 2.568 | 2.129 | 1.604 | 0.846 | 0.389 | 0.065 | 1:2,430 |
| 18B2-1 | 2.778 | 2.682 | 2.338 | 2.053 | 1.520 | 0.864 | 0.065 | >1:2,430 |
| 18B2-2 | 2.829 | 2.718 | 2.380 | 2.187 | 1.665 | 0.986 | 0.065 | >1:2,430 |
| 21E5-1 | 2.618 | 2.344 | 1.778 | 1.194 | 0.678 | 0.314 | 0.065 | 1:2,430 |
| 21E5-2 | 2.706 | 2.472 | 2.050 | 1.632 | 1.018 | 0.474 | 0.065 | 1:2,430 |
| 22E6-1 | 2.628 | 2.279 | 1.736 | 1.071 | 0.561 | 0.246 | 0.065 | 1:2,430 |
| 22F6-2 | 2.650 | 2.462 | 2.101 | 1.620 | 1.079 | 0.485 | 0.065 | 1:2,430 |
| 24B4-1 | 2.473 | 2.349 | 2.034 | 1.474 | 0.846 | 0.409 | 0.065 | 1:2,430 |
| 24B4-2 | 2.512 | 2.403 | 2.171 | 1.701 | 1.050 | 0.531 | 0.065 | >1:2,430 |
| 25D4-1 | 2.754 | 2.613 | 2.279 | 1.794 | 1.081 | 0.568 | 0.065 | >1:2,430 |
| 25D4-2 | 2.704 | 2.661 | 2.435 | 1.876 | 1.193 | 0.661 | 0.065 | >1:2,430 |
| 25H4-1 | 2.710 | 2.680 | 2.469 | 1.933 | 1.353 | 0.758 | 0.065 | >1:2,430 |
| 25H4-2 | 2.669 | 2.653 | 2.412 | 1.891 | 1.220 | 0.701 | 0.065 | >1:2,430 |
| 26A7-1 | 2.425 | 2.378 | 2.051 | 1.489 | 0.887 | 0.412 | 0.065 | 1:2,430 |
| 26A7-2 | 2.611 | 2.464 | 2.131 | 1.536 | 0.879 | 0.438 | 0.065 | 1:2,430 |
| 29C10-1 | 2.660 | 2.453 | 2.089 | 1.661 | 0.991 | 0.468 | 0.065 | 1:2,430 |
| 29C10-2 | 2.716 | 2.482 | 2.030 | 1.530 | 0.876 | 0.417 | 0.065 | 1:2,430 |
| 30F8-1 | 2.776 | 2.708 | 2.491 | 1.967 | 1.266 | 0.699 | 0.065 | >1.2,430 |
| 30F8-2 | 2.777 | 2.696 | 2.356 | 1.802 | 1.139 | 0.590 | 0.065 | >1:2,430 |

In this experiment, a rabbit polyclonal antibody was first purified by peptide affinity purification. Next, the ability of the antibodies to bind to native GLUT4 and mediate uptake of full-length dystrophin into dystrophin-negative (mdx-H2K) muscle cells (Morgan et al., 1994) was tested. While these cells do express some endogenous GLUT4, a determination if increasing GLUT4 expression further could improve the uptake and expression of our vector was desired. Therefore, the mdx-H2K cells were transfected with a plasmid containing the mouse GLUT4 gene (mdx-H2K-GLUT4) and, through antibacterial selection, a polyclonal cell line was established that has about two to three-fold higher GLUT4 expression. Using these dystrophin-negative cells, it was desired to assess whether increased GLUT4 expression resulted in greater binding and uptake of the platform non-viral vector, and therefore augmented dystrophin expression.

Figure 7:
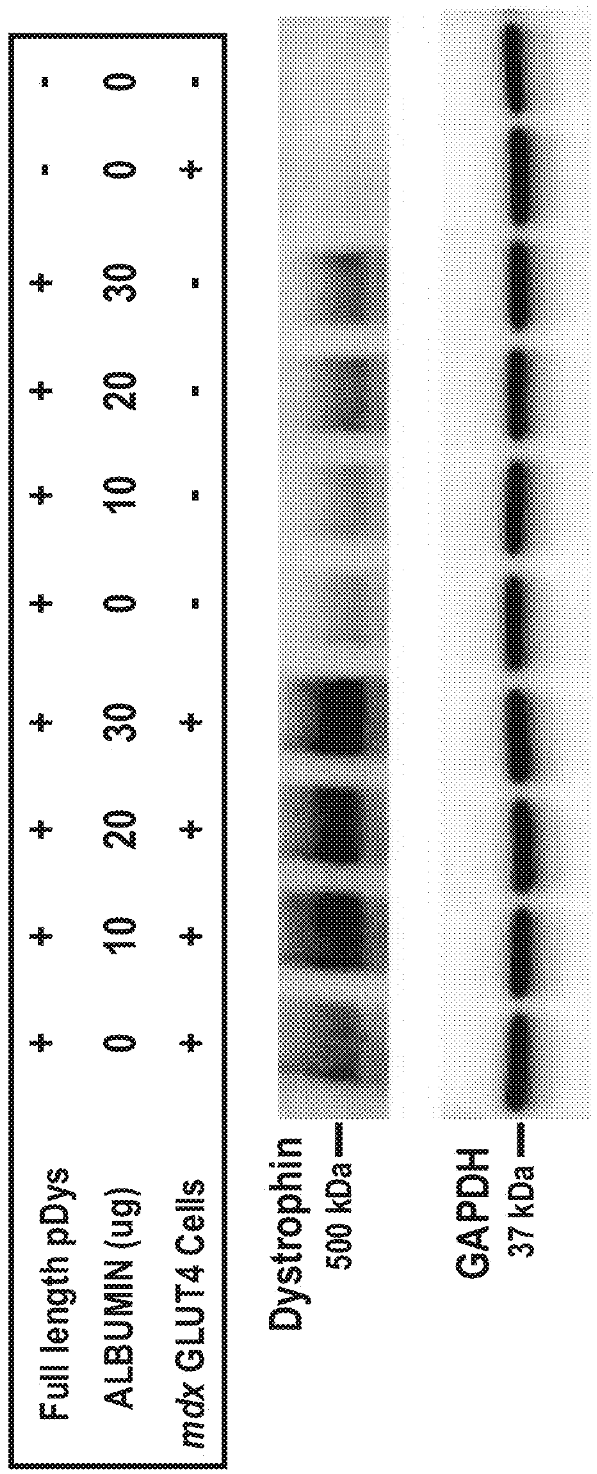
FIG. 7 illustrates western blot results from Experiment 4, described below, showing expression of full-length Dystrophin using the antibody 331 (C-terminal antibody). GAPDH was used as a protein loading control. As shown, Dystrophin expression is higher in cells overexpressing (+) GLUT4 (mdx GLUT4), and increasing amounts of Albumin added to the expression.

The other main aim of this experiment was to test whether albumin could enhance gene expression. The rationale for this idea is recent evidence that coating DNA/liposomal vectors with human serum albumin can enhance protein expression of the luciferase reporter in lung and spleen cells of mice. Because albumin is negatively charged at neutral pH, it can bind to the positively charged liposomes, along with the plasmid DNA. The results from this experiment reveal a number of important findings (FIG. 7). First, full-length dystrophin expression was detected and measured, indicating that the rabbit polyclonal antibodies were able to effectively bind to GLUT4 and deliver the plasmid inside muscle cells to the nucleus. Second, dystrophin expression was considerably greater in the mdx-H2K-GLUT4 cells compared to the regular mdx-H2K cells. Third, increasing concentrations of albumin enhanced dystrophin expression in both muscle cell lines.

In Vivo Experiments

DNA/liposomal vectors for in vivo administration can have potential problems due to the relatively large sizes (usually ≥200 nm) of these structures. Therefore, a non-liposomal alternative structure was developed (FIG. 8) for enhanced in vivo applications. Here, the plasmid DNA is highly condensed by positively-charged Poly-L-Lysine (PLL), into structures that can have a diameter as small as 30 to 60 nm for a 20 Kb plasmid Fink T L, et al. (2006). Plasmid size up to 20 kbp does not limit effective in vivo lung gene transfer using compacted DNA nanoparticles. *Gene Ther* 13, 1048-1051). The PLL is biotinylated, which enables subsequent binding to NeutrAvidin. Then, the biotinylated mouse monoclonal GLUT4 antibody is added.

Finally, biotinylated recombinant mouse serum albumin is added. It is postulated that albumin promotes in vivo administration of this structure for a number of reasons. (1) Albumin crosses the tight endothelial barrier of muscle capillaries by transcytosis. This provides a mechanism for the movement of albumin, and therefore the disclosed non-viral vector platform, from the bloodstream to the muscle extracellular space. (2) Albumin is known to preferentially accumulate in the extracellular space of skeletal and cardiac muscle. (3) Albumin can enter muscle cells by endocytosis. This may be of particular importance in dystrophic muscles, which have increased membrane permeability and accumulate albumin intracellularly. (4) Albumin has been shown to promote endosomal escape and nuclear uptake of plasmid DNA. (5) Albumin is very stable and has a long half-life in vivo of 19 days. (6) Albumin is very unlikely to elicit any side-effects or immune responses, considering that it is an abundant serum protein. This will permit repeated dosing of a therapeutic payload via the non-viral vector platform.

Experiment 5

Figure 9B:
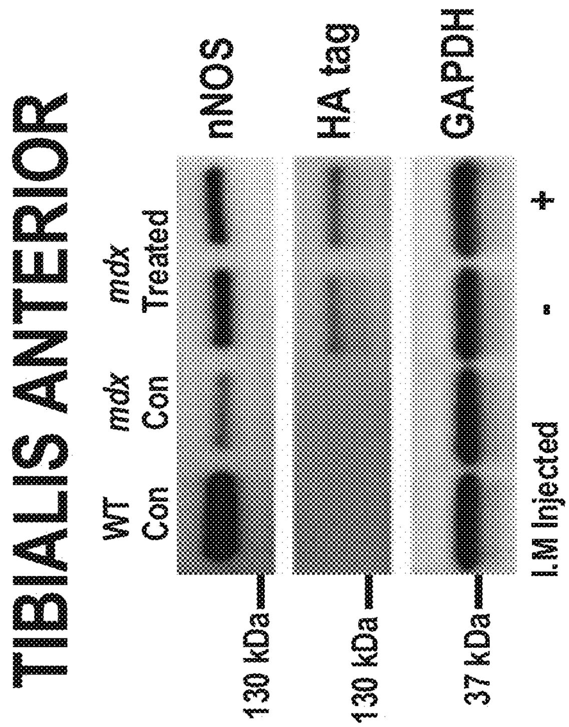
FIG. 9A-B illustrates western blot results from Experiment 5, described below, showing expression of nNOS and HA tag following in vivo administration of the platform without the GLUT4 antibody added. GAPDH was used as a protein loading control. Increased expression of both nNOS and the HA tag was observed in Gastrocnemius (9A) and Tibialis Anterior (9B) muscles of the treated mouse compared to the untreated mdx Con mouse. Both the injected (+) and noninjected (−) muscles show expression of nNOS, indicating that the composition was able to leak out of the injected muscles and achieve systemic circulation to ultimately transfect muscles in the contralateral (noninjected) limb.
Figure 9A:
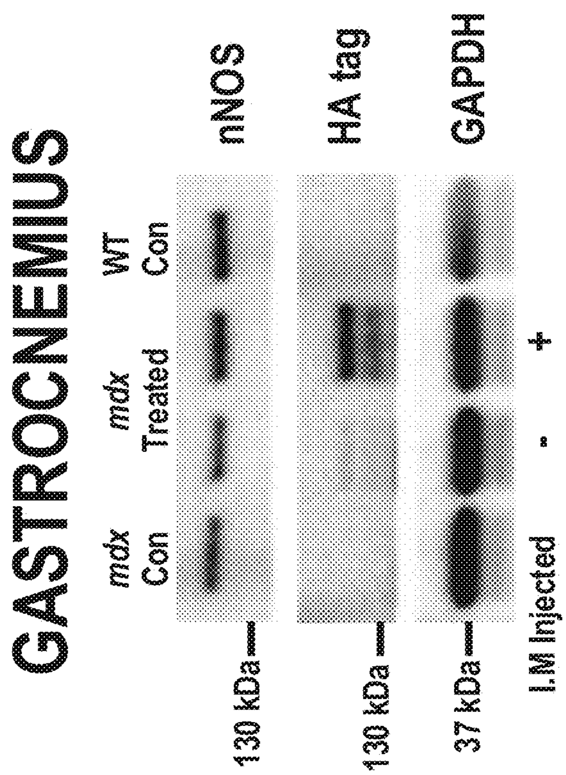

In this first in vivo experiment, intramuscular (I.M.) injections were initially performed using the structure shown in FIG. 8, without the GLUT4 antibody, to determine the baseline effect of the non-viral vector platform without the targeting antibody. Two muscles (Tibialis Anterior and Gastrocnemius) were injected in one leg of 8 week old mdx mice, a common animal model of DMD. The structure contained the NOS-M plasmid, described in Experiment 1. Interestingly, three days later, both the Tibialis Anterior and Gastrocnemius muscles expressed NOS-M, as shown by both an nNOS antibody and an HA tag antibody (FIG. 9A-B). Presumably, the more permeable muscle fibers of the mdx mice allowed some uptake of the albumin-containing structure. In comparison to the injected mdx mice, a non-injected mdx control mouse had endogenous nNOS expression but did not show any HA tag expression. A non-injected WT mouse had higher endogenous nNOS expression than the mdx mouse but also showed no HA tag expression. Another very interesting finding was that for both muscles, but particularly for the Tibialis Anterior muscle, there was NOS-M expression (HA tag) in both the injected and non-injected legs (see FIG. 9A-B). This indicates that the structure was able to enter the systemic circulation from the injected muscles, and subsequently be taken up by the non-injected muscles of the other leg.

Experiment 6

Figure 10B:
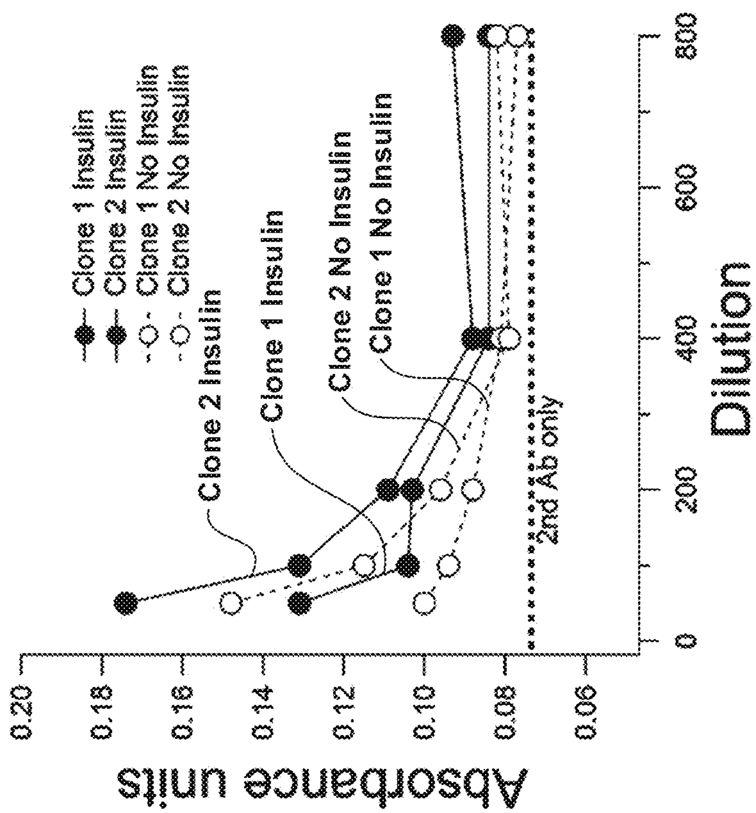
FIG. 10A-B. (10A) Coomassie stain showing the successful purification of two GLUT4 mAb clones using protein A/G columns. The coomassie stain of each clone is shown under non-reducing (NR) or reducing (R) conditions; (10B) graphically illustrates binding of mAb clones to native GLUT4 protein with and without insulin. Mdx myoblasts overexpressing GLUT4 were incubated with mouse mAb clones 1 & 2 (at different dilutions of a 1 mg/ml stock solution), with or without 100 nM insulin, for 20 min at 37° C. followed by a HRP-conjugated secondary antibody for the same time. Antibody binding (Absorbance) was measured using a colorimetric assay. The increased Absorbance shows that both clones bind to the native GLUT4 protein in vitro, with Clone 2 showing greater binding affinity than Clone 1. For both clones, insulin increases the Absorbance by trafficking more GLUT4 to the plasma membrane. The Absorbance of a secondary antibody only control is shown (dotted line).
Figure 10A:
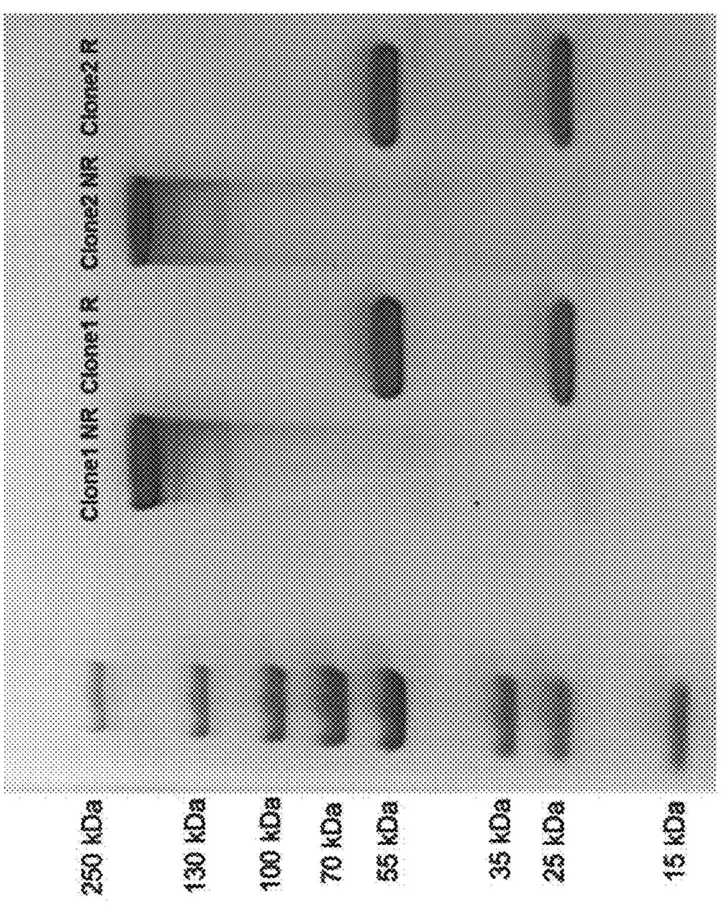

In the next experiment, the hypothesis that conjugating mouse monoclonal GLUT4 antibodies to the structure will greatly enhance uptake of our platform into muscles of mdx mice was tested. First, two mouse monoclonal antibodies were produced and purified. The correct molecular weight and purity of the antibodies was verified, under reducing and non-reducing conditions, by coomassie staining on a polyacrylamide gel (FIG. 10A). Then, the binding affinity of each antibody in vitro was tested using the mdx-H2K-GLUT4 muscle cell line. Specifically, cells were incubated with each antibody at different dilutions (from a 1 mg/ml starting concentration) for 20 min at 37° C., with or without 100 nM insulin. Cells were washed, incubated with a secondary-HRP antibody and washed again. A colorimetric assay was used to quantify the relative amount of bound antibody to the native GLUT4 protein by measuring the absorbance with a spectrophotometer. As shown in FIG. 10B, both antibodies, Clone 1 and Clone 2, bound to the native GLUT4 protein in a dose-dependent manner. At all dilutions, Clone 2 had a higher absorbance than Clone 1. Importantly, for both antibodies, insulin (100 nM) increased the absorbance (see FIG. 10B), indicating greater binding occurred when more GLUT4 was brought to the plasma membrane by insulin signaling.

Figure 11:
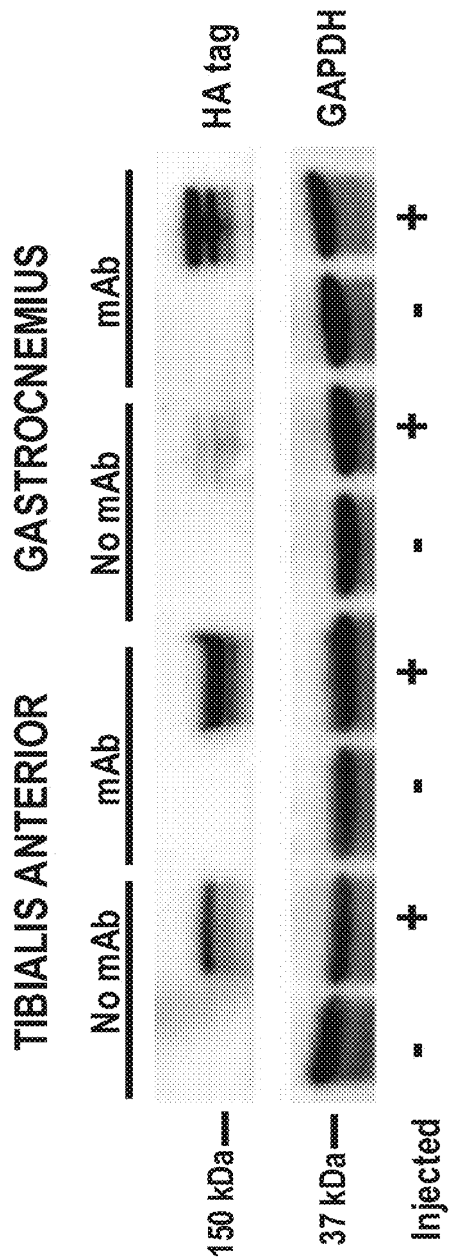
FIG. 11 illustrates western blot results from Experiment 6, described below, showing expression of the HA tag following in vivo administration (I.M. injection into the TA and Gastrocnemius) of the platform composition without ("No mAb") or with ("mAb") the GLUT4 antibody added. GAPDH was used as a protein loading control. A several fold increase in HA tag expression was observed in both muscles of the mouse treated with the mAb-conjugated platform composition.

Next, the Clone 2 antibody was biotinylated and incorporated into the non-viral vector platform by binding to NeutrAvidin. As a control the non-viral vector platform was also constructed without the antibody (as described in Experiment 5). Two mdx mice were injected I.M. with or without the antibody conjugated to the non-viral vector platform. Again, the TA and Gastrocnemius muscles were injected in one leg only. Six days after the injection, muscles were harvested and used for Western blot analysis. As shown in FIG. 11, the expression level of nNOS, as measured by the HA tag, was considerably (several fold) higher in both the TA and Gastrocnemius muscles of the mouse injected with the platform containing the Clone 1 mAb. This data indicates that the Glut4 antibody dramatically enhances the targeting and uptake of the non-viral vector platform into skeletal muscle.

Experiment 7

Figure 12A:
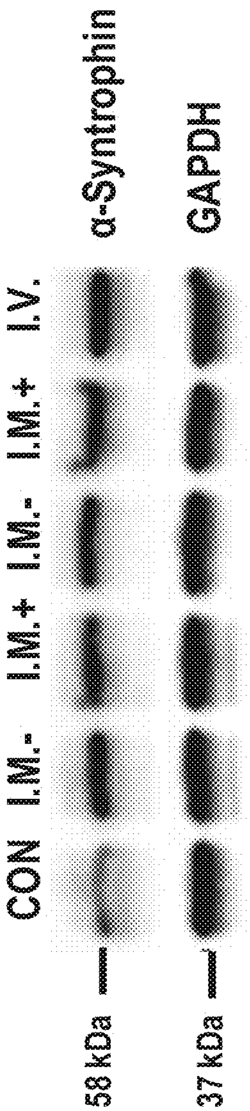
FIG. 12A-B illustrates results from Experiment 7, showing expression of α-syntrophin in mdx4CV mice following in vivo administration (I.M. injection into the TA and Gastrocnemius or I.V. injection via the retro-orbital sinus) of the platform composition containing the GLUT4 antibody (see FIG. 8). The α-syntrophin DNA construct contained a RAS palmitoylation sequence for targeting the protein to the muscle surface membrane (sarcolemma). (12A) Western blot results show much greater expression of α-syntrophin in muscles of both I.M. and I.V. injected mice compared to a non-injected control mdx4CV mouse. GAPDH was used as a protein loading control. (12B) Immunostaining of muscle cross-sections showing many muscle fibers with surface membrane localized α-syntrophin staining in both I.M. and I.V. injected mice, which is not evident in the non-injected control mouse. Note, the very bright areas of staining in some muscle fibers of the I.M. injected mouse are most likely neuromuscular junctions, which have more membrane surface area for α-syntrophin expression.
Figure 12B:
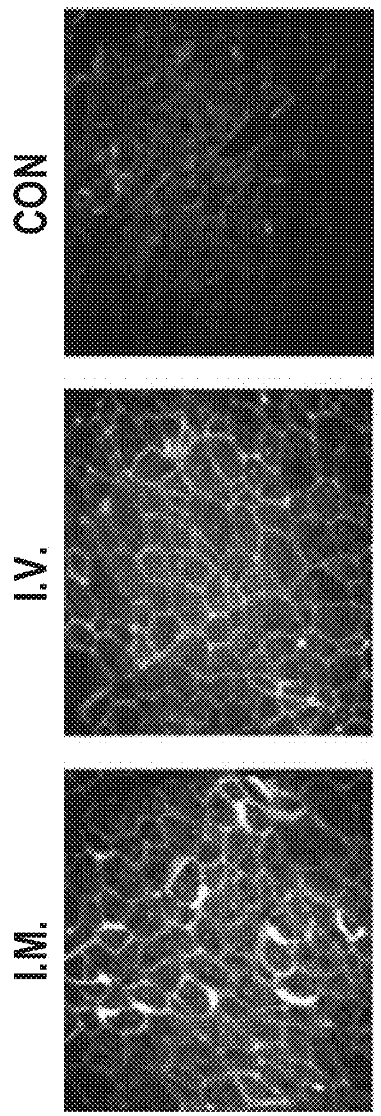

Next, it was tested whether intravenous (I.V.) administration of the targeted, non-viral platform could lead to systemic delivery and expression of the proteins encoding genes of various sizes in muscle. To test this hypothesis, three genes of different sizes were used (Experiments 7-9). In this experiment, the smallest of these genes was used. This gene is α-syntrophin, with a plasmid size of ~5.5 kb. Here, mdx4CV mice were injected I.M. or I.V. with the non-viral platform described in FIG. 11, containing the α-syntrophin gene, which has a RAS palmitoylation sequence at the C-terminal for targeting to the sarcolemma. Targeting of α-syntrophin to the sarcolemma in normal muscle occurs by interaction with dystrophin, which is absent in mdx4CV muscle. As shown in FIG. 12, both I.M. and I.V. delivery resulted in a considerable increase of α-syntrophin expression in muscle 12 days after injection, compared to a non-injected control mouse, both confirmed by Western blot (FIG. 12A) and Immunostaining (FIG. 12B) of muscle cross-sections.

Experiment 8

Figure 13A:
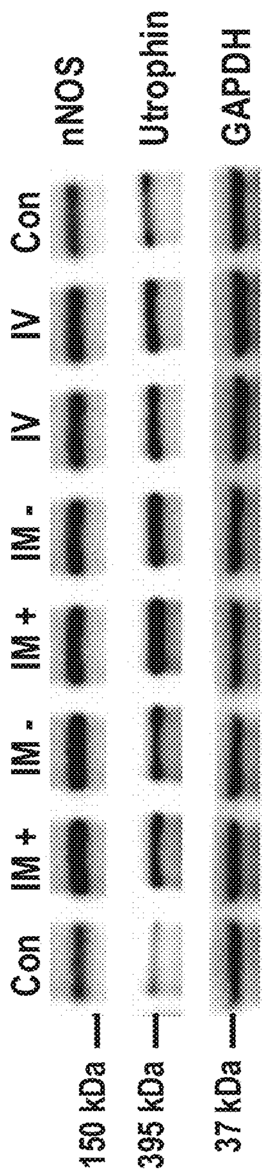
FIG. 13A-B illustrates western blot results from Experiment 8, showing expression of nNOS in mdx4CV mice following in vivo administration of the platform containing the nNOS construct described in FIG. 11. (13A) Here, two mice were injected I.M. in the gastrocnemius muscle of one hindlimb and two mice were injected I.V. via the retro-orbital sinus. The Western blot shows that both I.M. and I.V. injections led to a considerable increase in nNOS expression in the gastrocnemius compared to two gastrocnemius muscles from a non-injected mdx4CV control mouse. Consistent with previous experiments, the I.M. injection resulted in increased nNOS expression in muscles of both the injected (I.M.+) and contralateral (I.M.−) legs, indicating a systemic distribution of the platform following I.M. delivery. In addition, the dystrophin homologue, utrophin, was also considerably increased in the muscles of mice injected with the platform. GAPDH was used as a loading control. (13B) Three mdx mice were injected I.V. with different amounts of nNOS plasmid (20, 60 or 120 μg). As shown by Western blot, both nNOS and HA tag expression levels are progressively higher as the plasmid dose increases. GAPDH was used as a loading control.
Figure 13B:
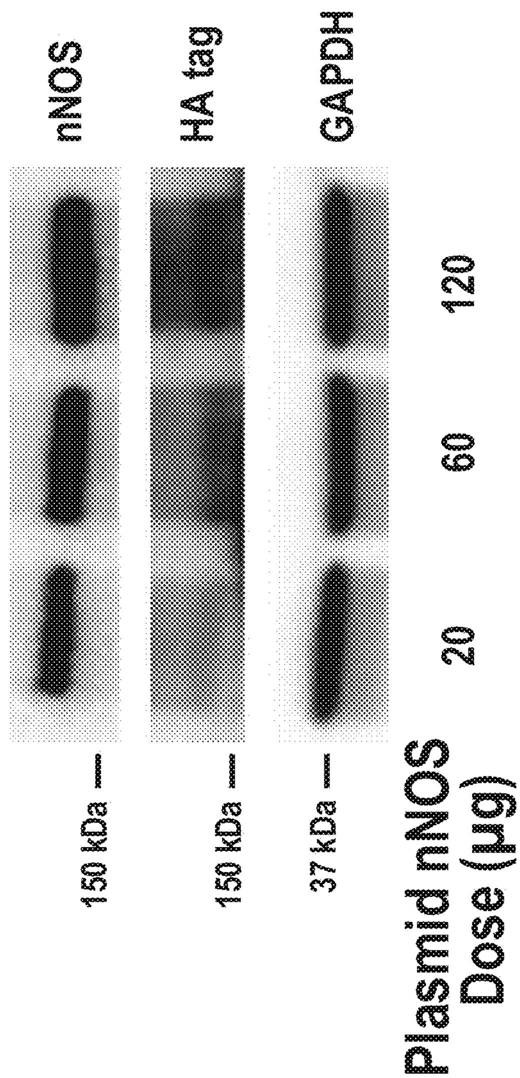

The second gene was nNOS, as described in FIG. 11, with a plasmid size of ~10.5 kb. Again mdx4CV mice were injected either I.M. or I.V. Specifically, two mice were injected I.M. in the gastrocnemius muscle of one hindlimb and two mice were injected I.V. via the retro-orbital sinus. As shown in FIG. 13A, nNOS expression was considerably higher (~50%) in muscles of mice after I.M. and I.V. injections compared to an untreated control muscle. Utrophin (a homologue of dystrophin) expression was also measured here by Western blot where it was shown to increase considerably in mice injected with the nNOS construct (see FIG. 13A). In another experiment, the effect of nNOS plasmid dose was investigated. Here, mdx mice were injected I.V. with the platform containing different doses of nNOS plasmid (20, 60 or 120 μg). As shown in FIG. 13B, there was a progressive increase in nNOS expression in the TA muscle as the nNOS plasmid dose was increased, as measured both by nNOS and HA tag expression.

Experiment 9

Figure 14:
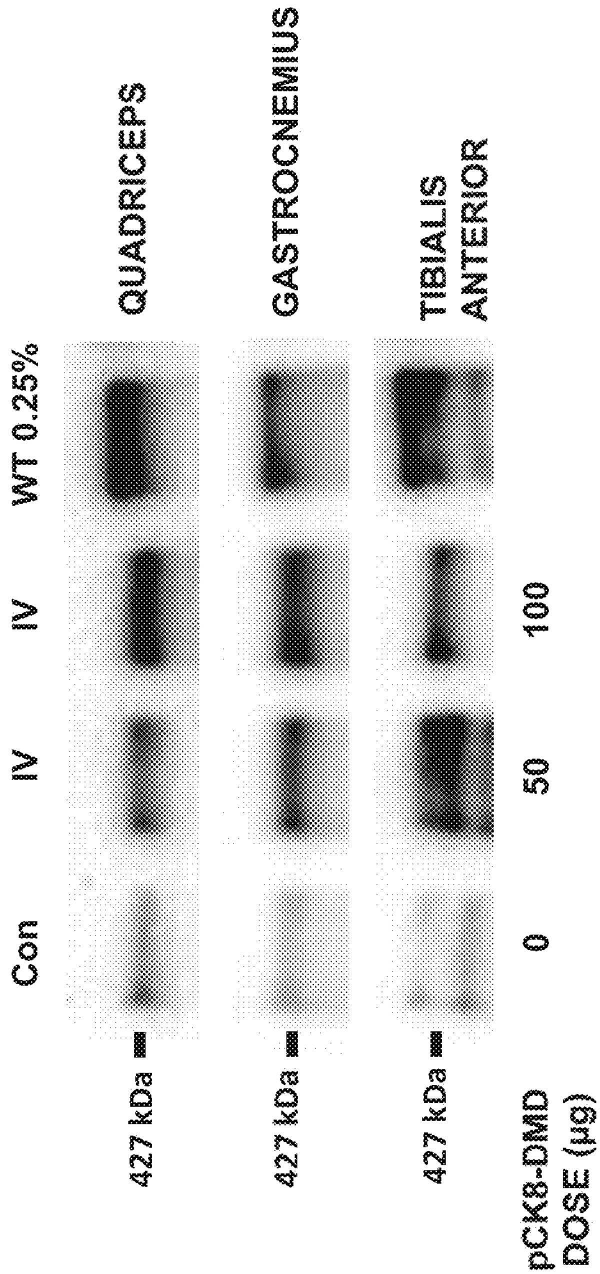
FIG. 14 illustrates results from Experiment 9, where expression of full-length dystrophin in muscles was measured following systemic delivery of the non-viral platform composition (see FIG. 8). Two mdx4CV mice were injected I.V. with different doses of the platform containing 50 or 100 μg of the CK8-dystrophin construct. As shown by Western blot, both doses show full-length dystrophin expression in three hindlimb muscles (Quadriceps, Gastrocnemius and Tibialis Anterior), with levels ~0.2 to 0.25% of a WT mouse. The total protein loaded into the WT well was the same as all other wells, but consisted of 0.25% WT protein mixed with 99.75% mdx4CV Con protein. The faint bands in the non-injected mdx4CV Control mouse are indicative of the very small number of revertant fibers that express low levels of dystrophin in mdx mice.
Figure 15:
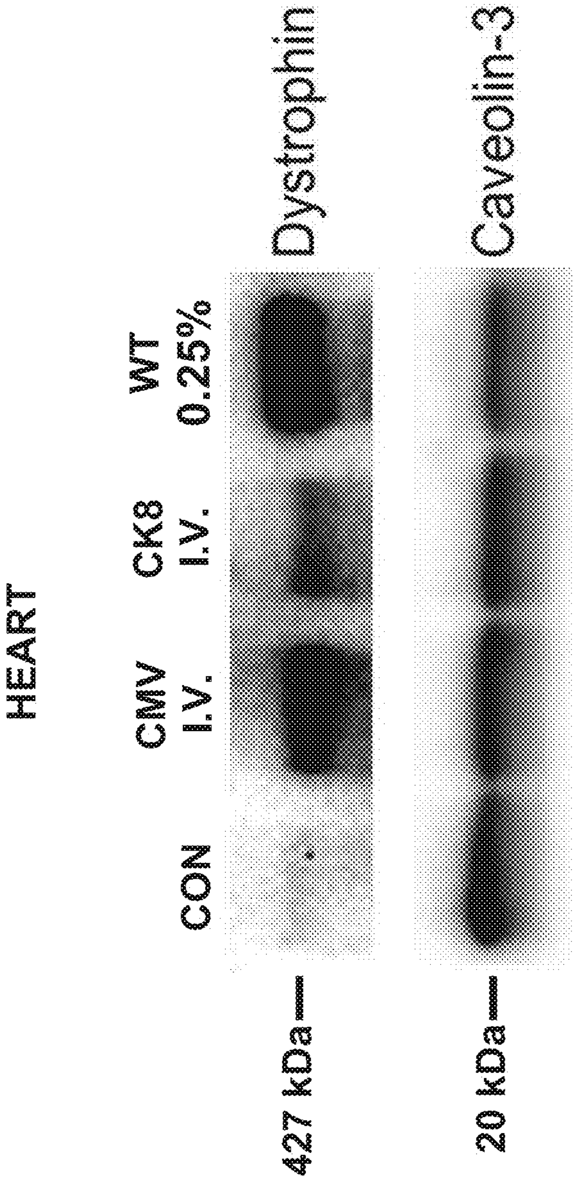
FIG. 15 highlights results from Experiment 9 showing expression of full-length dystrophin in cardiac muscle following systemic delivery of the platform composition (see FIG. 8). Two mdx4CV mice were injected I.V. with the platform containing either CK8-dystrophin or the CMV-dystrophin construct. As shown by Western blot, both constructs resulted in full-length dystrophin expression in the Heart with the CMV-dystrophin plasmid displaying a higher level than the CK8 construct. Here, the expression level in cardiac muscle was also ~0.1-0.2% of a WT mouse. The total protein loaded into the WT well was the same as all other wells but consisted of 0.25% WT protein mixed with 99.75% mdx4CV Con protein. Caveolin-3 was used as a membrane-specific loading control.

The third and largest gene tested was full-length mouse dystrophin. Here, two plasmid constructs were used, each containing full-length dystrophin but with different promoters and plasmid backbones. The first construct contained the truncated muscle-specific creatine kinase 8 promoter (CK8) (PMID: 21266958, PMID: 19298131). This construct was 15.5 kb. The second construct contained the ubiquitous cytomegalovirus (CMV) promoter. This construct was 17.5 kb. As shown in FIG. 14, mdx4CV mice injected I.V. with the CK8 construct showed expression of full-length dystrophin in a number of hindlimb muscles. The levels of expression were much higher than a non-injected mdx4CV mouse, which had faint bands on the Western blot due to the presence of a very small number of revertant fibers that express dystrophin (PMID: 1635838). Also, in this experiment we used a membrane-enriched muscle lysate for Western blotting, which likely enables even very low levels of skeletal muscle dystrophin in revertant fibers to be detected. Comparison with a WT mouse showed dystrophin levels in the injected mice ranging from ~0.2 to 0.5% for different muscles. Next, we injected mdx4CV mice I.V. with the platform containing either the CK8 or the CMV construct to measure dystrophin expression in the heart. Importantly, as shown in FIG. 15, cardiac muscles of injected mice showed clear expression of full-length dystrophin compared with a non-injected control. The level of dystrophin expression was higher with the CMV construct compared to CK8, with values ~0.1 to 0.2% of a WT mouse. Together, the data from Experiments 8 and 9 indicate that the non-viral platform composition (see FIG. 8) containing a large gene such as full-length dystrophin is effectively taken up and expressed by both skeletal and cardiac muscle.

Experiment 10

Figure 20:
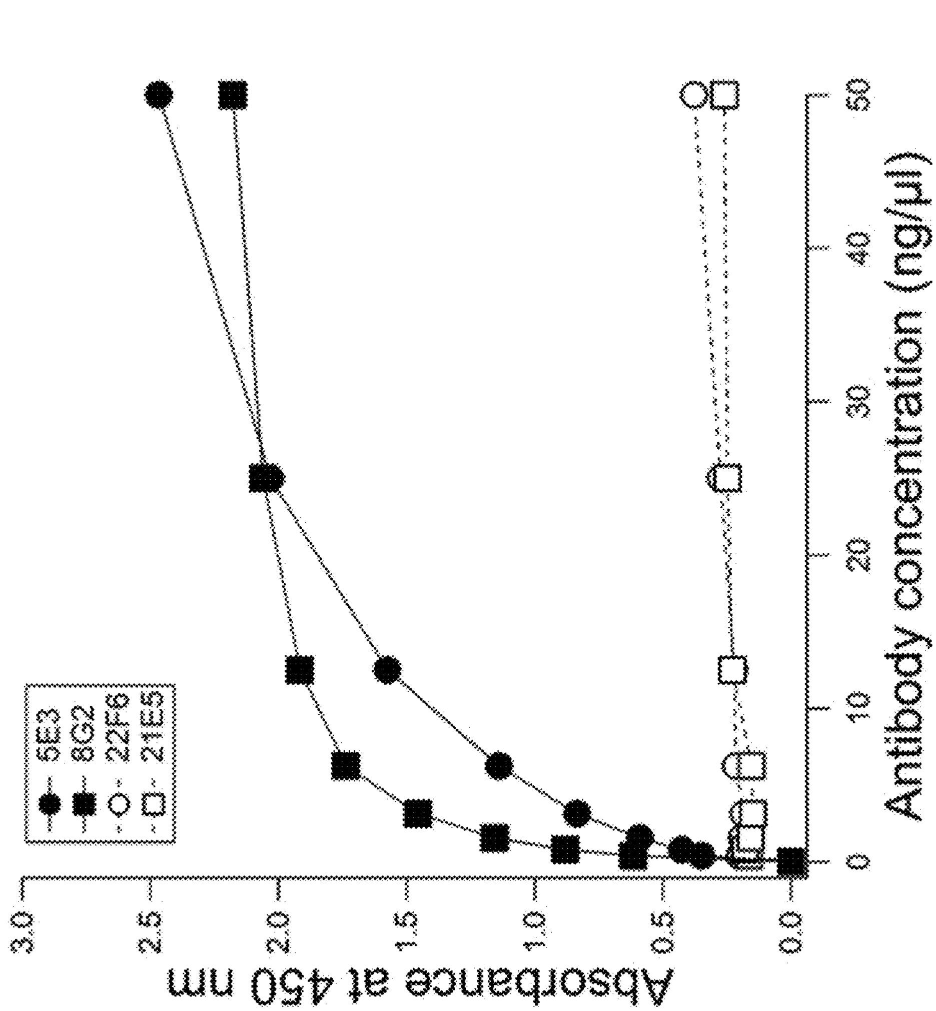
FIG. 20 demonstrates the ELISA assay results from Experiment 11, aimed at testing whether antibodies made against the mouse GLUT4 sequence (GRQGPGGPDSI; SEQ ID NO:4) could bind to the human GLUT4 sequence (GRQGPEGPSSI; SEQ ID NO:2.). As shown, antibodies made against the mouse sequence (22F6 and 21E5) bound very weakly to the antigen, while antibodies to the human sequence bound strongly (5E3, 8G2).

In this experiment, particle tracking analysis was performed in order to determine the size distribution of the particles produced using our non-viral platform. Here, the platform composition (see FIG. 8) contained the CK8-full-length dystrophin plasmid. Particle tracking analysis was performed using the standard procedures for the NanoSight ns300 (Malvern Panalytical), which allows reliable, rapid measurement of nanoparticle size distribution of particles ranging in diameter from 0.01 to 1.0 μm. The platform sample was diluted 1:100 with deionized water and then 4 separate readings were carried out of the particle size distribution. As shown in FIG. 20, the particle size distribution plot indicates that the modal (peak) particle size was 171 nm. Overall, the mean particle size was 236 nm±4.4 and. Data analysis illustrated that 50% of the particles were less than 213 nm, and 90% of particles were less than 344 nm. The mean size of our particles is very similar to the mean size of particles containing NeutrAvidin and siRNA (237 nm), which were effective at in vivo gene silencing in mice (PMID: 28026957). Therefore, the data presented in this experiment indicates that even with a large plasmid DNA such as full-length dystrophin (15.5 kb), the non-viral platform forms small particles that can be efficiently taken up and expressed by muscle in vivo (see FIGS. 14 and 15).

Experiment 11

Figure 16A:
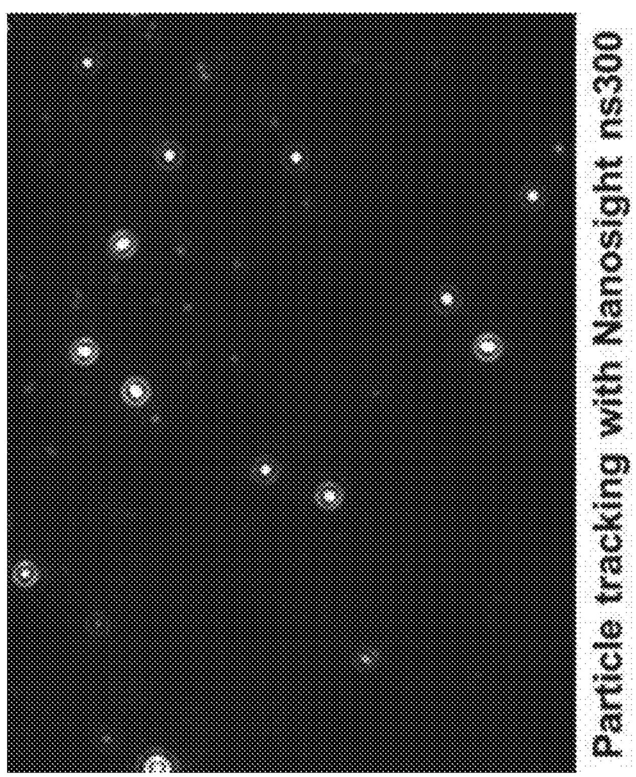
FIG. 16A-B demonstrates results from Experiment 10, showing particle tracking analysis of the non-viral platform composition (see FIG. 8) containing the CK8-full-length dystrophin plasmid. (16A) An image of the platform particles identified and tracked by the Nanosight ns300 software for size analysis. (16B) A plot of the particle distribution, showing the particle sizes against particle concentration. Values are the mean±SEM of 4 separate inputs from the same sample.
Figure 16B:
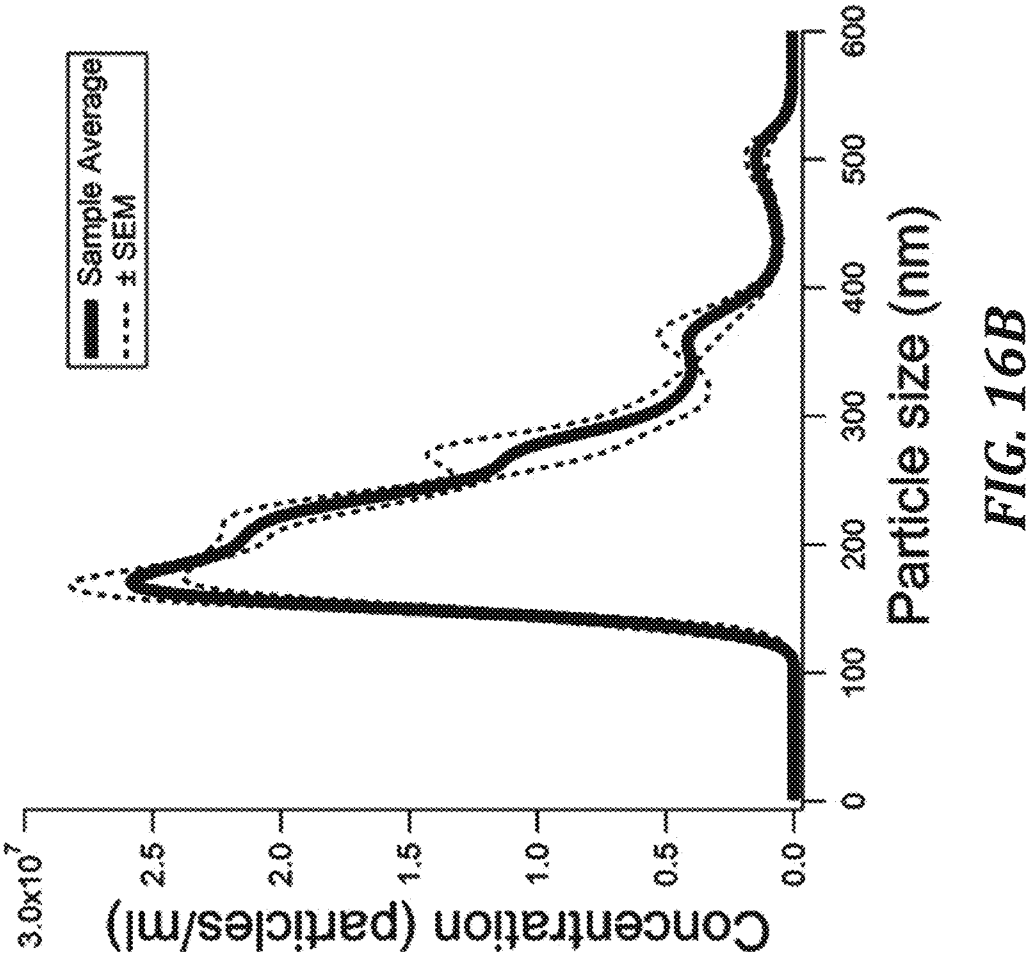
Figure 17:
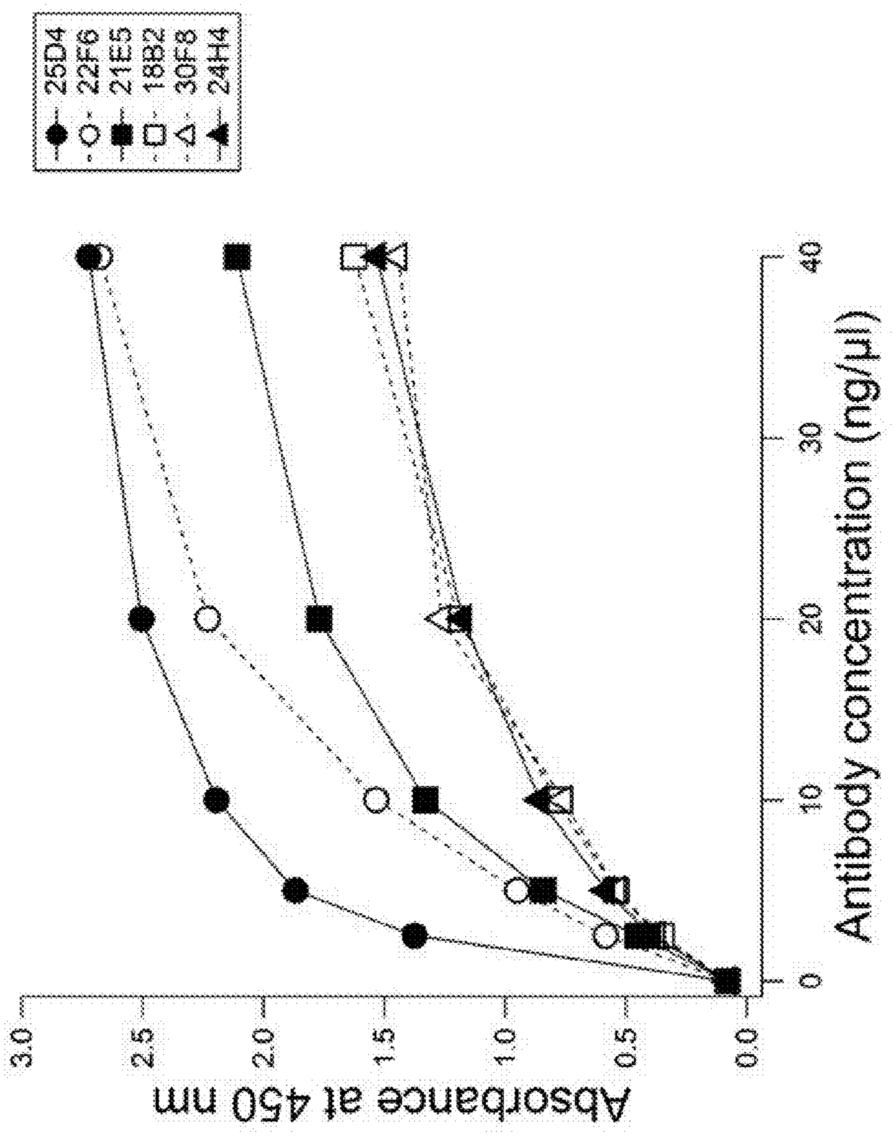
FIG. 17 illustrates results from Experiment 11, where an ELISA assay was designed to measure the binding affinity of 6 monoclonal antibodies made against the mouse peptide sequence of GLUT4 (GRQGPGGPDSI; SEQ ID NO:4). As shown, all antibodies displayed a dose-dependent increase in absorbance, indicative of increased binding to the mouse GLUT4 peptide.

In this experiment, a number of monoclonal antibodies against GLUT 4 were produced and the binding affinity of each antibody was evaluated. Mouse monoclonal antibodies against both the mouse GLUT4 peptide (GRQGPGGPDSI; SEQ ID NO:4) and human GLUT4 peptide (GRQGPEGPSSI; SEQ ID NO:2.) were manufactured by Genscript (NJ, USA). A total of 14 unique clones were generated; 6 against the mouse GLUT4 sequence and 8 against the human GLUT4 sequence. Each hybridoma cell line was grown in cell culture for several weeks and monoclonal antibodies were purified using protein A/G latex beads. The binding affinity of each monoclonal antibody was measured by ELISA. For the mouse GLUT4 sequence antibodies, the ELISA plate was coated with the peptide (SEQ ID NO:4). For the human GLUT4 sequence antibodies, recombinant human GLUT4 protein was used to coat the ELISA plate. In both cases, each well of the ELISA plate was coated with 100 ng of antigen overnight at 4° C. After blocking, the monoclonal antibodies were added for 1 hr at RT. After washing, secondary mouse-HRP antibody was added for 1 hr at RT. After further washing, a chromogenic substrate for HRP (1-STEP™ Ultra TMB-ELISA substrate solution; Thermo Fisher Scientific) was added for 10 to 20 min. Finally, the reaction was stopped by adding 2M sulfuric acid and the absorbance at 450 nm was measured on a plate reader. As shown in FIG. 16, all 6 monoclonal antibodies displayed a concentration-dependent increase in absorbance. The best binding clones were 25D4 followed by 22F6 and 21E5. The other three clones showed similar, lower binding curves (see FIG. 16). For the human GLUT for sequence monoclonal antibodies, the same method was used, except the plate was coated with recombinant human GLUT4 protein. As shown in FIG. 17, 7 monoclonal antibodies displayed a dose-dependent increase in absorbance, with clones 5E3 and 8G2 having the best binding affinity and clones 2B9 and 4G2 showing the weakest binding affinity. One clone, 15G2, was not able to be assayed due to insufficient antibody production by this hybridoma cell line.

Figure 18:
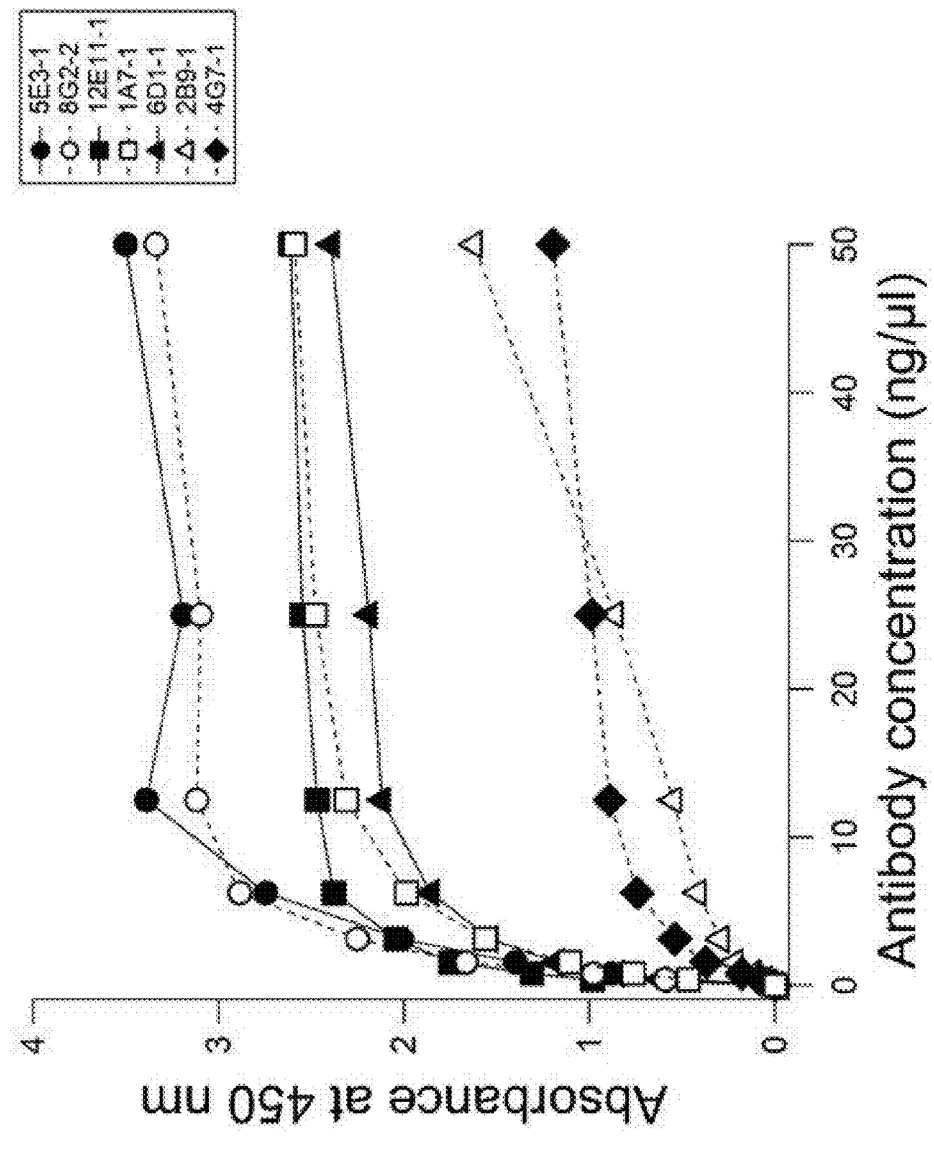
FIG. 18 demonstrates results from Experiment 11 of an ELISA assay aimed at testing the binding affinity of 7 monoclonal antibodies made against the human peptide sequence of GLUT4 (GRQGPEGPSSI; SEQ ID NO:2.). As presented, all antibodies displayed a dose-dependent increase in absorbance, indicative of increased binding to the recombinant human GLUT4 protein.
Figure 19:
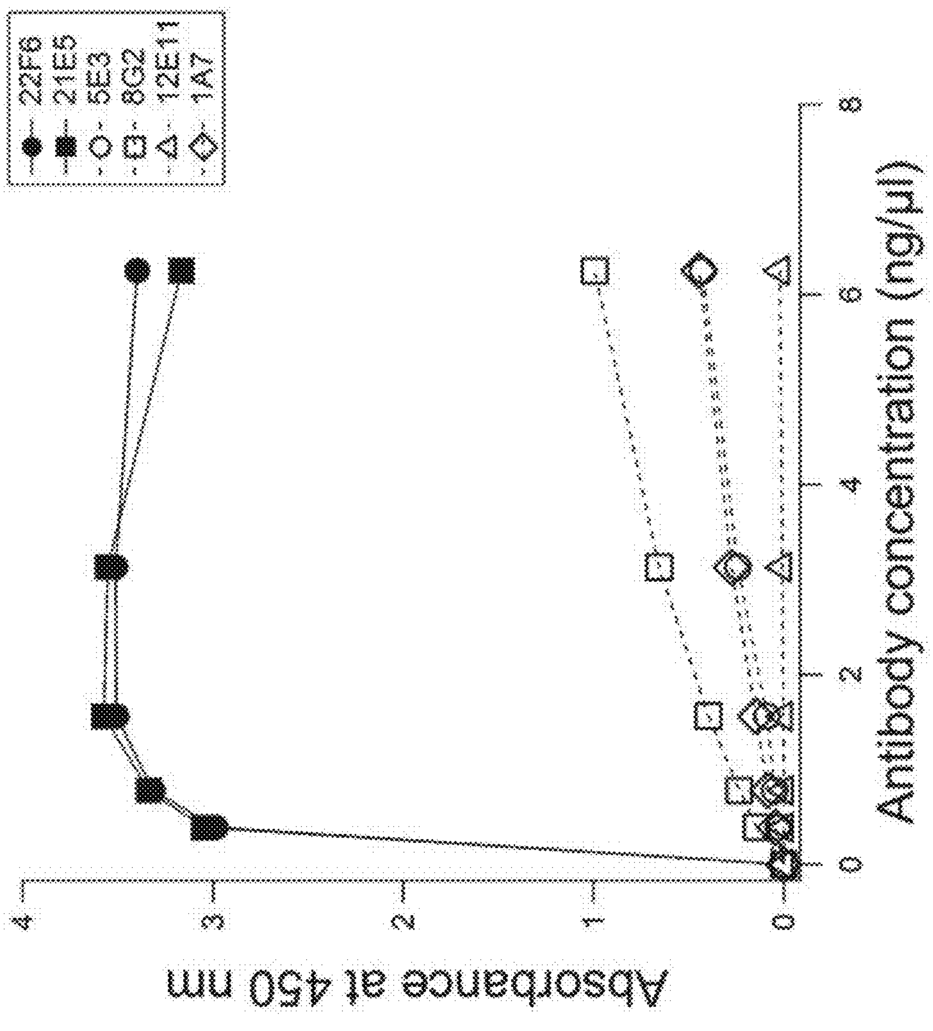
FIG. 19 shows the results from Experiment 11, where an ELISA assay was designed to test whether antibodies made against the human GLUT4 sequence (GRQGPEGPSSI; SEQ ID NO:2.) could bind to the mouse GLUT4 peptide sequence (GRQGPGGPDSI; SEQ ID NO:4). As displayed, antibody clones made against the human sequence (5E3, 8G2, 12E11, 1A7) bound the mouse peptide much more weakly than antibodies made against the mouse sequence (22F6 and 21E5), which reached binding saturation at a relatively low concentration (~2 ng/ml).

In order to test whether the mouse sequence antibodies could bind to the human GLUT4 protein or whether the human sequence antibodies could bind to the mouse GLUT4 peptide sequence, two additional ELISA experiments were carried out. As shown in FIG. 18, two antibodies that bound strongly to the mouse sequence (22F6 and 21E5) did not bind effectively to the human GLUT4 protein, while antibodies made against the human GLUT4 peptide sequence (5E3 and 8G2) showed strong binding. As shown in FIG. 19, in the reverse experiment, antibodies made against the human GLUT4 sequence bound with varying degrees of affinity to the mouse GLUT4 peptide (8G2 was the best while 12E11 did not bind) but all four of these antibodies bound much less strongly than antibodies made against the mouse sequence (22F6 and 21E5). Therefore, despite 83.3% homology between the mouse and human peptide sequences, the antibodies produced show much stronger binding to the species-specific GLUT4 sequence against which they were derived.

Experiment 12

For each of the 14 unique monoclonal antibodies generated; 6 against the mouse GLUT4 sequence and 8 against the human GLUT4 sequence, the heavy and light chain variable regions were sequenced by GenScript (NJ, USA) using the following method. Total RNA was isolated from the hybridoma cells (TRIzol® Reagent). Total RNA was then reverse-transcribed into cDNA using either isotype-specific anti-sense primers or universal primers (PrimeScript™ 1st Strand cDNA Synthesis Kit). Antibody fragments of heavy chain and light chain were amplified according to the standard operating procedure (SOP) of rapid amplification of cDNA ends (RACE) of GenScript. Amplified antibody fragments were cloned into a standard cloning vector separately. Colony PCR was performed to screen for clones with inserts of correct sizes and the sequences of each antibody were provided. In Table 2, the Complementarity Determining Regions (CDRs) for the Heavy and Light chains are shown for the 6 monoclonal antibodies produced against the mouse GLUT 4 peptide (GRQGPGGPDSI; SEQ ID NO:4). Predicted consensus sequences are also shown for each CDR. In Table 3, the Complementarity Determining Regions (CDRs) for the Heavy and Light chains are shown for the 8 monoclonal antibodies produced against the human GLUT 4 peptide (GRQGPEGPSSI; SEQ ID NO:2.). Predicted consensus sequences are also shown for each CDR. Interestingly, two clones (2B9 and 4G7) that bound most weakly to the human GLUT protein in the ELISA assay (see FIG. 17) did not contain the arginine (R) found in the $CDR3_{VH}$ consensus sequence of the other 6 clones, suggesting that this reside may have an important role in antigen binding activity. Note also that clone 15G2 was not represented in the ELISA assay (see FIG. 17) since this antibody did not grow well under our culture conditions.

Table 2 shows the results from Experiment 12, listing the amino acid sequences of the Complementarity Determining Regions (CDRs) for the Heavy Chain ($V_H$) and Light Chain ($V_L$) of 6 mouse monoclonal antibody clones against the mouse GLUT4 peptide sequence GRQGPGGPDSI (SEQ ID NO:4). Also shown below Table 2 is an illustrative consensus sequence for each CDR.

| Clone(s) | CDR1 ($V_H$) | CDR2 ($V_H$) | CDR3 ($V_H$) |
|---|---|---|---|
| 25D4 | TYGMS (SEQ ID NO: 58) | WINTSSGVPTYADDFKG (SEQ ID NO: 60) | PIHMVVAEDY (SEQ ID NO: 66) |
| 24H4 | TYGMT (SEQ ID NO: 59) | WINTYSGVPTYANDFKG (SEQ ID NO: 61) | PIHKVVAEDY (SEQ ID NO: 67) |

-continued

| | | | |
|---|---|---|---|
| 22F6 | TYGMS (SEQ ID NO: 58) | WINTYSGLPTYTNDFKG (SEQ ID NO: 62) | PITTVVPFDY (SEQ ID NO: 68) |
| 21E5 | TYGMS (SEQ ID NO: 58) | WINTYSGLPTYADDFKG (SEQ ID NO: 63) | PITTVVPFDY (SEQ ID NO: 69) |
| 18B2 | TYGMS (SEQ ID NO: 58) | WINTYSGVPTYADDFKG (SEQ ID NO: 64) | PITKVVAGDF (SEQ ID NO: 70) |
| 30F8 | TYGMS (SEQ ID NO: 58) | WINTFSGVPTYTDDFKG (SEQ ID NO: 65) | PITTVVPFDY (SEQ ID NO: 71) |

| Clone(s) | CDR1 ($V_L$) | CDR2 ($V_L$) | CDR3 ($V_L$) |
|---|---|---|---|
| 25D4 | KSSQILLYGRNQKNYLA (SEQ ID NO: 72) | WASTRES (SEQ ID NO: 78) | QQYYSKPYT (SEQ ID NO: 84) |
| 24H4 | RSSQSLLYSGNQKNYLA (SEQ ID NO: 73) | WASTWES (SEQ ID NO: 79) | QQYYTFPYT (SEQ ID NO: 85) |
| 22F6 | RSSQSLVYTYGNTYLH (SEQ ID NO: 74) | KVSNRFS (SEQ ID NO: 80) | SQSRHSPWT (SEQ ID NO: 86) |
| 21E5 | RSSQSLVYNYGNTYLH (SEQ ID NO: 75) | KVSNRFS (SEQ ID NO: 81) | SQSRHSPWT (SEQ ID NO: 87) |
| 18B2 | KSSQSLLYRSNQKNYLA (SEQ ID NO: 76) | WASTRES (SEQ ID NO: 82) | QQYFSSPYT (SEQ ID NO: 88) |
| 30F8 | RSSQSLVYSTGNTYLH (SEQ ID NO: 77) | KVSNRFS (SEQ ID NO: 83) | SQSRHGPWT (SEQ ID NO: 89) |

CDR consensus sequences
CDR1 ($V_H$): T Y G M S/T (SEQ ID NO: 90)
CDR2 ($V_H$): W I N T Y/F/S S G L/V P T Y X X D F K G (SEQ ID NO: 91)
CDR3 ($V_H$): P I H/T X V V A/P X D Y (SEQ ID NO: 92)
CDR1 ($V_L$): K/R S S Q S L L/V Y $X_{5-6}$ Y L A/H (SEQ ID NO: 93)
CDR2 ($V_L$): K/W A/V S N/T R E/F S (SEQ ID NO: 94)
CDR3 ($V_L$): Q Q S/Y F/R/Y H/S/T X P Y/W T (SEQ ID NO: 95)

Table 3 shows the results from Experiment 12, listing amino acid sequences of the Complementarity Determining Regions (CDRs) for the Heavy Chain ($V_H$) and Light Chain ($V_L$) of 8 monoclonal antibody clones against the human GLUT4 peptide sequence GRQGPEGPSSI (SEQ ID NO:2). Also shown below Table 3 is an illustrative consensus sequences for each CDR.

| Clone | CDR1 ($V_H$) | CDR2 ($V_H$) | CDR3 ($V_H$) |
|---|---|---|---|
| 2B9 | DDAMH (SEQ ID NO: 10) | WINTETGEPTYADDFKG (SEQ ID NO: 18) | LDF (contained in SEQ ID NO: 26) |
| 4G7 | DYSMH (SEQ ID NO: 11) | WINTETGEPTYADDFKG (SEQ ID NO: 19) | GASGY (SEQ ID NO: 27) |
| 5E3 | EYTIH (SEQ ID NO: 12) | GINCNSGGTSYTQKFKD (SEQ ID NO: 20) | RFFYGSSQFAY (SEQ ID NO: 28) |
| 15G2 | DYSMH (SEQ ID NO: 13) | WINTETGEPTYADDFKG (SEQ ID NO: 21) | RGEF (SEQ ID NO: 29) |
| 8G2 | DFSMH (SEQ ID NO: 14) | WINTETGDPTYADDFKG (SEQ ID NO: 22) | RGDY (SEQ ID NO: 30) |
| 1A7 | AYSMH (SEQ ID NO: 15) | WINTETGEATYADDFKG (SEQ ID NO: 23) | RGDY (SEQ ID NO: 31) |

-continued

| | | | |
|---|---|---|---|
| 6D1 | DYSMH (SEQ ID NO: 16) | WINTETGEPTYADDFKG (SEQ ID NO: 24) | RGDY (SEQ ID NO: 32) |
| 12E11 | DYSMH (SEQ ID NO: 17) | WINTETGEPTYADDFKG (SEQ ID NO: 25) | GRSAY (SEQ ID NO: 33) |
| Clone | CDR1 ($V_L$) | CDR2 ($V_L$) | CDR3 ($V_L$) |
| 2B9 | RSSQSLVHSNGKTYLH (SEQ ID NO: 34) | KVSNRFS (SEQ ID NO: 42) | SQSTHVPWT (SEQ ID NO: 50) |
| 4G7 | KASQSVSKNVA (SEQ ID NO: 35) | SSSKRYS (SEQ ID NO: 43) | HQDYNSPWT (SEQ ID NO: 51) |
| 5E3 | RASKSVTTSGYSYMH (SEQ ID NO: 36) | LASNLES (SEQ ID NO: 44) | QHSRELPLT (SEQ ID NO: 52) |
| 15G2 | KASQSVNKNVA (SEQ ID NO: 37) | SASKRYT (SEQ ID NO: 45) | LQDYTSPWT (SEQ ID NO: 53) |
| 8G2 | RSSQSLVHSNRNIYLH (SEQ ID NO: 38) | KVSNRFS (SEQ ID NO: 46) | SQDKYIPWT (SEQ ID NO: 54) |
| 1A7 | RSSQSLVRSNRNIYLH (SEQ ID NO: 39) | KVSNRFS (SEQ ID NO: 47) | SQDSHIPWT (SEQ ID NO: 55) |
| 6D1 | RSSQSLVHNNRNIYLH (SEQ ID NO: 40) | KVSNRFS (SEQ ID NO: 48) | SQDRYIPWT (SEQ ID NO: 56) |
| 12E11 | KASQTVSNNVA (SEQ ID NO: 41) | SASNRYT (SEQ ID NO: 49) | QQDYSSPWT (SEQ ID NO: 57) |

CDR consensus sequences
CDR1 ($V_H$): D/E Y S/T I/M H (SEQ ID NO: 96)
CDR2 ($V_H$): W I N T E S/T G D/E X T/S Y A D D F K G (SEQ ID NO: 97)
CDR3 ($V_H$): R X X Y (SEQ ID NO: 98), $RX_2X_3Y$ (SEQ ID NO: 98)
CDR1 ($V_L$): R/K A/S S Q S L/V X X N/S (SEQ ID NO: 99), R/K A/S S Q S L/V $X_4$ $X_5$ N/S (SEQ ID NO: 99)
CDR2 ($V_L$): V/A S N R F/Y S/T (SEQ ID NO: 100)
CDR3 ($V_L$): Q D X X X P W T (SEQ ID NO: 101), $QDX_6X_7X_8PT$ (SEQ ID NO: 101)

CONCLUSION

It is demonstrated that the disclosed non-viral vector platform can efficiently and specifically deliver therapeutic payloads to tissues that express GLUT4, including but not limited to skeletal muscle, cardiac muscle, adipose tissue, smooth muscle, certain areas of the brain (e.g. hippocampus and cerebellum) and certain cancer cells (e.g. melanocytes). Therapeutics that can be delivered to these tissues by our platform include nucleic acids (e.g., plasmid DNA, mini-circle DNA, mRNA, siRNA, shRNA, oligonucleotides, CRISPR/Cas9 constructs) proteins, peptides, lipids and drugs. The platform is not limited to payloads of particular sizes, but rather can successfully deliver vary large nucleic acid constructs resulting in the uptake and expression of the encoded large transgenes. The effects and efficiencies of the targeting and uptake are augmented further by insulin induction of GLUT4 translocation to the cell's plasma membrane and by incorporation of albumin to the platform vector composition. Therapeutic compositions incorporating the disclosed non-viral vector platform can be delivered as a monotherapy or as part of a combination therapy.

While illustrative embodiments have been illustrated and described, it will be appreciated that various changes can be made therein without departing from the spirit and scope of the invention.

What is claimed is:

1. A method of treating a disease or condition in a subject with a genetic mutation in a gene encoding dystrophin protein, comprising administering to a subject a therapeutically effective amount of a composition comprising:

(a) an antibody, or fragment or derivative thereof, that specifically binds glucose transporter 4 ("GLUT4") protein; and (b) a therapeutic payload conjugated to the antibody, or fragment or derivative thereof, wherein the therapeutic payload comprises a nucleic acid with a promoter sequence operatively linked to a sequence encoding a dystrophin protein, or a functional fragment thereof;

wherein the antibody, or fragment or derivative thereof, that specifically binds GLUT4 protein comprises a heavy chain variable region ($V_H$) and a light chain variable region ($V_L$), wherein:

i) the $V_H$ comprises a VH-CDR1 having a sequence set forth in SEQ ID NO: 10, a VH-CDR2 having a sequence set forth in SEQ ID NO:18, and a VH-CDR3 having a sequence LDF; and the $V_L$ comprises a VL-CDR1 having a sequence set forth in SEQ ID NO:34, a VL-CDR2 having a sequence set forth in SEQ ID NO:42, and a VL-CDR3 having a sequence set forth in SEQ ID NO:50;

ii) the $V_H$ comprises a VH-CDR1 having a sequence set forth in SEQ ID NO: 11, a VH-CDR2 having a sequence set forth in SEQ ID NO:19, and a VH-CDR3 having a sequence set forth in SEQ ID NO:27; and the $V_L$ comprises a VL-CDR1 having a sequence set forth in SEQ ID NO:35, a VL-CDR2 having a sequence set forth in SEQ ID NO:43, and a VL-CDR3 having a sequence set forth in SEQ ID NO:51;

iii) the $V_H$ comprises a VH-CDR1 having a sequence set forth in SEQ ID NO: 12, a VH-CDR2 having a sequence set forth in SEQ ID NO:20, and a VH-CDR3 having a sequence set forth in SEQ ID NO:28; and the $V_L$ comprises a VL-CDR1 having a sequence set forth in SEQ ID NO:36, a VL-CDR2 having a sequence set forth in SEQ ID NO:44, and a VL-CDR3 having a sequence set forth in SEQ ID NO:52;

iv) the $V_H$ comprises a VH-CDR1 having a sequence set forth in SEQ ID NO: 13, a VH-CDR2 having a sequence set forth in SEQ ID NO:21, and a VH-CDR3 having a sequence set forth in SEQ ID NO:29; and the $V_L$ comprises a VL-CDR1 having a sequence set forth in SEQ ID NO:37, a VL-CDR2 having a sequence set forth in SEQ ID NO:45, and a VL-CDR3 having a sequence set forth in SEQ ID NO:53;

v) the $V_H$ comprises a VH-CDR1 having a sequence set forth in SEQ ID NO: 14, a VH-CDR2 having a sequence set forth in SEQ ID NO:22, and a VH-CDR3 having a sequence set forth in SEQ ID NO:30; and the $V_L$ comprises a VL-CDR1 having a sequence set forth in SEQ ID NO:38, a VL-CDR2 having a sequence set forth in SEQ ID NO:46, and a VL-CDR3 having a sequence set forth in SEQ ID NO:54;

vi) the $V_H$ comprises a VH-CDR1 having a sequence set forth in SEQ ID NO: 15, a VH-CDR2 having a sequence set forth in SEQ ID NO:23, and a VH-CDR3 having a sequence set forth in SEQ ID NO:31; and the $V_L$ comprises a VL-CDR1 having a sequence set forth in SEQ ID NO:39, a VL-CDR2 having a sequence set forth in SEQ ID NO:47, and a VL-CDR3 having a sequence set forth in SEQ ID NO:55;

vii) the $V_H$ comprises a VH-CDR1 having a sequence set forth in SEQ ID NO: 16, a VH-CDR2 having a sequence set forth in SEQ ID NO:24, and a VH-CDR3 having a sequence set forth in SEQ ID NO:32; and the $V_L$ comprises a VL-CDR1 having a sequence set forth in SEQ ID NO:40, a VL-CDR2 having a sequence set forth in SEQ ID NO:48, and a VL-CDR3 having a sequence set forth in SEQ ID NO:56; or viii) the $V_H$ comprises a VH-CDR1 having a sequence set forth in SEQ ID NO: 17, a VH-CDR2 having a sequence set forth in SEQ ID NO:25, and a VH-CDR3 having a sequence set forth in SEQ ID NO:33; and the $V_L$ comprises a VL-CDR1 having a sequence set forth in SEQ ID NO:41, a VL-CDR2 having a sequence set forth in SEQ ID NO:49, and a VL-CDR3 having a sequence set forth in SEQ ID NO:57.

2. The method of claim 1, wherein the subject has or is a genetic carrier of Duchenne muscular dystrophy ("DMD") or Becker muscular dystrophy ("BMD").

3. The method of claim 1, wherein:

(a) the antibody is a monoclonal antibody; or (b) the antibody fragment or antibody derivative is or comprises an Fab fragment, or an F(ab)2 fragment.

4. The method of claim 1, wherein the composition further comprises a plurality of cationic peptide moieties associated with the nucleic acid, thereby resulting in condensed nucleic acid.

5. The method of claim 1, wherein the composition further comprises albumin.

6. The method of claim 1, wherein the subject is a human.

7. The method of claim 1, wherein the composition further comprises a liposome associated with the nucleic acid.

8. The method of claim 7, wherein the liposome comprises one or more lipids selected from DC-Cholesterol·HCl, 3b-[N—(N',N'-dimethylaminoethane)-caramoyl]cholesterol hydrochloride ("DC-Chol"), 1,2-dioleoyl-sn-glycero-3-phosphoethanolamine ("DOPE"), 1,2-di-O-octadecenyl-3-trimethylammonium ("DOTMA"), N-[1-(2,3-Dioleoyloxy) propyl]-N,N,N-trimethylammonium propane ("DOTAP"), dimethyldioctadecylammonium bromide ("DDAB"), 1,2-dimyristoyl-3-trimethylammonium-propane ("DMTAP"), 1,2-dioleoyl-3-dimethylammonium-propane ("DODAP"), cholesteryl hemisuccinate ("CHEMS") and cholesterol ("CHOL"), 2,3-dioleyloxy-N-[2 (sperminecarboxamido) ethyl]-N,N-dimethyl-1-propanaminium ("DOSPA"), Di-octadecyl-amido-glycyl-spermine ("DOGS"), and dioleoylphosphatidylcholine ("DOPC").

9. The method of claim 7, wherein the liposome further comprises polyethylene glycol ("PEG").

10. The method of claim 1, wherein the antibody, or fragment or derivative thereof, is biotinylated.

11. The method of claim 10, wherein the composition further comprises neutravidin.

12. The method of claim 1, wherein the nucleic acid is in linear form, plasmid form, or minicircle form.

13. The method of claim 1, wherein the composition further comprises a histone protein or a plurality of histone proteins associated with the nucleic acid.

14. The method of claim 13, wherein the histone protein or at least a portion of the plurality of histone proteins is biotinylated.

15. The method of claim 4, wherein the cationic peptide moieties are or comprise poly-L-Lysine ("PLL"), linear Polyethylenimine ("LPEI"), branched Polyethylenimine ("BPEI"), chitosan, spermidine and spermine, Polyamidoamine ("PAMAM"), poly(2-dimethylaminoethyl methacrylate) ("PDMAEMA"), Poly(beta-amino ester)s ("PBAEs"), poly {N—[N-(2-aminoethyl)-2-aminoethyl]aspartamide ("PAsp(DET)") or poly(2-aminoethyl ethylene phosphate ("PPEEA").

16. The method of claim 4, wherein at least a portion of the plurality the cationic peptide moieties is biotinylated.

17. The method of claim 5, wherein at least a portion of the albumin is biotinylated.

* * * * *